(12) United States Patent
Kesteleyn et al.

(10) Patent No.: US 10,730,884 B2
(45) Date of Patent: Aug. 4, 2020

(54) SUBSTITUTED INDOLE COMPOUND DERIVATIVES AS DENGUE VIRAL REPLICATION INHIBITORS

(71) Applicants: Janssen Pharmaceuticals, Inc., Titusville, NJ (US); Katholieke Universiteit Leuven, Leuven (BE)

(72) Inventors: Bart Rudolf Romanie Kesteleyn, Belare (BE); Jean-François Bonfanti, Ande (FR); Pierre Jean-Marie Bernard Raboisson, Rosieres (BR); Dorothée Alice Marie-Eve Bardiot, Heverlee (BE); Arnaud Didier M Marchand, Bierbeek (BE); Erwin Cosemans, Nijlen (BE)

(73) Assignees: Janssen Pharmaceuticals, Inc., Titusville, NJ (US); Katholieke Universiteit Leuven, Leuven (BE)

( * ) Notice: Subject to any disclaimer, the term of this patent is extended or adjusted under 35 U.S.C. 154(b) by 0 days.

(21) Appl. No.: 16/088,198

(22) PCT Filed: Mar. 31, 2017

(86) PCT No.: PCT/EP2017/057662
§ 371 (c)(1),
(2) Date: Sep. 25, 2018

(87) PCT Pub. No.: WO2017/167952
PCT Pub. Date: Oct. 5, 2017

(65) Prior Publication Data
US 2019/0276467 A1    Sep. 12, 2019

(30) Foreign Application Priority Data

Apr. 1, 2016 (EP) .................................. 16163482

(51) Int. Cl.
| | |
|---|---|
| *A61P 31/12* | (2006.01) |
| *A61P 31/14* | (2006.01) |
| *A61P 35/00* | (2006.01) |
| *C07D 209/12* | (2006.01) |
| *C07D 209/14* | (2006.01) |
| *C07D 491/048* | (2006.01) |
| *C07F 9/572* | (2006.01) |

(52) U.S. Cl.
CPC .......... *C07D 491/048* (2013.01); *A61P 35/00* (2018.01); *C07D 209/12* (2013.01); *C07D 209/14* (2013.01); *C07F 9/5728* (2013.01)

(58) Field of Classification Search
CPC .......... A61P 31/12; A61P 31/14; A61P 35/00; C07D 209/12; C07D 209/14; C07D 491/048

See application file for complete search history.

(56) References Cited

U.S. PATENT DOCUMENTS

| | | | |
|---|---|---|---|
| 7,601,735 B2 | 10/2009 | Tyms et al. | |
| 8,524,764 B2 | 9/2013 | Canales et al. | |
| 8,884,030 B2 | 11/2014 | Canales et al. | |
| 8,993,604 B2 | 3/2015 | Byrd et al. | |
| 9,029,376 B2 | 5/2015 | Byrd et al. | |
| 9,522,923 B2 | 12/2016 | Richards et al. | |
| 9,944,598 B2 * | 4/2018 | Kesteleyn | C07D 209/14 |
| 10,029,984 B2 | 7/2018 | Kesteleyn et al. | |
| 10,064,870 B2 | 9/2018 | Rajagopalan et al. | |
| 10,071,961 B2 | 9/2018 | Vandyck et al. | |
| 10,117,850 B2 | 11/2018 | Griffioen et al. | |
| 10,206,902 B2 * | 2/2019 | Kesteleyn | A61P 31/00 |
| 10,323,026 B2 | 6/2019 | Ikeda et al. | |
| 10,550,123 B2 * | 2/2020 | Bardiot | A61P 31/12 |
| 2005/0239821 A1 | 10/2005 | Neyts et al. | |
| 2006/0194835 A1 | 8/2006 | Dugourd et al. | |
| 2006/0211698 A1 | 9/2006 | Botyanszki et al. | |
| 2008/0318338 A1 | 12/2008 | Kamal et al. | |
| 2016/0297810 A1 | 10/2016 | Bardiot et al. | |
| 2017/0002006 A1 | 1/2017 | Corte et al. | |
| 2017/0096429 A1 | 4/2017 | Corte et al. | |
| 2017/0281633 A1 | 10/2017 | Boylan et al. | |
| 2017/0281766 A1 | 10/2017 | Wiltzius | |
| 2017/0283500 A1 | 10/2017 | Wiltzius et al. | |

(Continued)

FOREIGN PATENT DOCUMENTS

| | | |
|---|---|---|
| WO | 02089780 A2 | 11/2002 |
| WO | 03050295 A2 | 6/2003 |

(Continued)

OTHER PUBLICATIONS

Prasad L. Polavarapu, et al., Intrinsic Rotation and Molecular Structure, Chirality 15: S143-S149 (2003).
Ian Stansfield et al., Development of carboxylic acid replacements in indole-N-acetamide inhibitors of hepatitis C virus NS5B polymerase, Bioorganic & Medicinal Chemistry Letters 17 (2007) 5143-5149, ScienceDirect (2007), www.sciencedirect.com, internet.
Boltromeyuk V.V., Obshchaya khimiya (General Chemistry), Minsk, Vysheyshaya shkola, 2012, p. 65) (translation).
Banker, et al., (1996) Modern Pharmaceuticals, 3rd Edition, Revised and Expanded, p. 596.

(Continued)

*Primary Examiner* — Sun Jae Yoo
(74) *Attorney, Agent, or Firm* — Amster, Rothstein & Ebenstein LLP

(57) ABSTRACT

The present invention concerns substituted indole compounds, methods to prevent or treat dengue viral infections by using said compounds and also relates to said compounds for use as a medicine, more preferably for use as a medicine to treat or prevent dengue viral infections. The present invention furthermore relates to pharmaceutical compositions or combination preparations of the compounds, to the compositions or preparations for use as a medicine, more preferably for the prevention or treatment of dengue viral infections. The invention also relates to processes for preparation of the compounds.

6 Claims, No Drawings
Specification includes a Sequence Listing.

(56) References Cited

U.S. PATENT DOCUMENTS

| | | |
|---|---|---|
| 2017/0298017 A1 | 10/2017 | Kesteleyn et al. |
| 2018/0256544 A1 | 9/2018 | Kesteleyn et al. |
| 2018/0256545 A1 | 9/2018 | Kesteleyn et al. |
| 2018/0346419 A1 | 12/2018 | Kesteleyn et al. |
| 2019/0104738 A1 | 4/2019 | Narine et al. |
| 2019/0112266 A1 | 4/2019 | Kesteleyn et al. |
| 2019/0183931 A1 | 6/2019 | Bakker et al. |

FOREIGN PATENT DOCUMENTS

| | | |
|---|---|---|
| WO | 2009149054 A1 | 12/2009 |
| WO | WO 2010/021878 A1 | 2/2010 |
| WO | 2011037643 A2 | 3/2011 |
| WO | 2011088303 A1 | 7/2011 |
| WO | WO 2013/045516 A1 | 4/2013 |
| WO | 2016050841 A1 | 4/2016 |
| WO | 2016053455 A1 | 4/2016 |
| WO | 2017079216 A1 | 5/2017 |
| WO | 2017167832 A1 | 10/2017 |
| WO | 2017167950 A1 | 10/2017 |
| WO | 2017167952 A1 | 10/2017 |
| WO | 2017167953 A1 | 10/2017 |
| WO | 2017171100 A1 | 10/2017 |
| WO | 2017173206 A1 | 10/2017 |
| WO | 2017173256 A1 | 10/2017 |
| WO | 2017173384 A1 | 10/2017 |
| WO | 2017173410 A1 | 10/2017 |
| WO | 2018178238 A1 | 10/2018 |
| WO | 2018178240 A1 | 10/2018 |
| WO | 2018215315 A1 | 11/2018 |
| WO | 2018215316 A1 | 11/2018 |

OTHER PUBLICATIONS

Wolff et al., Burger's Medicinal Chemistry and Drug Discovery, 5th Ed. part 1, p. 975-977 (1995).

Prevention, Dengue, Centers for Disease Control and Prevention (Sep. 27, 2012) https://www.cdc.govidengue/prevention/index.html, internet.

Lidia Moreira Lima et al., Bioisosterism: A Useful Strategy for Molecular Modification and Drug Design, Current Medicinal Chemistry, Bentham Science Publishers Ltd. (2005) 12, pp. 23-49.

N.C.B.I.: "qHTS for inhibitors of binding or entry into cells for Marburg Virus," Pubchem Bioassay Record AID 540276, Jul. 2011, 13 pages, XP55641386, Retrieved from the Internet: https://pubchem.ncbi.nlm.nih.gov/bioassay/540276.

EP Search Report dated Nov. 19, 2019 from European Patent Appln. No. EP 19183201.3.

"Solvation," Wikipedia, at Internet address: https://en.wikipedia.org/wiki/Solvation, web page last edited on Mar. 13, 2019, 6 pages.

Examination Report dated Jan. 7, 2020 from Indian Patent Appln. No. 201727014547.

* cited by examiner

SUBSTITUTED INDOLE COMPOUND DERIVATIVES AS DENGUE VIRAL REPLICATION INHIBITORS

This application is a national stage application of PCT/EP2017/057662, filed Mar. 31, 2017, which claims priority benefit of Application No. EP16163482.9 filed Apr. 1, 2016. The complete disclosures of the aforementioned related patent applications are hereby incorporated herein by reference for all purposes.

The present invention relates to substituted indole compounds, methods to prevent or treat dengue viral infections by using said compounds and also relates to said compounds for use as a medicine, more preferably for use as a medicine to treat or prevent dengue viral infections. The present invention furthermore relates to pharmaceutical compositions or combination preparations of the compounds, to the compositions or preparations for use as a medicine, more preferably for the prevention or treatment of dengue viral infections. The invention also relates to processes for preparation of the compounds.

BACKGROUND OF THE INVENTION

Flaviviruses, which are transmitted by mosquitoes or ticks, cause life-threatening infections in man, such as encephalitis and hemorrhagic fever. Four distinct, but closely related serotypes of the flavivirus dengue are known, so-called DENV-1, -2, -3, and -4. Dengue is endemic in most tropical and sub-tropical regions around the world, predominantly in urban and semi-urban areas. According to the World Health Organization (WHO), 2.5 billion people of which 1 billion children are at risk of DENV infection (WHO, 2002). An estimated 50 to 100 million cases of dengue fever [DF], half a million cases of severe dengue disease (i.e. dengue hemorrhagic fever [DHF] and dengue shock syndrome [DSS]), and more than 20,000 deaths occur worldwide each year. DHF has become a leading cause of hospitalization and death amongst children in endemic regions. Altogether, dengue represents the most common cause of arboviral disease. Because of recent large outbreaks in countries situated in Latin America, South-East Asia and the Western Pacific (including Brazil, Puerto Rico, Venezuela, Cambodia, Indonesia, Vietnam, Thailand), numbers of dengue cases have risen dramatically over the past years. Not only is the number of dengue cases increasing as the disease is spreading to new areas, but the outbreaks tend to be more severe.

Although progress is being made in the development of vaccines against dengue with the availability of the Dengvaxia® vaccine, many difficulties are encountered. These include the existence of a phenomenon referred to as antibody-dependent enhancement (ADE). Recovery from an infection by one serotype provides lifelong immunity against that serotype but confers only partial and transient protection against a subsequent infection by one of the other three serotypes. Following infection with another serotype, pre-existing heterologous antibodies form complexes with the newly infecting dengue virus serotype but do not neutralize the pathogen. Instead, virus entry into cells is believed to be facilitated, resulting in uncontrolled virus replication and higher peak viral titers. In both primary and secondary infections, higher viral titers are associated with more severe dengue disease. Since maternal antibodies can easily pass on to infants by breast feeding, this might be one of the reasons that children are more affected by severe dengue disease than adults.

In locations with two or more serotypes circulating simultaneously, also referred to as hyper endemic regions, the risk of serious dengue disease is significantly higher due to an increased risk of experiencing a secondary, more severe infection. Moreover, in a situation of hyper-endemicity, the probability of the emergence of more virulent strains is increased, which in turn augments the probability of dengue hemorrhagic fever (DHF) or dengue shock syndrome. The mosquitoes that carry dengue, including *Aedes aegypti* and *Aedes albopictus* (tiger mosquito), are moving north on the globe. According to the United States (US) Centers for Disease Control and Prevention (CDC), both mosquitoes are currently omnipresent in southern Texas. The spread north of dengue-carrying mosquitoes is not confined to the US, but has also been observed in Europe.

Dengvaxia®, the dengue vaccine produced by Sanofi Pasteur was first approved in Mexico and has received in the meantime approval in more countries. Nevertheless, the vaccine leaves considerable room for improvement due to limited efficacy, especially against DENV-1 and -2, low efficacy in flavivirus-naïve subjects and the lengthy dosing schedule.

Despite these shortcomings, the vaccine is a game changer in endemic settings as it will offer protection to a large part of the population, but likely not to very young infants, who bear the largest burden of dengue. In addition, the dosing schedule and very limited efficacy in flavivirus-naïve subjects make it unsuitable and likely not worthwhile/cost-effective for travelers from non-endemic areas to dengue-endemic areas. The above mentioned shortcomings of the dengue vaccines are the reason why there is a need for a pre-exposure prophylactic dengue antiviral.

Furthermore, today, specific antiviral drugs for the treatment or prevention of dengue fever virus infection are not available. Clearly, there is still a great unmet medical need for therapeutics for the prevention or treatment of viral infections in animals, more in particular in humans and especially for viral infections caused by Flaviviruses, more in particular Dengue virus. Compounds with good anti-viral potency, no or low levels of side-effects, a broad spectrum activity against multiple Dengue virus serotypes, a low toxicity and/or good pharmacokinetic or -dynamic properties are highly needed.

WO-2010/021878 discloses 2-phenylpyrrolidine and indoline derivatives as cold menthol receptor antagonists for treatment of inflammatory and central diseases. WO-2013/045516 discloses indole and indoline derivatives for use in the treatment of dengue viral infections.

The present invention now provides compounds, substituted indole derivatives, which show high potent activity against all four (4) serotypes of the Dengue virus.

SUMMARY OF THE INVENTION

The present invention is based on the unexpected finding that at least one of the above-mentioned problems can be solved by the current compounds of the invention.

The present invention provides compounds which have been shown to possess potent antiviral activity against all four (4) serotypes currently known. The present invention furthermore demonstrates that these compounds efficiently inhibit proliferation of Dengue virus (DENY). Therefore, these compounds constitute a useful class of potent compounds that can be used in the treatment and/or prevention of viral infections in animals, mammals and humans, more specifically for the treatment and/or prevention of infections with Dengue viruses.

The present invention furthermore relates to the use of such compounds as medicines and to their use for the manufacture of medicaments for treating and/or preventing viral infections, in particular with viruses belonging to the family of the Dengue viruses in animals or mammals, more in particular in humans. The invention also relates to methods for the preparation of all such compounds and to pharmaceutical compositions comprising them in an effective amount.

The present invention also relates to a method of treatment or prevention of dengue viral infections in humans by the administration an effective amount of one or more such compounds, or a pharmaceutically acceptable salt thereof optionally in combination with one or more other medicines, like another antiviral agent, to a patient in need thereof.

One aspect of the invention is the provision of compounds of formula (Ia or Ib). Formula (Ia) is represented as follows:

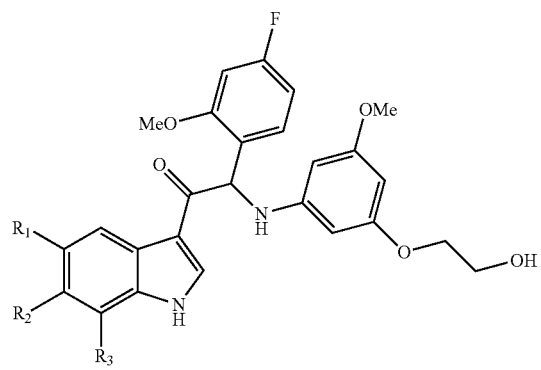

Ia a stereoisomeric form, a pharmaceutically acceptable salt, solvate or polymorph thereof comprising a mono- or di-substituted indole group; said compound is selected from the group wherein:

$R_1$ is Cl, $R_2$ is H, $R_3$ is $CH_3$;
$R_1$ is Cl, $R_2$ is $OCH_3$, $R_3$ is H;
$R_1$ is $CH_3$, $R_2$ is F or $OCF_3$ or H or $OCH_2CH_3$ and $R_3$ is H;
$R_1$ and $R_2$ are connected forming a heterocycle of 5 members having one oxygen atom, $R_3$ is H;
$R_2$ and $R_3$ are connected forming a heterocycle of 5 members having one oxygen atom, $R_1$ is H.

Formula (Ib) is represented by the following structure:

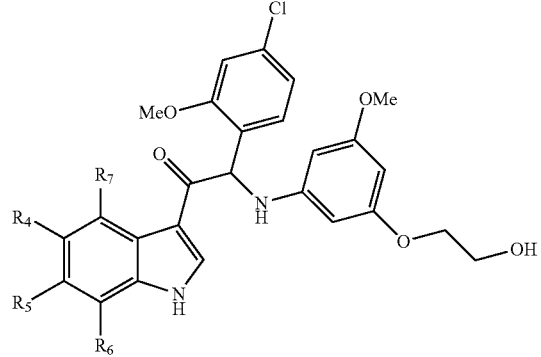

Ib a stereoisomeric form, a pharmaceutically acceptable salt, solvate or polymorph thereof comprising a mono- or di-substituted indole group; said compound is selected from the group wherein:

$R_4$ is $CH_3$, $R_5$ is F, $R_6$ and $R_7$ are both H;
$R_4$ is $CH_3$, $R_5$ is $OCH_3$, $R_6$ is H, $R_7$ is F;
$R_4$ is $SF_5$, $R_5=R_6=R_7$ are all H;
$R_4$ and $R_5$ are connected forming a heterocycle of 5 members having one oxygen atom, $R_6$ and $R_7$ are both H;
$R_5$ and $R_6$ are connected forming a heterocycle of 5 members having one oxygen atom, $R_4$ and $R_7$ are both H.

Part of the invention are also the following three compounds having the structures (II), (III) and (IV) respectively:

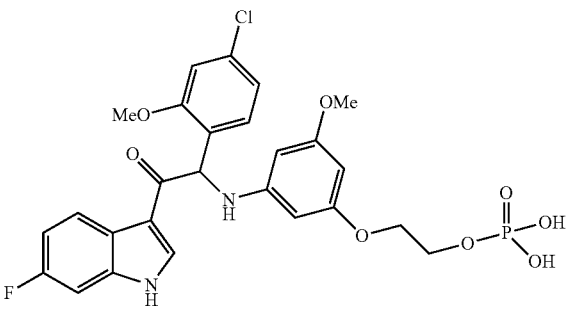

II

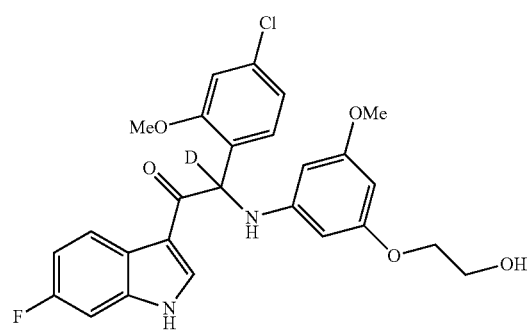

III

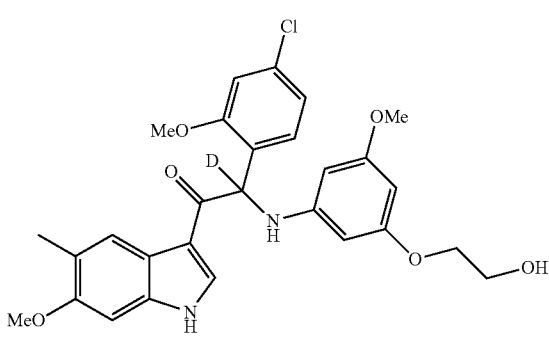

IV or a stereoisomeric form, a pharmaceutically acceptable salt, solvate or polymorph thereof.

In particular the compounds of the invention or their stereoisomeric form, a pharmaceutically acceptable salt, solvate or polymorph thereof are selected from the group:

1
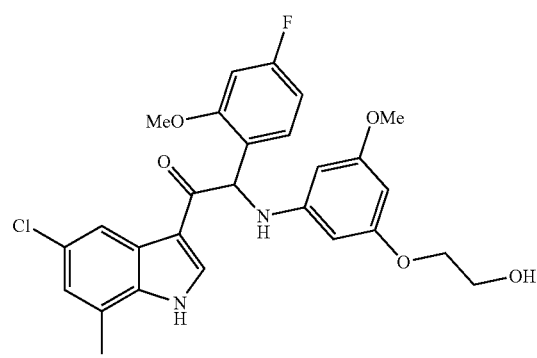
2
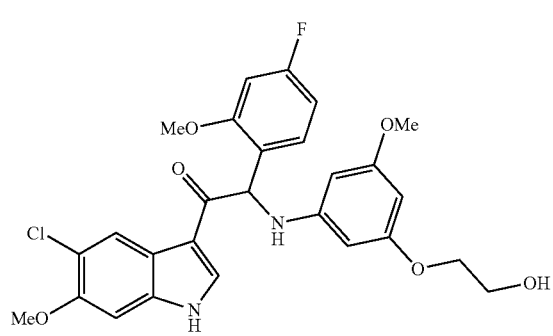
3
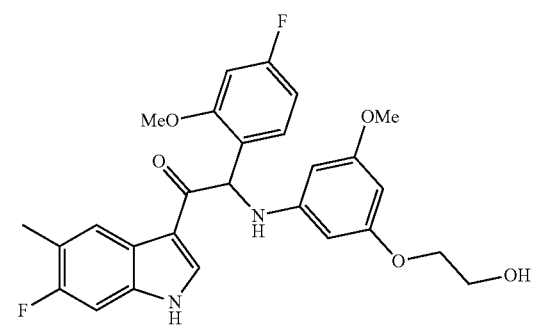
4
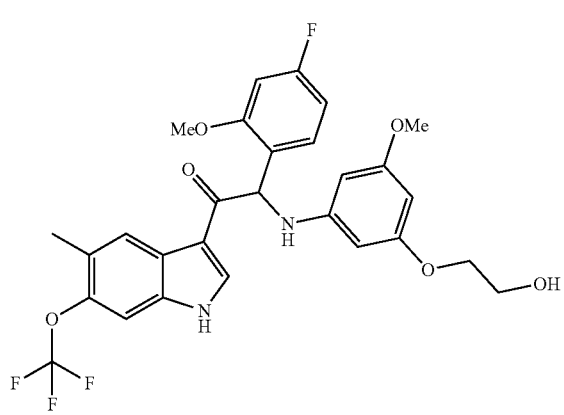
5
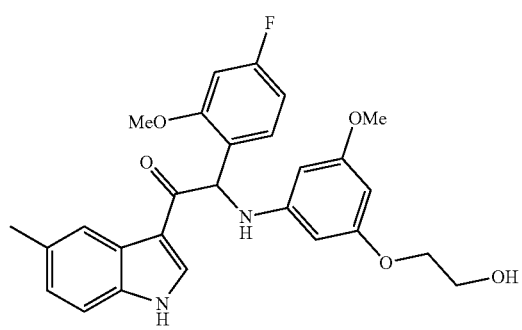
6
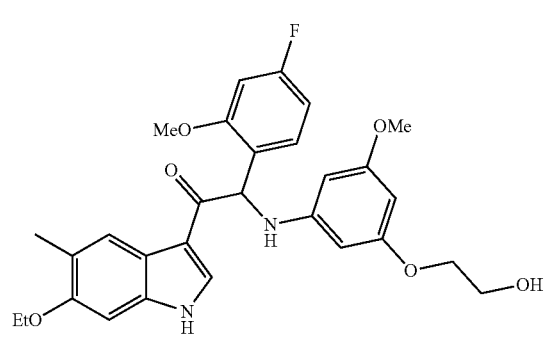
7
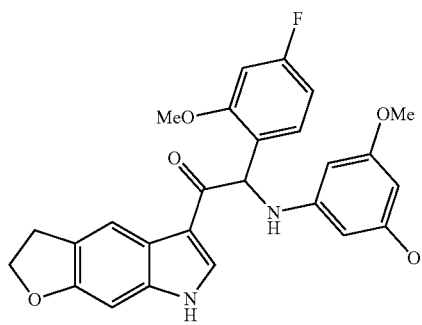
8
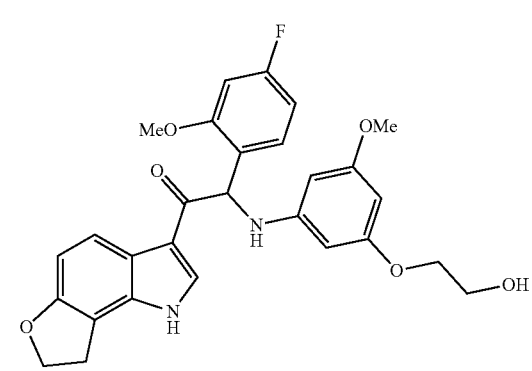

9

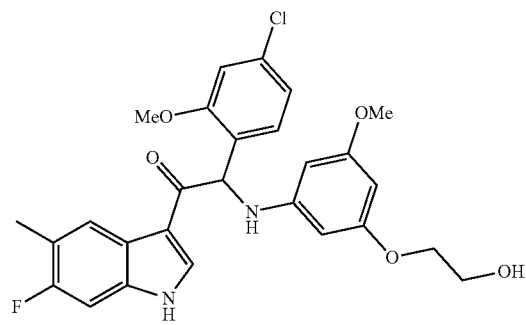

10

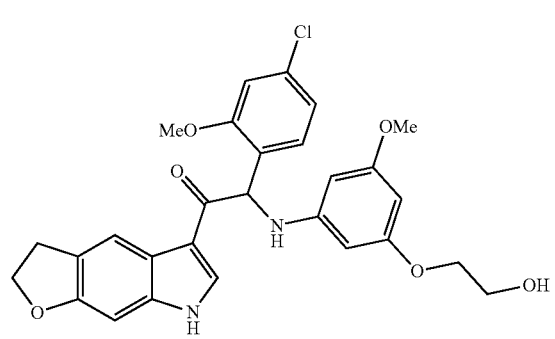

11

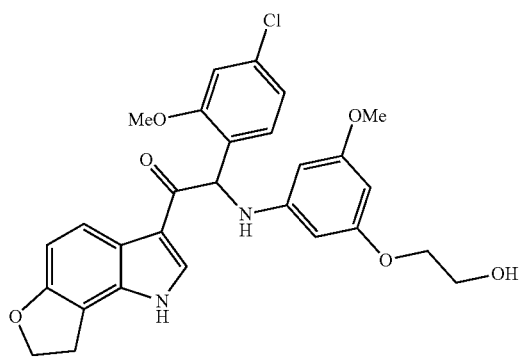

12

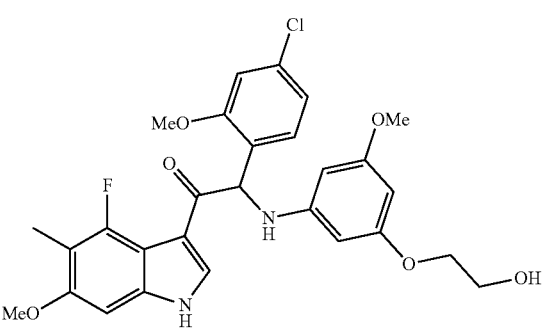

13-P

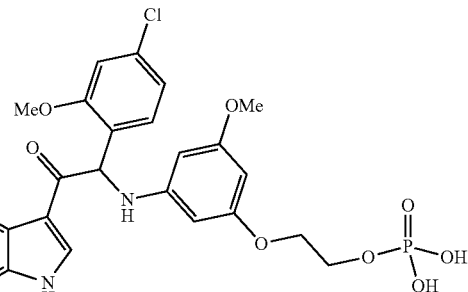

13-D

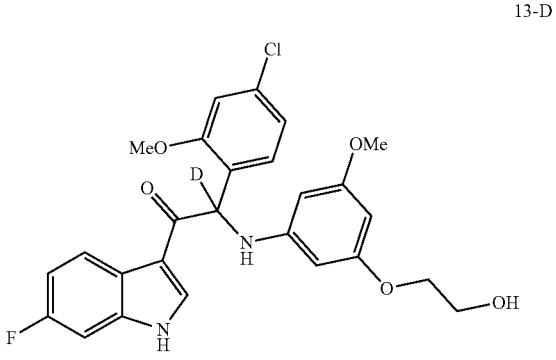

14-D

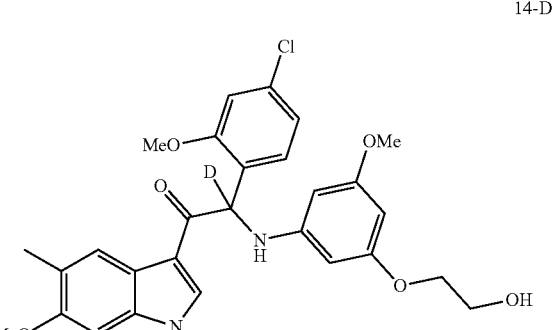

15

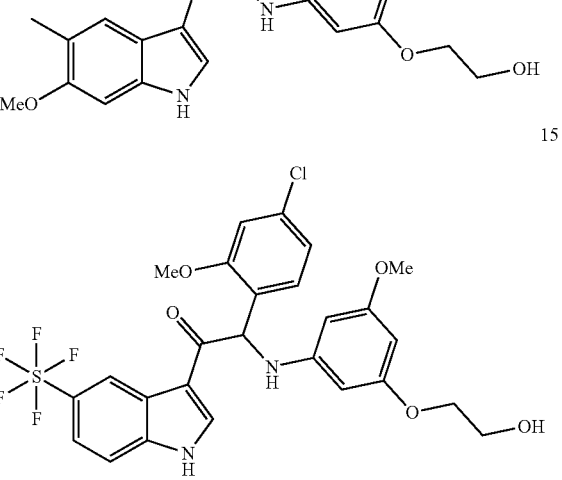

Part of the current invention is also a pharmaceutical composition comprising a compound of formula (Ia, Ib, II, III or IV) or a stereoisomeric form, a pharmaceutically acceptable salt, solvate or polymorph thereof together with one or more pharmaceutically acceptable excipients, diluents or carriers.

Pharmaceutically acceptable salts of the compounds of formula (Ia, Ib, II, III or IV) include the acid addition and base salts thereof. Suitable acid addition salts are formed from acids which form non-toxic salts. Suitable base salts are formed from bases which form non-toxic salts.

The compounds of the invention may also exist in unsolvated and solvated forms. The term "solvate" is used herein to describe a molecular complex comprising the compound of the invention and one or more pharmaceutically acceptable solvent molecules, for example, ethanol.

The term "polymorph" refers to the ability of the compound of the invention to exist in more than one form or crystal structure.

The compounds of the present invention may be administered as crystalline or amorphous products. They may be obtained for example as solid plugs, powders, or films by methods such as precipitation, crystallization, freeze drying, spray drying, or evaporative drying. They may be administered alone or in combination with one or more other compounds of the invention or in combination with one or more other drugs. Generally, they will be administered as a formulation in association with one or more pharmaceutically acceptable excipients. The term "excipient" is used herein to describe any ingredient other than the compound(s) of the invention. The choice of excipient depends largely on factors such as the particular mode of administration, the effect of the excipient on solubility and stability, and the nature of the dosage form.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, for example, for oral or rectal administration. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions, and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. Also included are solid form preparations that can be converted, shortly before use, to liquid forms.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of infectious diseases will be able to determine the effective amount from the test results presented hereinafter. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (Ia, Ib, II, III or IV) used, the particular condition being treated, the severity of the condition being treated, the age, weight and general physical condition of the particular patient as well as other medication the individual may be taking, as is well known to those skilled in the art. Furthermore, it is evident that the effective amount may be lowered or increased depending on the response of the treated subject and/or depending on the evaluation of the physician prescribing the compounds of the instant invention. The effective amount ranges mentioned above are therefore only guidelines and are not intended to limit the scope or use of the invention to any extent.

The present disclosure is also intended to include any isotopes of atoms present in the compounds of the invention. For example, isotopes of hydrogen include tritium and deuterium and isotopes of carbon include C-13 and C-14.

The present compounds used in the current invention may also exist in their stereochemically isomeric form, defining all possible compounds made up of the same atoms bonded by the same sequence of bonds but having different three-dimensional structures, which are not interchangeable. Unless otherwise mentioned or indicated, the chemical designation of compounds encompasses the mixture of all possible stereochemically isomeric forms, which said compounds might possess.

Said mixture may contain all diastereomers and/or enantiomers of the basic molecular structure of said compound. All stereochemically isomeric forms of the compounds used in the present invention either in pure form or in admixture with each other are intended to be embraced within the scope of the present invention including any racemic mixtures or racemates.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i. e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of compounds and intermediates used in this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The compounds of formula (Ia), (Ib), (II), (III) or (IV) of the present invention all have at least one chiral carbon atom as indicated in the FIGURE below by the carbon atom labelled with *:

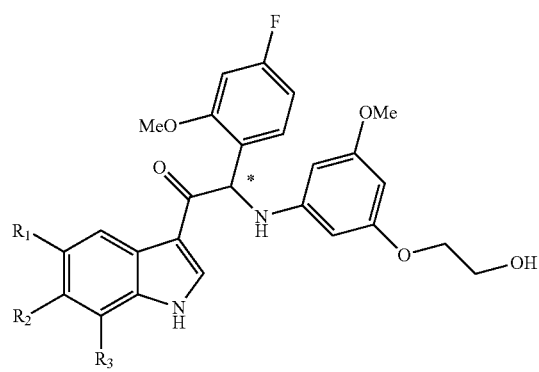

Ia

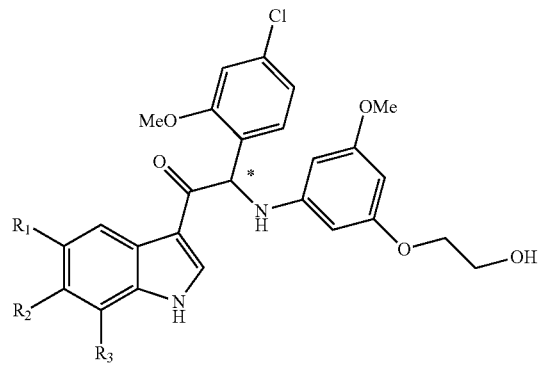

Ib

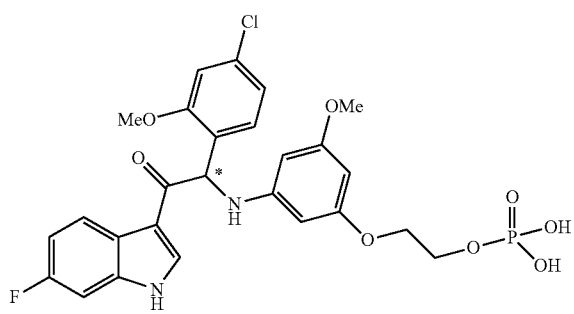

II

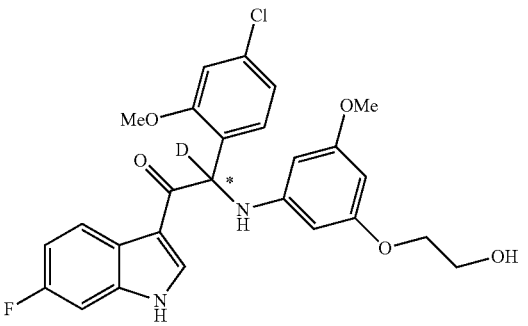

III

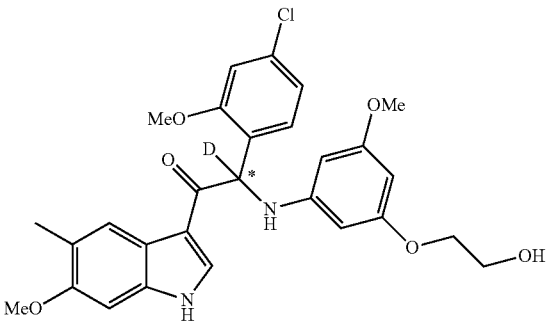

IV

Due to the presence of said chiral carbon atom, a "compound of formula (Ia), (Ib), (II), (III) or (IV)" can be the (R)-enantiomer, the (S)-enantiomer, the racemic form, or any possible combination of the two individual enantiomers in any ratio. When the absolute (R)- or (S)-configuration of an enantiomer is not known, this enantiomer can also be identified by indicating whether the enantiomer is dextrorotatory (+)- or levorotatory (−)-after measuring the specific optical rotation of said particular enantiomer.

In an aspect the present invention relates to a first group of compound of formula (Ia), (Ib), (II), (III) and (IV) wherein the compounds of formula (Ia), (Ib), (II), (III) and (IV) have the (+) specific rotation.

In a further aspect the present invention relates to a second ground of compounds of formula (Ia), (Ib), (II), (III) and (IV) wherein the compounds of formula (Ia), (Ib), (II), (III) and (IV) have the (−) specific rotation.

EXAMPLES

LC/MS Methods

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Compounds are described by their experimental retention times ($R_t$) and ions. If not specified differently in the table of data, the reported molecular ion corresponds to the $[M+H]^+$ (protonated molecule) and/or $[M-H]^-$ (deprotonated molecule). In case the compound was not directly ionizable the type of adduct is specified (i.e. [M+NH$_4$]$^+$, [M+HCOO]$^-$, etc. . . . ). For molecules with multiple isotopic patterns (Br, Cl), the reported value is the one obtained for the lowest isotope mass. All results were obtained with experimental uncertainties that are commonly associated with the method used.

Hereinafter, "SQD" means Single Quadrupole Detector, "MSD" Mass Selective Detector, "RT" room temperature, "BEH" bridged ethylsiloxane/silica hybrid, "DAD" Diode Array Detector, "HSS" High Strength silica. LC/MS Method codes (Flow expressed in mL/min; column temperature (T) in ° C.; Run time in minutes)

| Method code | Instrument | Column | Mobile phase | Gradient | Flow Col T | Run time (min) |
|---|---|---|---|---|---|---|
| LC-A | Waters: Acquity ® UPLC ®-DAD-SQD | Waters: BEH C18 (1.7 µm, 2.1 × 50 mm) | A: 10 mM CH$_3$COONH$_4$ in 95% H$_2$O + 5% CH$_3$CN B: CH$_3$CN | From 95% A to 5% A in 1.3 min, held for 0.7 min. | 0.8 mL/min 55° C. | 2 |
| LC-B | Waters: Acquity ® UPLC ®-DAD-SQD | Waters: HSS T3 (1.8 µm, 2.1 × 100 mm) | A: 10 mM CH$_3$COONH$_4$ in 95% H$_2$O + 5% CH$_3$CN B: CH$_3$CN | From 100% A to 5% A in 2.10 min, to 0% A in 0.90 min, to 5% A in 0.5 min | 0.7 mL/min 55° C. | 3.5 |
| LC-C | Waters: Acquity ® UPLC ®-DAD-Quattro Micro ™ | Waters: BEH C18 (1.7 µm, 2.1 × 100 mm) | A: 95% CH$_3$COONH$_4$ 7 mM/5% CH$_3$CN, B: CH$_3$CN | 84.2% A for 0.49 min, to 10.5% A in 2.18 min, held for 1.94 min, back to 84.2% A in 0.73 min, held for 0.73 min. | 0.343 mL/min 40° C. | 6.2 |
| LC-D | Waters: Acquity ® H-Class-DAD and SQD2 ™ | Waters: BEH C18 (1.7 µm, 2.1 × 100 mm) | A: CH$_3$COONH$_4$ 7 mM 95%/ CH$_3$CN 5%, B: CH$_3$CN | 84.2% A/15.8% B to 10.5% A in 2.18 min, held for 1.96 min, back to 84.2%A/15.8% B in 0.73 min, held for 0.49 min. | 0.343 mL/min 40° C. | 6.1 |

SFC/MS Methods

The SFC measurement was performed using an Analytical Supercritical fluid chromatography (SFC) system composed by a binary pump for delivering carbon dioxide (CO2) and modifier, an autosampler, a column oven, a diode array detector equipped with a high-pressure flow cell standing up to 400 bars. If configured with a Mass Spectrometer (MS) the flow from the column was brought to the (MS). It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Analytical SFC/MS Methods (Flow expressed in mL/min; column temperature (T) in ° C.; Run time in minutes, Backpressure (BPR) in bars.

| Method code | column | mobile phase | gradient | Flow Col T | Run time BPR |
|---|---|---|---|---|---|
| SFC-A | Daicel Chiralpak ® AS3 column (3.0 µm, 150 × 4.6 mm) | A: CO$_2$ B: EtOH +0.2% iPrNH$_2$ +3% H$_2$O | 10%-50% B in 6 min, hold 3.5 min | 2.5 40 | 9.5 110 |
| SFC-B | Daicel Chiralpak ® IA column (5 µm, 150 × 4.6 mm) | A: CO$_2$ B: EtOH/ iPrOH 50/50 (+0.3% iPrNH$_2$) | 40% B hold 7 min, | 3 35 | 7 100 |
| SFC-C | Daicel Chiralcel ® OD column (5 µm, 150 × 4.6 mm) | A: CO$_2$ B: iPrOH | 30% B hold 7 min, | 3 35 | 7 100 |
| SFC-D | Daicel Chiralcel ® OJ-H column (5 µm, 250 × 4.6 mm) | A: CO$_2$ B: MeOH | 40% B hold 7 min, | 3 35 | 7 100 |
| SFC-E | Daicel Chiralpak ® AD-H column (5 µm, 150 × 4.6 mm) | A: CO$_2$ B: MeOH | 40% B hold 7 min, | 3 35 | 7 100 |

| Method code | column | mobile phase | gradient | Flow Col T | Run time BPR |
|---|---|---|---|---|---|
| SFC-F | Daicel Chiralpak® ID3 column (3.0 μm, 150 × 4.6 mm) | A: $CO_2$<br>B: EtOH + 0.2% $iPrNH_2$ | 45% B hold 6 min, to 50% in 1 min hold 2.5 min | 2.5<br>40 | 9.5<br>110 |
| SFC-G | Daicel Chiralpak® ID3 column (3.0 μm, 150 × 4.6 mm) | A: $CO_2$<br>B: EtOH + 1% $iPrNH_2$ | 40% B hold 6 min, to 50% in 1 min hold 2.5 min | 2.5<br>40 | 9.5<br>110 |

Melting Points

Values are either peak values or melt ranges, and are obtained with experimental uncertainties that are commonly associated with this analytical method.

DSC823e (Indicated as DSC)

For a number of compounds, melting points were determined with a DSC823e (Mettler-Toledo). Melting points were measured with a temperature gradient of 10° C./minute. Maximum temperature was 300° C.

Optical Rotations

Optical rotations were measured on a Perkin-Elmer 341 polarimeter with a sodium lamp and reported as follows: $[\alpha]^0$ ($\lambda$, c g/100 ml, solvent, T° C.). $[\alpha]_\lambda^T = (100\alpha)/(l \times c)$: where l is the path length in dm and c is the concentration in g/100 ml for a sample at a temperature T (° C.) and a wavelength $\lambda$ (in nm). If the wavelength of light used is 589 nm (the sodium D line), then the symbol D might be used instead. The sign of the rotation (+ or -) should always be given. When using this equation the concentration and solvent are always provided in parentheses after the rotation. The rotation is reported using degrees and no units of concentration are given (it is assumed to be g/100 ml).

Example 1: synthesis 1-(5-chloro-7-methyl-1H-indol-3-yl)-2-(4-fluoro-2-methoxyphenyl)-2-((3-(2-hydroxyethoxy)-5-methoxyphenyl)amino)ethanone (Compound 1) and chiral separation into Enantiomers 1A and 1B

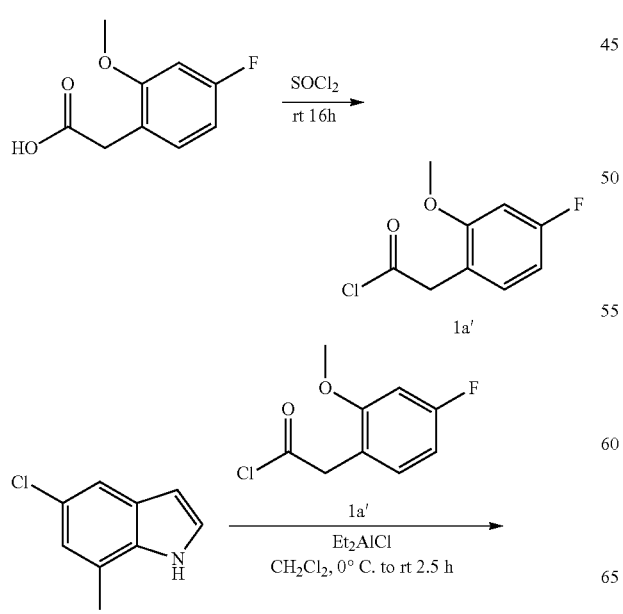

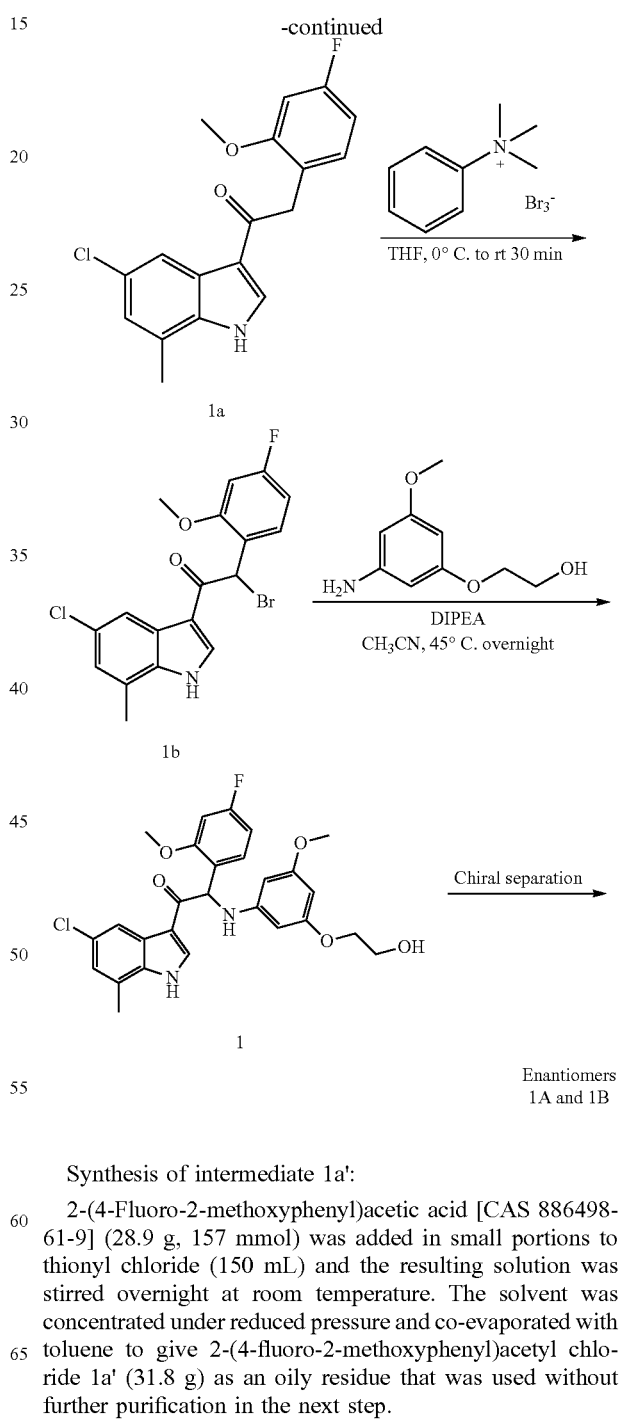

Synthesis of intermediate 1a':

2-(4-Fluoro-2-methoxyphenyl)acetic acid [CAS 886498-61-9] (28.9 g, 157 mmol) was added in small portions to thionyl chloride (150 mL) and the resulting solution was stirred overnight at room temperature. The solvent was concentrated under reduced pressure and co-evaporated with toluene to give 2-(4-fluoro-2-methoxyphenyl)acetyl chloride 1a' (31.8 g) as an oily residue that was used without further purification in the next step.

Synthesis of Intermediate 1a:

A solution of 5-chloro-7-methyl-1H-indole [CAS 15936-77-3] (5.9 g, 35.6 mmol) in $CH_2Cl_2$ (150 mL) was cooled to 0° C. under $N_2$-atmosphere. A solution of diethylaluminum chloride 1M in hexane (53.4 mL, 53.4 mmol) was added dropwise over 10 min and the resulting mixture was kept at 0° C. for 15 min. A solution of 2-(4-fluoro-2-methoxyphenyl)acetyl chloride 1a' (10.8 g, 53.4 mmol) in $CH_2Cl_2$ (100 mL) was added dropwise over 100 min. Stirring was continued at 0° C. for 15 min and at room temperature for 2.5 h. The reaction mixture was cooled again to 0° C. and the reaction was quenched by the slow addition of a solution of potassium sodium tartrate tetrahydrate (Rochelle salt) [CAS 6100-16-9] (20.1 g, 71.2 mmol) in water (21 mL). Stirring was continued at 0° C. for 20 min. THF (350 mL) was added and the mixture was allowed to warm to room temperature. $Na_2SO_4$ (50 g) was added and after overnight stirring, the mixture was filtered over Dicalite® and the filter cake was washed with THF (4×250 mL). The filtrates were combined and evaporated under reduced pressure. The residue was stirred up in $CH_3CN$ (30 mL) at 50° C. and the resulting precipitate was filtered off, washed with $CH_3CN$ (4×) and dried under vacuum at 50° C. to provide 1-(5-chloro-7-methyl-1H-indol-3-yl)-2-(4-fluoro-2-methoxyphenyl)ethanone 1a (3.54 g). The filtrate was concentrated under vacuum and co-evaporated with EtOAc. The residue was stirred up in $CH_2Cl_2$ (10 mL). The solids were isolated by filtration, washed with $CH_2Cl_2$ (5×) and dried under vacuum at 50° C. to provide a second crop of 1a (1.46 mg).

Synthesis of Intermediate 1b:

A stirred solution of 1-(5-chloro-7-methyl-1H-indol-3-yl)-2-(4-fluoro-2-methoxyphenyl)ethanone 1a (1.46 g, 4.40 mmol) in THF (40 mL) was cooled to 0° C. under $N_2$-atmosphere. Phenyltrimethylammonium tribromide [CAS 4207-56-1] (1.74 g, 4.62 mmol) was added and the resulting suspension was stirred at 0° C. for 30 min and at room temperature for 30 min. The solids were removed by filtration and washed with THF (2×). The combined filtrates were evaporated under reduced pressure to provide 2-bromo-1-(5-chloro-7-methyl-1H-indol-3-yl)-2-(4-fluoro-2-methoxyphenyl)ethanone 1b (1.81 g), which was used without further purification in the next step.

Synthesis of Compound 1 and Chiral Separation of Enantiomers 1A and 1B:

A mixture of 2-bromo-1-(5-chloro-7-methyl-1H-indol-3-yl)-2-(4-fluoro-2-methoxyphenyl)ethanone 1b (1.81 g, 4.40 mmol), 2-(3-amino-5-methoxyphenoxy)ethanol [CAS 725237-16-1] (2.42 g, 13.2 mmol) and diisopropylethylamine (0.76 mL, 4.40 mmol) in $CH_3CN$ (50 mL) was stirred at room temperature overnight. More diisopropylethylamine (0.76 mL, 4.40 mmol) was added and the reaction mixture was heated at 45° C. for 24 h. The reaction mixture was poured out into water (200 mL) and the product was extracted with EtOAc (2×). The combined extracts were washed with brine, dried over $MgSO_4$, filtered and evaporated under reduced pressure. The residue was purified by flash chromatography (Stationary phase: Grace Reveleris® silica 80 g, Mobile phase: heptane/EtOAc/EtOH gradient 100/0/0 to 40/45/15). The desired fractions were combined and evaporated under reduced pressure. The residue was further purified via preparative HPLC (Stationary phase: Uptisphere® C18 ODB—10 μm, 200 g, 5 cm, Mobile phase: 0.25% $NH_4HCO_3$ solution in water, $CH_3CN$). The desired fractions were combined and evaporated under reduced pressure. The residue was stirred up in MeOH (10 mL) at 45° C. The solids were filtered off, washed with MeOH (4×2.5 mL) and dried under vacuum at 50° C. to give 1-(5-chloro-7-methyl-1H-indol-3-yl)-2-(4-fluoro-2-methoxyphenyl)-2-((3-(2-hydroxyethoxy)-5-methoxyphenyl)amino)ethanone (Compound 1, 1.07 g) as a racemic mixture.

The enantiomers of Compound 1 (1.02 g) were separated via normal phase chiral separation (Stationary phase: (5,5)-Whelk-O1, Mobile phase: 70% heptane, 30% ethanol). The product fractions were combined and evaporated to provide Enantiomer 1A as the first eluted product and Enantiomer 1B as the second eluted product. Enantiomer 1A was purified by flash chromatography (Stationary phase: Grace Reveleris® silica 12 g, Mobile phase: heptane/EtOAc/EtOH gradient 100/0/0 to 40/45/15). The desired fractions were combined and evaporated under reduced pressure. The residue was stirred up in heptane (2 mL) and EtOAc (0.2 mL) was added dropwise. The mixture was stirred for 10 min, the solids were filtered off, washed (4×) with a mixture of heptane/EtOAc (9/1), and dried at under vacuum at 50° C. to provide Enantiomer 1A (314 mg). Enantiomer 1B was crystallized from $CH_2Cl_2$ (2.5 mL). The solids were filtered off, washed (4×) with a small amount of $CH_2Cl_2$, and dried under vacuum at 50° C. to provide Enantiomer 1B (204 mg).

Compound 1:

$^1H$ NMR (400 MHz, DMSO-$d_6$) δ ppm 2.46 (s, 3H) 3.61 (s, 3H) 3.64 (q, J=5.4 Hz, 2H) 3.83 (qt, J=10.1, 5.1 Hz, 2H) 3.96 (s, 3H) 4.77 (t, J=5.5 Hz, 1H) 5.71 (t, J=2.1 Hz, 1H) 5.95 (d, J=2.0 Hz, 2H) 6.15 (d, J=8.1 Hz, 1H) 6.33 (d, J=7.9 Hz, 1H) 6.72 (td, J=8.5, 2.4 Hz, 1H) 6.92 (dd, J=11.4, 2.4 Hz, 1H) 7.07 (d, J=1.1 Hz, 1H) 7.37 (dd, J=8.5, 6.9 Hz, 1H) 7.97 (d, J=1.5 Hz, 1H) 8.44 (s, 1H) 12.26 (br s, 1H)

LC/MS (method LC-A): $R_t$ 1.17 min, $MH^+$ 513

Enantiomer 1A:

$^1H$ NMR (400 MHz, DMSO-$d_6$) δ ppm 2.46 (s, 3H) 3.61 (s, 3H) 3.64 (q, J=5.4 Hz, 2H) 3.74-3.90 (m, 2H) 3.96 (s, 3H) 4.77 (t, J=5.5 Hz, 1H) 5.71 (t, J=2.1 Hz, 1H) 5.95 (d, J=2.2 Hz, 2H) 6.15 (d, J=7.9 Hz, 1H) 6.34 (d, J=7.9 Hz, 1H) 6.72 (td, J=8.5, 2.4 Hz, 1H) 6.92 (dd, J=11.4, 2.4 Hz, 1H) 7.07 (d, J=1.1 Hz, 1H) 7.37 (dd, J=8.6, 7.0 Hz, 1H) 7.97 (d, J=2.0 Hz, 1H) 8.44 (s, 1H) 12.26 (s, 1H)

LC/MS (method LC-A): $R_t$ 1.23 min, $MH^+$ 513

$[\alpha]_D^{20}$: +107.2° (c 0.43, DMF)

Chiral SFC (method SFC-A): $R_t$ 3.73 min, $MH^+$ 513, chiral purity 100%.

Enantiomer 1B:

$^1H$ NMR (400 MHz, DMSO-$d_6$) δ ppm 2.47 (s, 3H) 3.61 (s, 3H) 3.65 (q, J=5.1 Hz, 2H) 3.77-3.90 (m, 2H) 3.96 (s, 3H) 4.77 (t, J=5.5 Hz, 1H) 5.72 (t, J=2.1 Hz, 1H) 5.95 (d, J=2.0 Hz, 2H) 6.16 (d, J=7.9 Hz, 1H) 6.34 (d, J=7.9 Hz, 1H) 6.73 (td, J=8.5, 2.4 Hz, 1H) 6.93 (dd, J=11.3, 2.5 Hz, 1H) 7.07 (dd, J=1.9, 0.8 Hz, 1H) 7.37 (dd, J=8.6, 6.8 Hz, 1H) 7.97 (d, J=1.5 Hz, 1H) 8.45 (s, 1H) 12.26 (br s, 1H) LC/MS (method LC-A): $R_t$ 1.26 min, $MH^+$ 513

$[\alpha]_D^{20}$: −107.5° (c 0.51, DMF)

Chiral SFC (method SFC-A): $R_t$ 4.34 min, $MH^+$ 513, chiral purity 100%.

Melting point: 118° C.

Example 2: Synthesis 1-(5-chloro-6-methoxy-1H-indol-3-yl)-2-(4-fluoro-2-methoxyphenyl)-2-((3-(2-hydroxyethoxy)-5-methoxyphenyl)amino)ethanone (Compound 2) and chiral separation into Enantiomers 2A and 2B

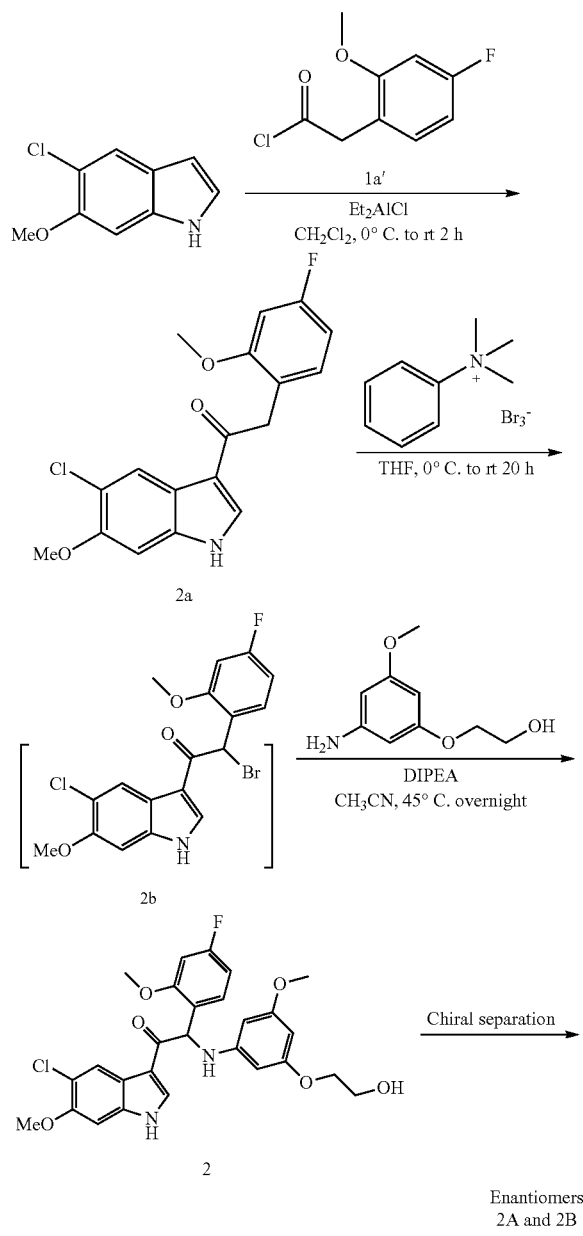

Synthesis of Intermediate 2a:

A solution of 5-chloro-6-methoxy-1H-indole [CAS 90721-60-1] (5.0 g, 27.5 mmol) in CH$_2$Cl$_2$ (100 mL) was cooled to 0° C. under N$_2$-atmosphere. A solution of diethylaluminum chloride 1M in hexane (41.3 mL, 41.3 mmol) was added dropwise over 10 min and the resulting mixture was kept at 0° C. for 20 min. A solution of 2-(4-fluoro-2-methoxyphenyl)acetyl chloride 1a' (8.37 g, 41.3 mmol) in CH$_2$Cl$_2$ (100 mL) was added dropwise over 70 min. Stirring was continued at 0° C. for 1.5 h min and at room temperature for 2 h. The reaction mixture was cooled again to 0° C. and the reaction was quenched by the slow addition of a solution of potassium sodium tartrate tetrahydrate (Rochelle salt) [CAS 6100-16-9] (15.5 g, 55.1 mmol) in water (16 mL). Stirring was continued at 0° C. for 30 min and at room temperature for 1 h. THF (200 mL) and Na$_2$SO$_4$ (50 g) were added and after overnight stirring, the mixture was filtered over Dicalite® and the filter cake was washed with 2-methyl-THF (5×200 mL) and with THF (2 L). The THF filtrates were combined and evaporated under reduced pressure to a residual volume of 30 mL. The resulting precipitate was filtered off, washed with THF (2×3 mL) and dried under vacuum at 50° C. to provide a first fraction of 1-(5-chloro-6-methoxy-1H-indol-3-yl)-2-(4-fluoro-2-methoxyphenyl)ethanone 2a (1.73 g). The filtrate was combined with the earlier obtained 2-methyl-THF filtrates and concentrated under reduced pressure. The residue (2.8 g) was stirred up in CH$_2$Cl$_2$ (7 mL). The resulting precipitate was filtered off, washed with CH$_2$Cl$_2$ (4×1 mL) and dried under vacuum at 50° C. to provide a second fraction of 2a (1.65 g).

Synthesis of Compound 2 and Chiral Separation of Enantiomers 2A and 2B:

A stirred solution of 1-(5-chloro-6-methoxy-1H-indol-3-yl)-2-(4-fluoro-2-methoxyphenyl)ethanone 2a (1.73 g, 4.98 mmol) in THF (75 mL) was cooled to 0° C. under N$_2$-atmosphere. Phenyltrimethylammonium tribromide [CAS 4207-56-1] (1.96 g, 5.22 mmol) was added and the resulting suspension was stirred at 0° C. for 100 min and at room temperature for 20 h. 2-(3-Amino-5-methoxyphenoxy)ethanol [CAS 725237-16-1] (2.73 g, 14.9 mmol) was added and the solvents were evaporated under reduced pressure. The residue was dissolved in CH$_3$CN (100 mL), diisopropylethylamine (1.72 mL, 9.95 mmol) was added and the reaction mixture was stirred at room temperature for 8 h and at 45° C. for 16 h. The reaction mixture was poured out into water (400 mL) and the product was extracted with 2-methyl-THF (2×). The combined extracts were washed with brine, dried over MgSO$_4$, filtered and evaporated under reduced pressure. The residue was purified by flash chromatography (Stationary phase: Grace Reveleris® silica 12 g, Mobile phase: CH$_2$Cl$_2$/MeOH gradient 100/0 to 98/2). The desired fractions were combined, evaporated under reduced pressure and co-evaporated with MeOH. The residue was further purified via preparative HPLC (Stationary phase: RP XBridge® Prep C18 OBD-10 µm, 30×150 mm, Mobile phase: 0.25% NH$_4$HCO$_3$ solution in water, MeOH). The desired fractions were combined, evaporated under reduced pressure and co-evaporated with MeOH. The residue was further purified via preparative HPLC (Stationary phase: Uptisphere® C18 ODB—10 µm, 200 g, 5 cm, Mobile phase: 0.25% NH$_4$HCO$_3$ solution in water, CH$_3$CN). The desired fractions were combined, evaporated under reduced pressure and co-evaporated with MeOH. The residue was stirred up in MeOH (20 mL) at 50° C. The solids were filtered off, washed with MeOH (3×5 mL) and dried under vacuum at 50° C. to give 1-(5-chloro-6-methoxy-1H-indol-3-yl)-2-(4-fluoro-2-methoxyphenyl)-2-((3-(2-hydroxyethoxy)-5-methoxyphenyl)amino)ethanone (Compound 2, 1.43 g) as a racemic mixture.

The enantiomers of Compound 2 (1.36 g) were separated via normal phase chiral separation (Stationary phase: (S,S)-Whelk-01, Mobile phase: 100% methanol). The product fractions were combined and evaporated to provide Enantiomer 2A as the first eluted product and Enantiomer 2B as the second eluted product. Enantiomer 2A was stirred up in MeOH at 45° C. (10 mL), filtered off, washed (4×) with MeOH and dried at under vacuum at 50° C. to provide Enantiomer 2A (392 mg). Enantiomer 2B was stirred up in MeOH at 45° C. (7.5 mL), filtered off, washed (4×) with MeOH and dried at under vacuum at 50° C. to provide Enantiomer 2B (286 mg).

Compound 2:

¹H NMR (400 MHz, DMSO-d₆) δ ppm 3.61 (s, 3H) 3.64 (q, J=5.2 Hz, 2H) 3.76-3.89 (m, 5H) 3.95 (s, 3H) 4.77 (t, J=5.5 Hz, 1H) 5.72 (t, J=2.0 Hz, 1H) 5.93 (d, J=2.0 Hz, 2H) 6.11 (d, J=8.1 Hz, 1H) 6.33 (d, J=8.1 Hz, 1H) 6.73 (td, J=8.5, 2.4 Hz, 1H) 6.93 (dd, J=11.3, 2.5 Hz, 1H) 7.14 (s, 1H) 7.37 (dd, J=8.6, 6.8 Hz, 1H) 8.11 (s, 1H) 8.34 (s, 1H) 11.95 (s, 1H)

LC/MS (method LC-A): $R_t$ 1.12 min, MH⁺ 529

Enantiomer 2A:

¹H NMR (400 MHz, DMSO-d₆) δ ppm 3.61 (s, 3H) 3.64 (q, J=5.0 Hz, 2H) 3.76-3.89 (m, 5H) 3.95 (s, 3H) 4.77 (br t, J=5.3 Hz, 1H) 5.71 (t, J=2.0 Hz, 1H) 5.93 (d, J=2.0 Hz, 2H) 6.11 (d, J=8.1 Hz, 1H) 6.33 (d, J=7.9 Hz, 1H) 6.73 (td, J=8.5, 2.4 Hz, 1H) 6.92 (dd, J=11.3, 2.5 Hz, 1H) 7.13 (s, 1H) 7.37 (dd, J=8.6, 6.8 Hz, 1H) 8.11 (s, 1H) 8.34 (s, 1H) 11.95 (br s, 1H)

LC/MS (method LC-B): $R_t$ 1.99 min, MH⁺ 529

$[\alpha]_D^{20}$: +114.4° (c 0.52, DMF)

Chiral SFC (method SFC-A): $R_t$ 3.99 min, MH⁺ 529, chiral purity 100%.

Melting point: 207° C.

Enantiomer 2B:

¹H NMR (400 MHz, DMSO-d₆) δ ppm 3.61 (s, 3H) 3.64 (q, J=5.3 Hz, 2H) 3.75-3.90 (m, 5H) 3.95 (s, 3H) 4.77 (t, J=5.5 Hz, 1H) 5.71 (t, J=2.1 Hz, 1H) 5.93 (d, J=2.0 Hz, 2H) 6.11 (d, J=8.1 Hz, 1H) 6.33 (d, J=8.1 Hz, 1H) 6.72 (td, J=8.5, 2.6 Hz, 1H) 6.92 (dd, J=11.3, 2.5 Hz, 1H) 7.13 (s, 1H) 7.36 (dd, J=8.6, 6.8 Hz, 1H) 8.11 (s, 1H) 8.34 (s, 1H) 11.95 (s, 1H)

LC/MS (method LC-B): $R_t$ 1.99 min, MH⁺ 529

$[\alpha]_D^{20}$: −114.1° (c 0.51, DMF)

Chiral SFC (method SFC-A): $R_t$ 4.35 min, MH⁺ 529, chiral purity 100%.

Melting point: 210° C.

Example 3: Synthesis of 2-(4-fluoro-2-methoxyphenyl)-1-(6-fluoro-5-methyl-1H-indol-3-yl)-2-((3-(2-hydroxyethoxy)-5-methoxyphenyl)amino)ethanone (Compound 3) and chiral separation into Enantiomers 3A and 3B

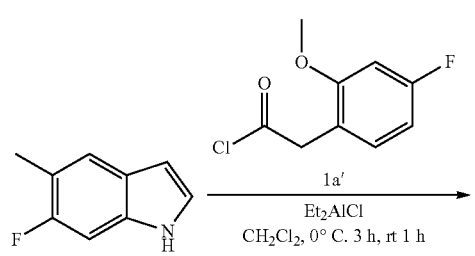

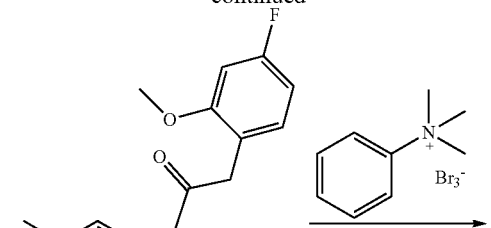

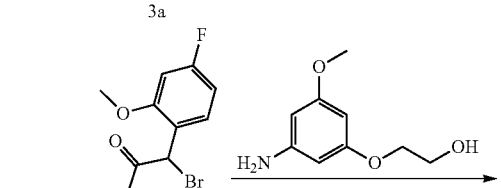

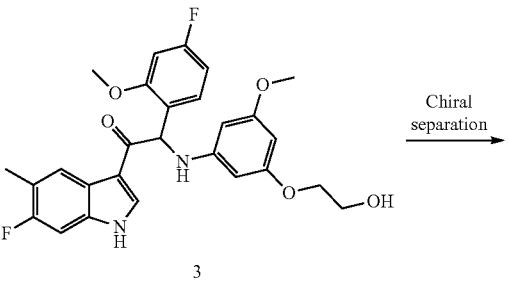

Synthesis of Intermediate 3a:

Diethylaluminium chloride 1M in hexane (15 mL, 15.1 mmol) was added dropwise at 0° C. to a solution of 6-fluoro-5-methyl-1H-indole [CAS 162100-95-0] (1.5 g, 10.6 mmol) in CH₂Cl₂ (30 mL). After 30 min at 0° C., 2-(4-fluoro-2-methoxyphenyl)acetyl chloride 1a' (3.05 g, 15.1 mmol, synthesis: see Example 1) in CH₂Cl₂ (20 mL) was added slowly at 0° C. The reaction was stirred at 0° C. for 3 h and then at room temperature for 1 h. Ice-water was added. The precipitate was filtered off, washed with water and dried under vacuum to afford 2-(4-fluoro-2-methoxyphenyl)-1-(6-fluoro-5-methyl-1H-indol-3-yl)ethanone 3a (2.27 g).

Synthesis of Intermediate 3b:

At 0° C., a solution of phenyltrimethylammonium tribromide [CAS 4207-56-1] (1.79 g, 4.76 mmol) in THF (15 mL) was added dropwise to a mixture of 2-(4-fluoro-2-methoxyphenyl)-1-(6-fluoro-5-methyl-1H-indol-3-yl)ethanone 3a (1.5 g, 4.76 mmol) in THF (15 mL). The mixture was stirred at 0° C. for 1 h and at room temperature for 4 h. The precipitate was filtered off and washed with EtOAc. The filtrate was concentrated under reduced pressure. The residue was taken up with EtOAc, washed with water, dried over MgSO₄, filtered, and the solvent was evaporated under reduced pressure. The residue was taken up with a minimum amount of EtOAc. The precipitate was filtered off and dried under vacuum to give 2-bromo-2-(4-fluoro-2-methoxyphenyl)-1-(6-fluoro-5-methyl-1H-indol-3-yl)ethanone 3b (1.3 g). The filtrate was concentrated under reduced pressure to give a second batch of 3b (1 g). The two batches were used as such in the next step.

Synthesis of Compound 3 and Chiral Separation into Enantiomers 3A and 3B:

A mixture of 2-bromo-2-(4-fluoro-2-methoxyphenyl)-1-(6-fluoro-5-methyl-1H-indol-3-yl)ethanone 3b (1.3 g, 3.3 mmol), 2-(3-amino-5-methoxyphenoxy)ethanol [CAS 725237-16-1] (906 mg, 4.95 mmol) and diisopropylethylamine (852 μL, 4.95 mmol) in THF (14 mL) and CH$_3$CN (14 mL) was stirred at 50° C. for 12 h. The solution was concentrated under reduced pressure. The residue was taken up with EtOAc. The organic layer was washed with water and HCl (1N) (twice), separated, dried over MgSO$_4$, filtered and the solvent was evaporated under reduced pressure. The crude residue (2 g) was combined with another batch of crude Compound 3 (3.5 g in total) and purified by column chromatography on silica gel (15-40 μm, 80 g in CH$_2$Cl$_2$/MeOH/NH$_4$OH (99/1/0.1)). The fractions containing Compound 3 were combined and the solvent was evaporated under reduced pressure. The compound was crystallized from a solution in Et$_2$O containing a few drops of CH$_3$CN. The precipitate was filtered off and dried to give 2-(4-fluoro-2-methoxyphenyl)-1-(6-fluoro-5-methyl-1H-indol-3-yl)-2-((3-(2-hydroxyethoxy)-5-methoxyphenyl)amino)ethanone (Compound 3, 1.2 g) as a racemic mixture. The Enantiomers of Compound 3 were separated via Preparative Chiral SFC (Stationary phase: Chiralpak® IA 5 μm 250×20 mm, Mobile phase: 60% CO$_2$, 40% mixture of EtOH/iPrOH 50/50 (+0.3% iPrNH$_2$) to give 518 mg of the first eluted enantiomer and 500 mg of the second eluted enantiomer. The first eluted enantiomer was crystallized from Et$_2$O to afford Enantiomer 3A (409 mg). The second eluted enantiomer was crystallized from Et$_2$O (with a few drops of CH$_3$CN) to afford Enantiomer 3B (404 mg).

Compound 3:
$^1$H NMR (500 MHz, DMSO-d$_6$) δ ppm 2.23 (d, J=1.3 Hz, 3H) 3.54 (s, 3H) 3.57 (q, J=4.7 Hz, 2H) 3.70-3.82 (m, 2H) 3.88 (s, 3H) 4.72 (br t, J=5.0 Hz, 1H) 5.64 (t, J=2.0 Hz, 1H) 5.86 (d, J=2.2 Hz, 2H) 6.05 (d, J=7.9 Hz, 1H) 6.26 (d, J=7.9 Hz, 1H) 6.65 (td, J=8.5, 2.5 Hz, 1H) 6.85 (dd, J=11.3, 2.2 Hz, 1H) 7.15 (d, J=10.1 Hz, 1H) 7.29 (dd, J=8.5, 6.9 Hz, 1H) 7.94 (d, J=7.9 Hz, 1H) 8.29 (s, 1H) 11.88 (br s, 1H)

LC/MS (method LC-C): R$_t$ 2.96 min, MH$^+$ 497

Melting point: 146° C.

Enantiomer 3A:
$^1$H NMR (500 MHz, DMSO-d$_6$) δ ppm 2.30 (s, 3H) 3.60 (s, 3H) 3.64 (q, J=5.0 Hz, 2H) 3.77-3.88 (m, 2H) 3.95 (s, 3H) 4.79 (t, J=5.5 Hz, 1H) 5.71 (s, 1H) 5.93 (d, J=1.6 Hz, 2H) 6.12 (d, J=7.9 Hz, 1H) 6.33 (d, J=7.9 Hz, 1H) 6.72 (td, J=8.4, 2.2 Hz, 1H) 6.92 (dd, J=11.2, 2.0 Hz, 1H) 7.21 (d, J=10.1 Hz, 1H) 7.33-7.38 (m, 1H) 8.01 (d, J=7.6 Hz, 1H) 8.36 (s, 1H) 11.95 (br s, 1H)

LC/MS (method LC-C): R$_t$ 2.96 min, MH$^+$ 497

[α]$_D^{20}$: +122.8° (c 0.329, DMF)

Chiral SFC (method SFC-B): R$_t$ 2.82 min, MH$^+$ 497, chiral purity 100%.

Melting point: 197° C.

Enantiomer 3B:
$^1$H NMR (500 MHz, DMSO-d$_6$) δ ppm 2.30 (s, 3H) 3.61 (s, 3H) 3.64 (q, J=5.0 Hz, 2H) 3.77-3.89 (m, 2H) 3.95 (s, 3H) 4.79 (t, J=5.5 Hz, 1H) 5.71 (t, J=1.9 Hz, 1H) 5.93 (d, J=1.9 Hz, 2H) 6.12 (d, J=8.2 Hz, 1H) 6.33 (d, J=7.9 Hz, 1H) 6.72 (td, J=8.4, 2.4 Hz, 1H) 6.92 (dd, J=11.2, 2.4 Hz, 1H) 7.22 (d, J=10.4 Hz, 1H) 7.36 (dd, J=8.5, 6.9 Hz, 1H) 8.01 (d, J=7.9 Hz, 1H) 8.36 (s, 1H) 11.94 (br s, 1H)

LC/MS (method LC-C): R$_t$ 2.96 min, MH$^+$ 497

[α]$_D^{20}$: −121.53° (c 0.288, DMF)

Chiral SFC (method SFC-B): R$_t$ 3.67 min, MH$^+$ 497, chiral purity 99.73%.

Melting point: 197° C.

Example 4: Synthesis of 2-(4-fluoro-2-methoxyphenyl)-2-((3-(2-hydroxyethoxy)-5-methoxyphenyl)amino)-1-(5-methyl-6-(trifluoromethoxy)-1H-indol-3-yl)ethanone (Compound 4) and chiral separation into Enantiomers 4A and 4B

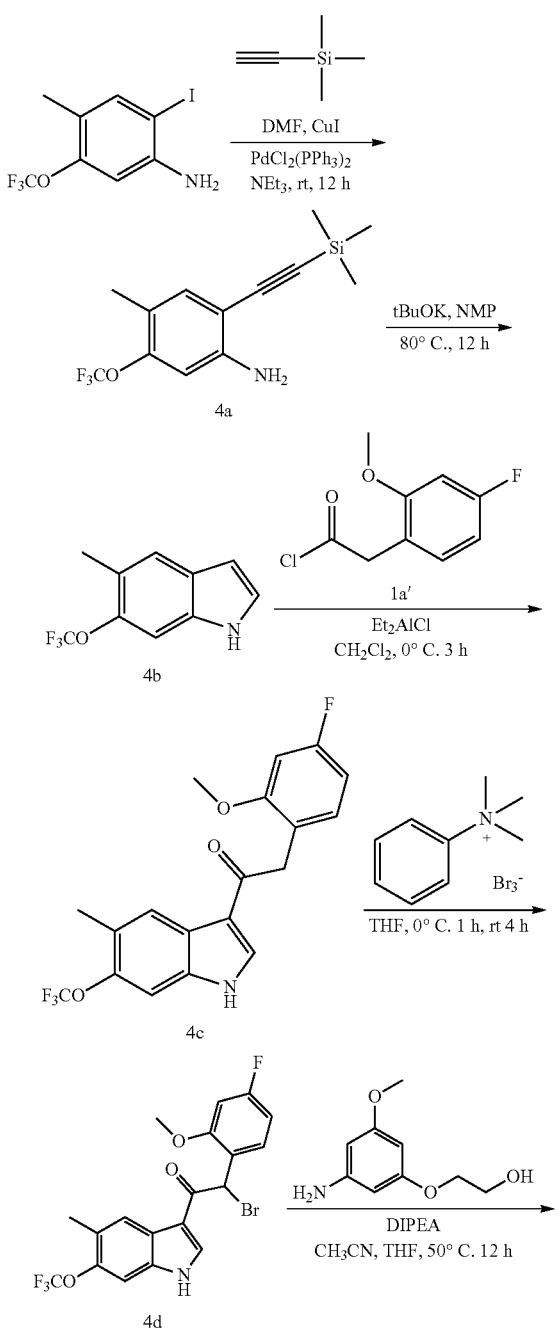

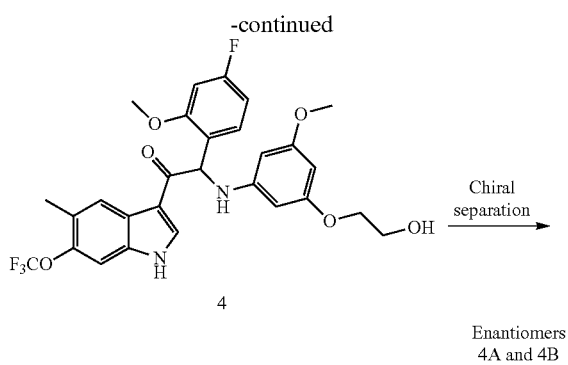

Synthesis of Intermediate 4a:

To a mixture of 2-iodo-4-methyl-5-(trifluoromethoxy)aniline [CAS 851045-65-3] in DMF (25 mL) under $N_2$-flow at 15° C. was added copper(I) iodide (247 mg, 1.3 mmol), triethyamine (2.71 mL, 19.5 mmol), $PdCl_2(PPh_3)_2$ (456 mg, 0.65 mmol) and trimethylsilylacetylene (2.70 mL, 19.5 mmol). The mixture was stirred at room temperature for 12 h under $N_2$-flow, poured into ice-water and extracted with EtOAc. The organic layer was dried over $MgSO_4$, filtered and concentrated under reduced pressure. The residue was purified by column chromatography on silica gel (15-40 μm, 80 g in heptane/EtOAc 95/5). The pure fractions were combined and evaporated under reduced pressure to give 4-methyl-5-(trifluoromethoxy)-2-((trimethylsilyl)ethynyl)aniline 4a (1.34 g).

Synthesis of Intermediate 4b:

To a mixture of 4-methyl-5-(trifluoromethoxy)-2-((trimethylsilyl)ethynyl)aniline 4a (1.14 g, 3.97 mmol) in N-methyl-pyrrolidone (11 mL) under $N_2$-flow, was added potassium tert-butoxide (1.33 g, 11.9 mmol) in one portion. The reaction was stirred at 80° C. for 12 h, poured into ice-water, acidified with 3N HCl until pH 4-5 and extracted with EtOAc. The organic layer was washed 3 times with water, separated, dried over $MgSO_4$, filtered and the solvent was evaporated under reduced pressure. The residue was purified by column chromatography on silica gel (15-40 μm, 80 g in heptane/EtOAc 90/10). The pure fractions were combined and evaporated to under reduced pressure to give 5-methyl-6-(trifluoromethoxy)-1H-indole 4b (675 mg).

Synthesis of Intermediate 4c:

Diethylaluminum chloride 1M in hexane (4.1 mL, 4.1 mmol) was added dropwise at 0° C. to a solution of 5-methyl-6-(trifluoromethoxy)-1H-indole 4b (590 mg, 2.74 mmol) in $CH_2Cl_2$ (12 mL). After 30 min at 0° C., 2-(4-fluoro-2-methoxyphenyl)acetyl chloride 1a' (833 mg, 4.1 mmol, synthesis: see Example 1) in $CH_2Cl_2$ (6 mL) was added slowly at 0° C. The reaction was stirred at 0° C. for 3 h. Ice-water was added.

The precipitate was filtered off, washed with water and dried under vacuum to afford 2-(4-fluoro-2-methoxyphenyl)-1-(5-methyl-6-(trifluoromethoxy)-1H-indol-3-yl)ethanone 4c (900 mg).

Synthesis of Intermediate 4d:

At 0° C., a solution of phenyltrimethylammonium tribromide [CAS 4207-56-1] (897 mg, 2.39 mmol) in THF (8 mL) was added dropwise to a mixture of 2-(4-fluoro-2-methoxyphenyl)-1-(5-methyl-6-(trifluoromethoxy)-1H-indol-3-yl)ethanone 4c (910 mg, 2.39 mmol) in THF (9 mL). The mixture was stirred at 0° C. for 1 h and at room temperature for 4 h. The precipitate was filtered off and washed with EtOAc. The filtrate was concentrated under reduced pressure. The residue was taken up with EtOAc, washed with water, dried over $MgSO_4$, filtered and the solvent was evaporated under reduced pressure to give 2-bromo-2-(4-fluoro-2-methoxyphenyl)-1-(5-methyl-6-(trifluoromethoxy)-1H-indol-3-yl)ethanone 4d (1.26 g).

Synthesis of Compound 4 and Chiral Separation into Enantiomers 4A and 4B:

A mixture of 2-bromo-2-(4-fluoro-2-methoxyphenyl)-1-(5-methyl-6-(trifluoromethoxy)-1H-indol-3-yl)ethanone 4d (950 mg, 2.41 mmol), 2-(3-amino-5-methoxyphenoxy)ethanol [CAS 725237-16-1] (662 mg, 3.62 mmol) and diisopropylethylamine (623 μL, 3.62 mmol) in THF (10 mL) and $CH_3CN$ (10 mL) was stirred at 50° C. for 12 h. The solution was concentrated under reduced pressure. The residue was taken up with EtOAc. The organic layer was washed with water and 1N HCl (twice). The organic layer was separated, dried over $MgSO_4$, filtered and the solvent was evaporated under reduced pressure. The residue was purified by column chromatography on silica gel (15-40 μm, 80 g in $CH_2Cl_2$/MeOH 99/1). The fractions containing Compound 4 were combined and the solvent was evaporated under reduced pressure. The residue was further purified by column chromatography on silica gel (irregular bare silica, 40 g in $CH_2Cl_2$/MeOH/$NH_4OH$ 97/3/0.1). The fractions containing Compound 4 were combined and the solvent was evaporated under reduced pressure to give 2-(4-fluoro-2-methoxyphenyl)-2-((3-(2-hydroxyethoxy)-5-methoxyphenyl)amino)-1-(5-methyl-6-(trifluoromethoxy)-1H-indol-3-yl)ethanone (Compound 4, 720 g) as a racemic mixture. The Enantiomers were separated via Preparative Chiral SFC (Stationary phase: Chiralcel® OD-H 5 μm 250×30 mm, Mobile phase: 70% $CO_2$, 30% iPrOH (+0.3% $iPrNH_2$) to give 333 mg of the first eluted enantiomer and 317 mg of the second eluted enantiomer. The first eluted enantiomer was solidified from diisopropyl ether/heptane to afford Enantiomer 4A (252 mg). The second eluted enantiomer was solidified from diisopropyl ether/heptane to afford Enantiomer 4B (270 mg).

Compound 4:

$^1$H NMR (500 MHz, DMSO-$d_6$) δ ppm 2.34 (s, 3H) 3.61 (s, 3H) 3.64 (q, J=5.0 Hz, 2H) 3.77-3.88 (m, 2H) 3.95 (s, 3H) 4.79 (t, J=5.7 Hz, 1H) 5.71 (t, J=2.0 Hz, 1H) 5.93 (d, J=1.9 Hz, 2H) 6.13 (d, J=7.9 Hz, 1H) 6.34 (d, J=7.9 Hz, 1H) 6.72 (td, J=8.4, 2.4 Hz, 1H) 6.92 (dd, J=11.3, 2.5 Hz, 1H) 7.36 (dd, J=8.5, 6.9 Hz, 1H) 7.41 (d, J=0.9 Hz, 1H) 8.10 (s, 1H) 8.47 (s, 1H) 12.04 (br s, 1H)

LC/MS (method LC-C): $R_t$ 3.20 min, MH$^+$ 563

Enantiomer 4A:

$^1$H NMR (500 MHz, DMSO-$d_6$) δ ppm 2.34 (s, 3H) 3.61 (s, 3H) 3.64 (q, J=5.0 Hz, 2H) 3.77-3.88 (m, 2H) 3.95 (s, 3H) 4.79 (t, J=5.5 Hz, 1H) 5.71 (t, J=2.0 Hz, 1H) 5.93 (d, J=2.2 Hz, 2H) 6.14 (d, J=7.9 Hz, 1H) 6.35 (d, J=7.9 Hz, 1H) 6.73 (td, J=8.4, 2.4 Hz, 1H) 6.93 (dd, J=11.2, 2.4 Hz, 1H) 7.36 (dd, J=8.5, 6.9 Hz, 1H) 7.41 (s, 1H) 8.11 (s, 1H) 8.47 (s, 1H) 12.01 (br s, 1H)

LC/MS (method LC-D): $R_t$ 2.92 min, MH$^+$ 563

$[α]_D^{20}$: −96.76° (c 0.2191, DMF)

Chiral SFC (method SFC-C): $R_t$ 2.02 min, MH$^+$ 563, chiral purity 100%.

Enantiomer 4B:

$^1$H NMR (500 MHz, DMSO-$d_6$) δ ppm 2.34 (s, 3H) 3.61 (s, 3H) 3.64 (q, J=5.3 Hz, 2H) 3.77-3.89 (m, 2H) 3.95 (s, 3H) 4.79 (t, J=5.4 Hz, 1H) 5.71 (t, J=2.0 Hz, 1H) 5.93 (d, J=2.2 Hz, 2H) 6.14 (d, J=8.2 Hz, 1H) 6.35 (d, J=7.9 Hz, 1H) 6.73 (td, J=8.5, 2.5 Hz, 1H) 6.93 (dd, J=11.3, 2.5 Hz, 1H) 7.36 (dd, J=8.5, 6.9 Hz, 1H) 7.41 (s, 1H) 8.11 (s, 1H) 8.47 (s, 1H) 11.99 (br s, 1H)

LC/MS (method LC-D): $R_t$ 2.92 min, MH$^+$ 563
$[\alpha]_D^{20}$: +98.79° (c 0.2227, DMF)
Chiral SFC (method SFC-C): $R_t$ 3.26 min, MH$^+$ 563, chiral purity 100%.

Example 5: Synthesis of 2-(4-fluoro-2-methoxyphenyl)-2-((3-(2-hydroxyethoxy)-5-methoxyphenyl)amino)-1-(5-methyl-1H-indol-3-yl)ethanone (Compound 5) and chiral separation into Enantiomers 5A and 5B

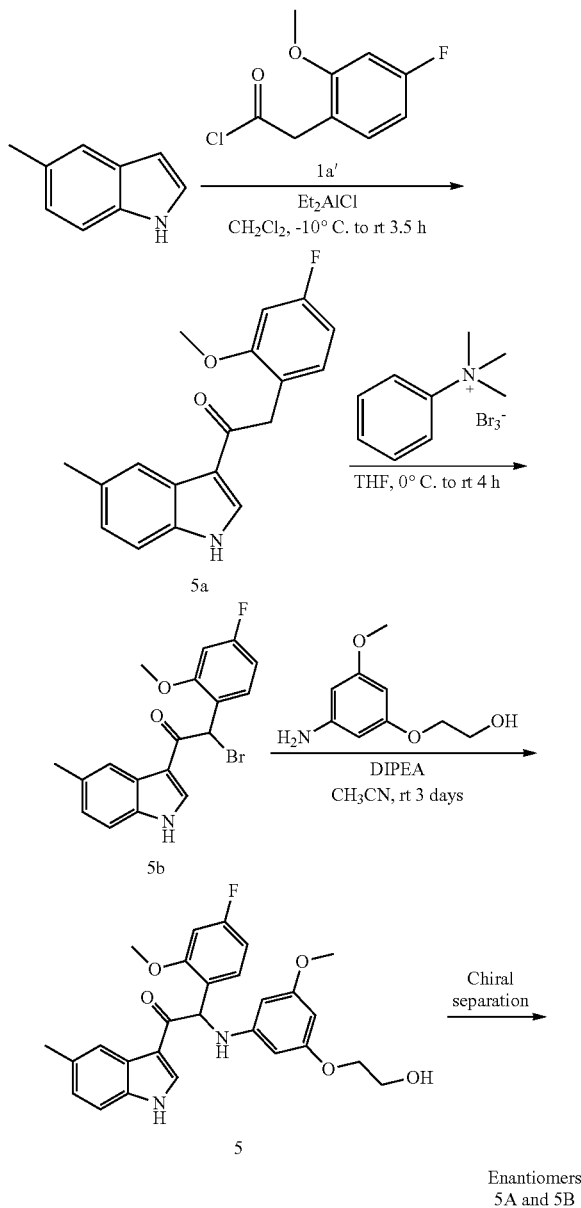

Synthesis of Intermediate 5a:
A solution 5-methyl-1H-indole [CAS 614-96-0] (5 g, 38.1 mmol) in CH$_2$Cl$_2$ (100 mL) was cooled to −10° C. under N$_2$-atmosphere. A solution of diethylaluminum chloride 1M in hexane (57.2 mL, 57.2 mmol) was added dropwise and the resulting mixture was kept at −10° C. for 10 min. A solution of 2-(4-fluoro-2-methoxyphenyl)acetyl chloride 1a' (11.6 g, 57.2 mmol) in CH$_2$Cl$_2$ (100 mL) was added dropwise. The reaction mixture was stirred at room temperature for 3.5 h. The reaction mixture was poured out in a stirring ice/Rochelle salt solution. The mixture was filtered over Dicalite® and the filter cake was washed several times with THF. The filtrates were combined. The layers were separated and the organic layer was washed with water, dried over MgSO$_4$, filtered and evaporated under reduced pressure. The solid residue was suspended in CH$_2$Cl$_2$ (30 mL). The precipitate was filtered off, washed (2×) with a small amount of CH$_2$Cl$_2$ and dried under vacuum at 50° C. to provide 2-(4-fluoro-2-methoxyphenyl)-1-(5-methyl-1H-indol-3-yl)ethanone 5a (7.19 g).

Synthesis of Intermediate 5b:
A stirred solution of 2-(4-fluoro-2-methoxyphenyl)-1-(5-methyl-1H-indol-3-yl)ethanone 5a (7.19 g, 24.2 mmol) in THF (500 mL) was cooled to 0° C. A solution of phenyltrimethylammonium tribromide [CAS 4207-56-1] (10 g, 26.6 mmol) in THF (150 mL) was added dropwise. The reaction mixture was stirred at room temperature for 4 h. The solids were removed by filtration and washed with THF. The combined filtrates were evaporated under reduced pressure. The residue was mixed with EtOAc (50 mL). The solids were isolated by filtration, washed with a small amount of EtOAc and dried under vacuum at 50° C. to provide 2-bromo-2-(4-fluoro-2-methoxyphenyl)-1-(5-methyl-1H-indol-3-yl)ethanone 5b (8.02 g).

Synthesis of Compound 5 and Chiral Separation of Enantiomers 5A and 5B:
A mixture of 2-bromo-2-(4-fluoro-2-methoxyphenyl)-1-(5-methyl-1H-indol-3-yl)ethanone 5b (3.5 g, 9.3 mmol), 2-(3-amino-5-methoxyphenoxy)ethanol [CAS 725237-16-1] (2.56 g, 13.95 mmol) and diisopropylethylamine (1.60 mL, 9.3 mmol) in CH$_3$CN was stirred at room temperature for 3 days. The reaction mixture was concentrated under reduced pressure. The residue was dissolved in CH$_2$Cl$_2$ (100 mL), washed with 1N HCl (100 mL) and brine (100 mL), dried over MgSO$_4$, filtered and evaporated under reduced pressure. The residue was purified by column chromatography (Stationary phase: Grace Reveleris® silica 120 g, Mobile phase: EtOAc/heptane gradient 35/65 to 45/55). The desired fractions were combined and evaporated under reduced pressure. The residue was further purified via preparative HPLC (Stationary phase: Uptisphere® C18 ODB— 10 µm, 200 g, 5 cm, Mobile phase: 0.25% NH$_4$HCO$_3$ solution in water, CH$_3$CN). The desired fractions were combined, evaporated under reduced pressure, and co-evaporated with EtOAc to a white powder. The solids were stirred up for 1 h in a mixture of MeOH (7 mL) and water (7 mL) and filtered off to give 2-(4-fluoro-2-methoxyphenyl)-2-((3-(2-hydroxyethoxy)-5-methoxyphenyl)amino)-1-(5-methyl-1H-indol-3-yl)ethanone (Compound 5, 917 mg) as a racemic mixture. The chiral separation of the enantiomers of Compound 5 (837 mg) was performed via Normal Phase Chiral separation (Stationary phase: AS 20 µm, Mobile phase: 100% methanol). The product fractions were combined and evaporated under reduced pressure to provide Enantiomer 5A as the first eluted product and Enantiomer 5B as the second eluted product. Both enantiomers recrystallized from a solution in MeOH (5 mL). The solids were isolated by filtration to provide Enantiomer 5A (284 mg) and Enantiomer 5B (273 mg) as white powders.

Compound 5:
$^1$H NMR (360 MHz, DMSO-d$_6$) δ ppm 2.38 (s, 3H) 3.61 (s, 3H) 3.64 (q, J=4.8 Hz, 2H) 3.75-3.90 (m, 2H) 3.96 (s, 3H) 4.80 (br t, J=5.3 Hz, 1H) 5.71 (t, J=1.8 Hz, 1H) 5.94 (d, J=1.8 Hz, 2H) 6.13 (d, J=8.1 Hz, 1H) 6.34 (d, J=8.1 Hz, 1H) 6.72 (td, J=8.4, 2.6 Hz, 1H) 6.93 (dd, J=11.3, 2.2 Hz, 1H) 7.03 (dd, J=8.4, 1.1 Hz, 1H) 7.34 (d, J=8.4 Hz, 1H) 7.37 (dd, J=8.4, 7.0 Hz, 1H) 7.97 (br s, 1H) 8.36 (s, 1H) 11.93 (br s, 1H)

LC/MS (method LC-A): $R_t$ 1.04 min, MH+ 479

Enantiomer 5A:

$^1$H NMR (400 MHz, DMSO-d$_6$) δ ppm 2.38 (s, 3H) 3.61 (s, 3H) 3.64 (q, J=5.1 Hz, 2H) 3.77-3.88 (m, 2H) 3.96 (s, 3H) 4.76 (t, J=5.5 Hz, 1H) 5.71 (t, J=2.0 Hz, 1H) 5.93 (d, J=2.0 Hz, 2H) 6.12 (d, J=7.9 Hz, 1H) 6.30 (d, J=7.9 Hz, 1H) 6.71 (td, J=8.5, 2.4 Hz, 1H) 6.92 (dd, J=11.3, 2.3 Hz, 1H) 7.03 (dd, J=8.4, 1.3 Hz, 1H) 7.31-7.40 (m, 2H) 7.97 (br s, 1H) 8.34 (s, 1H) 11.89 (br s, 1H)

LC/MS (method LC-A): $R_t$ 1.02 min, MH+ 479

$[α]_D^{20}$: +139.8° (c 0.515, DMF)

Chiral SFC (method SFC-A): $R_t$ 3.77 min, MH+ 479, chiral purity 100%.

Melting point: 198° C.

Enantiomer 5B:

$^1$H NMR (360 MHz, DMSO-d$_6$) δ ppm 2.38 (s, 3H) 3.61 (s, 3H) 3.64 (q, J=5.4 Hz, 2H) 3.74-3.90 (m, 2H) 3.96 (s, 3H) 4.81 (t, J=5.7 Hz, 1H) 5.70 (t, J=2.0 Hz, 1H) 5.93 (d, J=1.8 Hz, 2H) 6.13 (d, J=7.7 Hz, 1H) 6.34 (d, J=7.7 Hz, 1H) 6.72 (td, J=8.5, 2.4 Hz, 1H) 6.93 (dd, J=11.5, 2.4 Hz, 1H) 7.03 (dd, J=8.1, 1.5 Hz, 1H) 7.34 (d, J=8.4 Hz, 1H) 7.36 (dd, J=8.4, 7.0 Hz, 1H) 7.97 (br s, 1H) 8.36 (s, 1H) 11.93 (br s, 1H)

LC/MS (method LC-A): $R_t$ 1.03 min, MH+ 479

$[α]_D^{20}$: −135.9° (c 0.51, DMF)

Chiral SFC (method SFC-A): $R_t$ 4.19 min, MH+ 479, chiral purity 100%.

Melting point: 199° C.

Example 6: Synthesis of 1-(6-ethoxy-5-methyl-1H-indol-3-yl)-2-(4-fluoro-2-methoxyphenyl)-2-((3-(2-hydroxyethoxy)-5-methoxyphenyl)amino)ethanone (Compound 6)

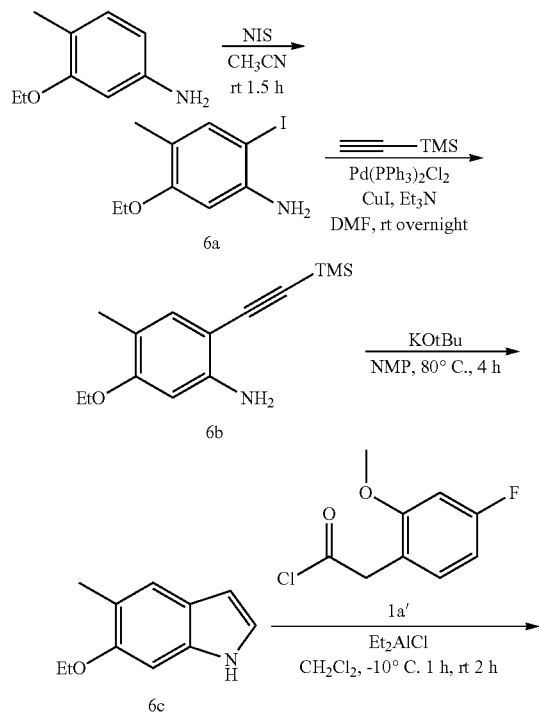

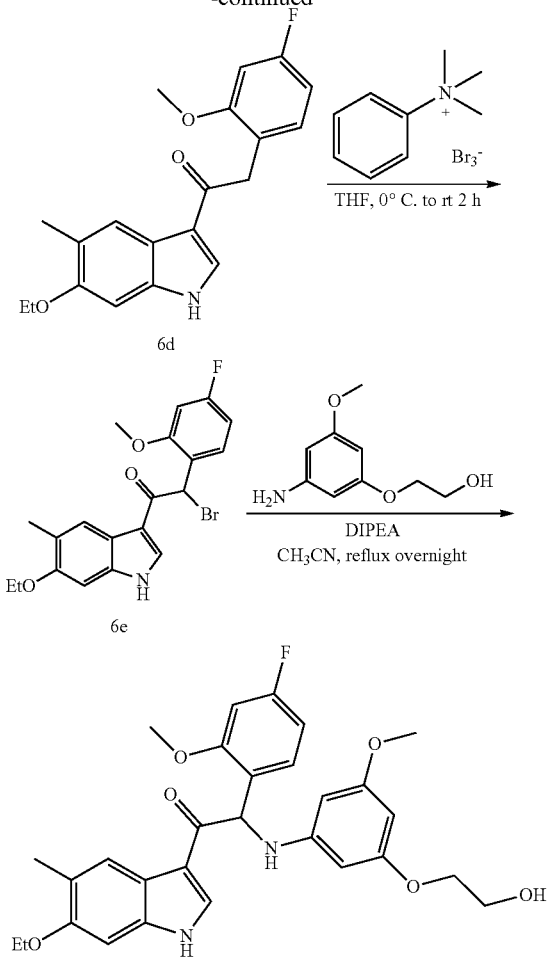

Synthesis of Intermediate 6a:

N-iodosuccinimide (14.6 g, 64.8 mmol) was added in one portion to a solution of 3-ethoxy-4-methylaniline [CAS 2486-64-8] (9.8 g, 64.8 mmol) in CH$_3$CN (200 mL), and the reaction mixture was stirred at room temperature for 1.5 h. The solvent was evaporated. The black residue was purified by flash chromatography on silica gel using heptane/EtOAc 90/10 as the eluent. The product fractions were combined and evaporated under reduced pressure. The residue was triturated with heptane. The precipitate was filtered off, washed with a small amount of heptane and dried under vacuum at 50° C. to give 5-ethoxy-2-iodo-4-methylaniline 6a (10.6 g) as a dark gray solid.

5-Ethoxy-2-iodo-4-methylaniline 6a (10.6 g, 38.4 mmol) was dissolved in DMF (150 mL) and degassed with N$_2$. Copper(I) iodide (1.46 g, 7.68 mmol), bis(triphenylphosphine)palladium(II) chloride (2.69 g, 3.84 mmol), triethylamine (16.0 mL, 115 mmol) and trimethylsilylacetylene (16.3 mL, 115 mmol) were added to the stirred solution, under nitrogen atmosphere, while cooling with a water bath. The reaction mixture was stirred at room temperature overnight. The reaction mixture was poured onto ice/water and extracted with EtOAc (2×). The combined organic layers were washed with brine, dried over MgSO$_4$, filtered, and evaporated under reduced pressure. The residue was purified by column chromatography (Stationary phase: Biotage® SNAP Ultra 340 g, Mobile phase: EtOAc/heptane gradient 0/100 to 30/70) to give 5-ethoxy-4-methyl-2-((trimethylsilyl)ethynyl)aniline 6b (7.93 g) as a black oil.

Synthesis of Intermediate 6c:

Potassium tert-butoxide (7.2 g, 64.2 mmol) was added in one portion to a solution of 5-ethoxy-4-methyl-2-((trimethylsilyl)ethynyl)aniline 6b (7.93 g, 21.4 mmol) in NMP (100 mL) at room temperature under $N_2$-atmosphere. The reaction mixture was stirred at 80° C. for 4 h. The reaction mixture was poured into ice/water and the mixture was extracted twice with EtOAc. The organic layer was washed with brine, dried over $MgSO_4$, filtered, and evaporated under reduced pressure. The residue was purified by column chromatography on silica gel using a gradient of $CH_2Cl_2$/heptane 30/70 to 40/60. The product fractions were combined, evaporated under reduced pressure and dried under vacuum at 50° C. to give 6-ethoxy-5-methyl-1H-indole 6c (1.96 g) as a yellow solid.

Diethylaluminum chloride 1M in hexane (4.71 mL, 4.71 mmol) was added dropwise, to a cooled (−10° C.) solution of 6-ethoxy-5-methyl-1H-indole 6c (550 mg, 3.14 mmol) in $CH_2Cl_2$ (150 mL) under a $N_2$-atmosphere. After stirring for 15 min at −10° C., a solution of 2-(4-fluoro-2-methoxyphenyl)acetyl chloride 1a' (763 mg, 3.77 mmol, synthesis: see Example 1) in $CH_2Cl_2$ (20 mL) was added dropwise to the reaction mixture. Stirring was continued at −10° C. for 1 h and the mixture was allowed to warm to room temperature while stirring for 2 h. The reaction mixture was poured onto ice/water containing excess Rochelle salt. After warming to room temperature, the mixture was filtered on a short pad of Dicalite® and the filter cake was rinsed several times with THF. The layers were separated. The organic layer was washed with brine, dried over $MgSO_4$, filtered, and evaporated under reduced pressure. The solid residue was suspended in $CH_2Cl_2$ (10 mL) and the solids were filtered off, washed with a small amount of $CH_2Cl_2$ and dried under vacuum at 50° C. to give 1-(6-ethoxy-5-methyl-1H-indol-3-yl)-2-(4-fluoro-2-methoxyphenyl)ethanone 6d (765 mg).

Synthesis of Intermediate 6e:

A solution of phenyltrimethylammonium tribromide [CAS 4207-56-1] (737 mg g, 1.96 mmol) in THF (30 mL) was added dropwise to a cooled (0° C.) solution of 1-(6-ethoxy-5-methyl-1H-indol-3-yl)-2-(4-fluoro-2-methoxyphenyl)ethanone 6d (761 mg, 1.78 mmol) in THF (70 mL), and the reaction mixture was allowed to warm to room temperature while stirring for 2 h. The reaction mixture was filtered and the solids were washed with THF. The filtrate was evaporated under reduced pressure and dried under vacuum at 50° C. to provide 2-bromo-1-(6-ethoxy-5-methyl-1H-indol-3-yl)-2-(4-fluoro-2-methoxyphenyl)ethanone 6e (700 mg) as a grey solid. The product was used without further purification in the next step.

Synthesis of Compound 6:

A mixture of 2-bromo-1-(6-ethoxy-5-methyl-1H-indol-3-yl)-2-(4-fluoro-2-methoxyphenyl)ethanone 6e (700 mg, 0.7 mmol), 2-(3-amino-5-methoxyphenoxy)ethanol [CAS 725237-16-1] (192 mg, 1.05 mmol) and diisopropylethylamine (180 µL, 1.05 mmol) in $CH_3CN$ (50 mL) was heated under reflux overnight. After cooling to room temperature, the solvent was evaporated under reduced pressure. The residue was dissolved in $CH_2Cl_2$. The organic solution was washed with 1N HCl, water, dried over $MgSO_4$, filtered, and evaporated under reduced pressure. The residue was purified by column chromatography (Stationary phase: Biotage® SNAP Ultra 50 g, Mobile phase: EtOAc:EtOH (3:1)/heptane gradient 0/100 to 50/50). The product fractions were combined and evaporated under reduced pressure. The residue was further purified via preparative HPLC (Stationary phase: RP XBridge® Prep C18 OBD 10 µm 30×150 mm, Mobile phase: 0.25% $NH_4HCO_3$ solution in water, $CH_3CN$). The product fractions were combined and evaporated under reduced pressure. The residue was further purified via preparative achiral SFC (Stationary phase: PYR (Pyridine) 60A 6 µm 20×250 mm, Mobile phase: $CO_2$, EtOH+0.4% $iPrNH_2$). The product fractions were combined, evaporated under reduced pressure and dried under vacuum at 50° C. to provide racemic 1-(6-ethoxy-5-methyl-1H-indol-3-yl)-2-(4-fluoro-2-methoxyphenyl)-2-((3-(2-hydroxyethoxy)-5-methoxyphenyl)amino)ethanone (Compound 6, 48 mg) as an off-white powder.

Compound 6:

$^1$H NMR (360 MHz, DMSO-$d_6$) δ ppm 1.37 (t, J=7.0 Hz, 3H) 2.21 (s, 3H) 3.60 (s, 3H) 3.64 (q, J=5.0 Hz, 2H) 3.75-3.89 (m, 2H) 3.96 (s, 3H) 4.01 (q, J=7.0 Hz, 2H) 4.80 (t, J=5.5 Hz, 1H) 5.70 (t, J=2.0 Hz, 1H) 5.92 (d, J=2.2 Hz, 2H) 6.10 (d, J=8.1 Hz, 1H) 6.32 (d, J=8.1 Hz, 1H) 6.72 (td, J=8.5, 2.4 Hz, 1H) 6.90 (s, 1H) 6.92 (dd, J=11.3, 2.6 Hz, 1H) 7.36 (dd, J=8.8, 7.0 Hz, 1H) 7.89 (s, 1H) 8.23 (s, 1H) 11.72 (br s, 1H)

LC/MS (method LC-B): $R_t$ 2.05 min, MH$^+$ 523

Example 7: Synthesis of 1-(3,7-dihydro-2H-furo[3,2-f]indol-5-yl)-2-(4-fluoro-2-methoxyphenyl)-2-((3-(2-hydroxyethoxy)-5-methoxyphenyl)amino)ethanone (Compound 7) and chiral separation into Enantiomers 7A and 7B

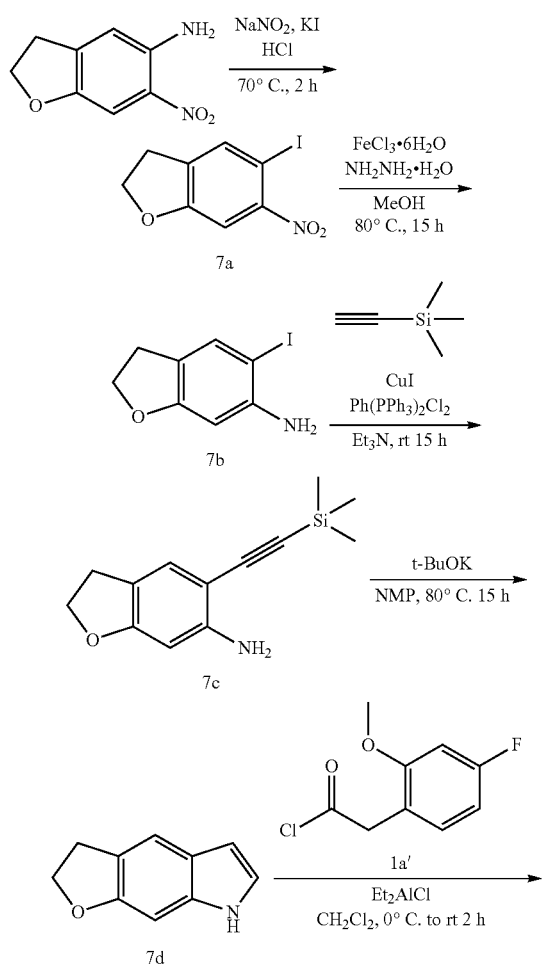

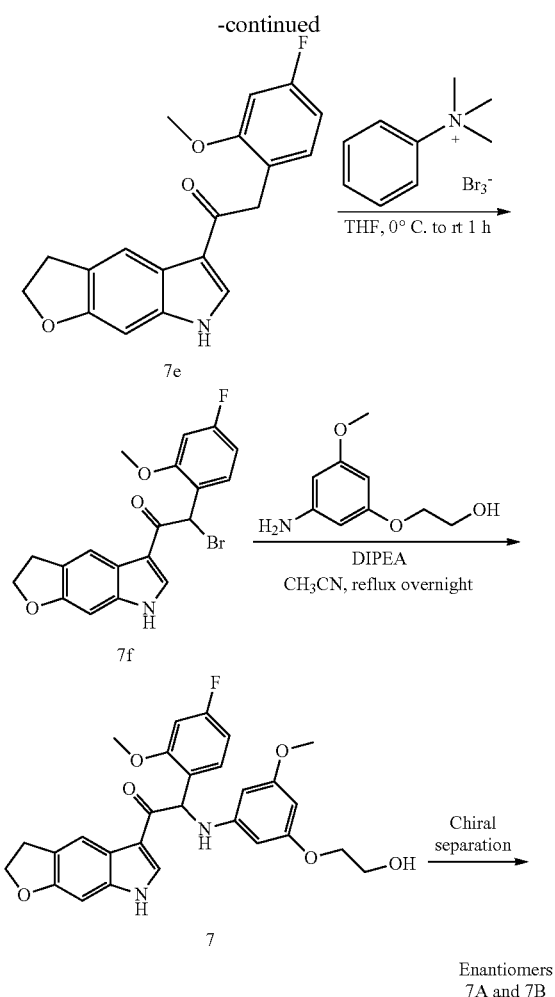

Synthesis of Intermediate 7a

A suspension of 6-nitro-2,3-dihydrobenzofuran-5-amine [CAS 84594-78-5] (135.00 g, 749.33 mmol) in concentrated HCl (250 mL) was heated to 100° C. for 10 min. The solution was cooled to 0° C. A solution of $NaNO_2$ (62.04 g, 899.20 mmol) in $H_2O$ (250 mL) was added dropwise. The reaction mixture was stirred for 30 min at 0° C. The reaction mixture was added slowly to a cooled (0° C.) solution of KI (186.58 g, 1.12 mol) in $H_2O$ (250 mL). The resulting mixture was heated to 70° C. for 2 h. After cooling to room temperature, $H_2O$ (2 L) was added and the crude product was extracted with EtOAc (2×2 L). The combined organic phases were washed with aqueous HCl (10%, 1 L), aqueous NaOH (1 N, 1 L), a saturated aqueous $Na_2SO_3$ solution (1 L) and brine (1 L). After drying over $MgSO_4$, the solvent was evaporated under reduced pressure. The residue was purified by column chromatography on silica gel (eluent: petroleum ether/EtOAc 8/1) to give 5-iodo-6-nitro-2,3-dihydrobenzofuran 7a (90.00 g) as a pale yellow solid.

Synthesis of Intermediate 7b:

To a solution of $FeCl_3.6H_2O$ (7.43 g, 27.49 mmol) in MeOH (1.5 L) were added 5-iodo-6-nitro-2,3-dihydrobenzofuran 7a (80.00 g, 274.88 mmol) and active carbon (8 g). The mixture was heated under reflux and hydrazine hydrate (27.52 g, 549.76 mmol) was added dropwise. The mixture was stirred at 80° C. for 15 h. The mixture was filtered and the filtrate was concentrated under reduced pressure. The solid residue was washed with MeOH (50 mL) to give 5-iodo-2,3-dihydrobenzofuran-6-amine 7b (50.00 g) as a pale yellow solid.

Synthesis of Intermediate 7c:

A stirred suspension of 5-iodo-2,3-dihydrobenzofuran-6-amine 7b (50.00 g, 191.53 mmol), CuI (729.53 mg, 3.83 mmol) and $Pd(PPh_3)_2Cl_2$ (4.03 g, 5.75 mmol) in triethylamine (1 L) was degassed with $N_2$ and evacuated/backfilled with $N_2$ (3 cycles). The reaction mixture was stirred at 25° C. for 10 minutes. After addition of ethynyl(trimethyl)silane (22.57 g, 229.84 mmol) the suspension was stirred for 15 hours at 25° C. under $N_2$ atmosphere. The reaction mixture was diluted with water (2 L) and extracted with EtOAc (2×2 L). The combined organic phases were washed with brine (2 L) and dried over $MgSO_4$. Removal of the solvent under reduced pressure gave the crude product as brown solid. The residue was purified by column chromatography on silica gel (eluent: petroleum ether/EtOAc 8/1) to provide 5-(2-trimethylsilylethynyl)-2,3-dihydrobenzofuran-6-amine 7c (30.00 g) as a pale yellow solid.

Synthesis of Intermediate 7d:

A mixture of 5-(2-trimethylsilylethynyl)-2,3-dihydrobenzofuran-6-amine 7c (25.00 g, 108.05 mmol) and t-BuOK (36.37 g, 324.16 mmol) in NMP (500 mL) was stirred at 80° C. for 15 h. The mixture was concentrated under reduced pressure. The residue was purified by column chromatography on silica gel (eluent: petroleum ether/EtOAc 8/1) to give 3,7-dihydro-2H-furo[3,2-f]indole 7d (11.10 g) as a pale yellow solid.

Synthesis of Intermediate 7e:

A solution 3,7-dihydro-2H-furo[3,2-f]indole 7d (1.8 g, 11.3 mmol) in $CH_2Cl_2$ (150 mL) was cooled on an ice-bath under $N_2$-atmosphere. A solution of diethylaluminum chloride 1M in hexane (17.0 mL, 17.0 mmol) was added dropwise and the resulting mixture was kept at 0° C. for 15 min. A solution of 2-(4-fluoro-2-methoxyphenyl)acetyl chloride 1a' (3.21 g, 15.8 mmol) in $CH_2Cl_2$ (100 mL) was added dropwise. Stirring was continued at 0° C. for 1 h. The ice-bath was removed and the reaction mixture was stirred at room temperature for 2 h. The reaction mixture was poured out into a stirring ice/Rochelle salt solution. After the ice had melted, the mixture was filtered over Dicalite® and the filter cake was washed several times with THF. The filtrates were combined. The layers were separated and the organic layer was washed with brine and water. The combined aqueous layers were extracted with THF and the combined organic layers were dried over $MgSO_4$, filtered and evaporated under reduced pressure. The solid residue was suspended in $CH_2Cl_2$ (20 mL). The precipitate was filtered off, washed with a small amount of $CH_2Cl_2$ and dried under vacuum at 50° C. to provide 1-(3,7-dihydro-2H-furo[3,2-f]indol-5-yl)-2-(4-fluoro-2-methoxyphenyl)ethanone 7e (2.39 g) as a white solid.

Synthesis of Intermediate 7f:

A stirred solution of 1-(3,7-dihydro-2H-furo[3,2-f]indol-5-yl)-2-(4-fluoro-2-methoxyphenyl)ethanone 7e (2.39 g, 7.35 mmol) in THF (50 mL) was cooled to 0° C. A solution of phenyltrimethylammonium tribromide [CAS 4207-56-1] (3.04 g, 8.09 mmol) in THF (100 mL) was added dropwise. The reaction mixture was stirred at room temperature for 1 h. The solids were removed by filtration and washed with THF. The combined filtrates were evaporated under reduced pressure. The residue was triturated with a small amount of $CH_2Cl_2$/heptane (1/1). The solids were isolated by filtration and washed with a small amount of $CH_2Cl_2$/heptane (1/1) to provide 2-bromo-1-(3,7-dihydro-2H-furo[3,2-f]indol-5-yl)-2-(4-fluoro-2-methoxyphenyl)ethanone 7f (2.12 g) as a yellow powder.

Synthesis of Compound 7 and chiral separation of Enantiomers 7A and 7B:

A mixture of 2-bromo-1-(3,7-dihydro-2H-furo[3,2-f]indol-5-yl)-2-(4-fluoro-2-methoxyphenyl)ethanone 7f (2.10 g, 5.20 mmol), 2-(3-amino-5-methoxyphenoxy)ethanol [CAS 725237-16-1] (1.90 g, 10.4 mmol) and diisopropylethylamine (1.34 mL, 7.79 mmol) in CH₃CN (50 mL) was heated under reflux overnight. The reaction mixture was concentrated under reduced pressure. The residue was dissolved in $CH_2Cl_2$, washed with 1N HCl and water, dried over $MgSO_4$, filtered and evaporated under reduced pressure. The residue was purified by column chromatography (Stationary phase: Biotage® SNAP Ultra silica 100 g, Mobile phase: EtOAc:EtOH (3:1)/heptane gradient 0/100 to 70/30). The desired fractions were combined and evaporated under reduced pressure. The residue was dried under vacuum at 50° C. to provide 1-(3,7-dihydro-2H-furo[3,2-f]indol-5-yl)-2-(4-fluoro-2-methoxyphenyl)-2-((3-(2-hydroxyethoxy)-5-methoxyphenyl)amino)ethanone (Compound 7, 1.33 g) as a racemic mixture. The chiral separation of the enantiomers of Compound 7 (1.33 g) was performed via Preparative SFC (Stationary phase: Chiralpak® Diacel AS 20×250 mm, Mobile phase: $CO_2$, EtOH+0.4% $iPrNH_2$). The product fractions were combined and evaporated under reduced pressure to provide Enantiomer 7A as the first eluted product and Enantiomer 7B as the second eluted product. Both enantiomers were further purified via Preparative SFC (Stationary phase: Chiralpak® Diacel AD 20×250 mm, Mobile phase: $CO_2$, EtOH+0.4% $iPrNH_2$) and subsequently by column chromatography (Stationary phase: Grace Reveleris® silica 12 g, Mobile phase: EtOAc:EtOH (3:1)/heptane gradient 0/100 to 80/20). Enantiomer 7A was crystallized from MeOH (6 mL). The solid was isolated by filtration, washed with a small amount of MeOH and dried under vacuum at 50° C. to provide Enantiomer 7A (275 mg) as a white powder. Enantiomer 7B was crystallized from a mixture of MeOH (6 mL) and water (6 drops). The solid was isolated by filtration, washed with a small amount of MeOH and dried under vacuum at 50° C. to provide Enantiomer 7B (180 mg) as a white powder.

Enantiomer 7A:
$^1$H NMR (360 MHz, DMSO-$d_6$) δ ppm 3.21 (br t, J=8.2 Hz, 2H) 3.60 (s, 3H) 3.63 (q, J=5.4 Hz, 2H) 3.76-3.87 (m, 2H) 3.96 (s, 3H) 4.52 (t, J=8.8 Hz, 2H) 4.80 (t, J=5.5 Hz, 1H) 5.70 (t, J=2.0 Hz, 1H) 5.92 (d, J=2.2 Hz, 2H) 6.09 (d, J=8.1 Hz, 1H) 6.32 (d, J=8.1 Hz, 1H) 6.72 (td, J=8.4, 2.6 Hz, 1H) 6.76 (s, 1H) 6.92 (dd, J=11.3, 2.6 Hz, 1H) 7.35 (dd, J=8.6, 6.8 Hz, 1H) 7.95 (br s, 1H) 8.22 (s, 1H) 11.72 (br s, 1H)

LC/MS (method LC-B): $R_t$ 1.80 min, MH$^+$ 507

$[α]_D^{20}$: +128.6° (c 0.394, DMF)

Chiral SFC (method SFC-A): $R_t$ 4.35 min, MH$^+$ 507, chiral purity 100%.

Melting point: 221° C.

Enantiomer 7B:
$^1$H NMR (360 MHz, DMSO-$d_6$) δ ppm 3.21 (br t, J=8.4 Hz, 2H) 3.60 (s, 3H) 3.64 (q, J=4.9 Hz, 2H) 3.74-3.89 (m, 2H) 3.96 (s, 3H) 4.52 (t, J=9.0 Hz, 2H) 4.80 (t, J=5.5 Hz, 1H) 5.70 (t, J=2.0 Hz, 1H) 5.92 (d, J=2.2 Hz, 2H) 6.09 (d, J=7.7 Hz, 1H) 6.32 (d, J=8.1 Hz, 1H) 6.72 (td, J=8.4, 2.6 Hz, 1H) 6.76 (br s, 1H) 6.92 (dd, J=11.3, 2.6 Hz, 1H) 7.35 (dd, J=8.8, 7.0 Hz, 1H) 7.95 (br s, 1H) 8.22 (s, 1H) 11.73 (br s, 1H)

LC/MS (method LC-B): $R_t$ 1.80 min, MH$^+$ 507

$[α]_D^{20}$: −134.2° (c 0.403, DMF)

Chiral SFC (method SFC-A): $R_t$ 4.47 min, MH$^+$ 507, chiral purity 100%.

Melting point: 220° C.

Example 8: Synthesis of 1-(7,8-dihydro-1H-furo[2,3-g]indol-3-yl)-2-(4-fluoro-2-methoxyphenyl)-2-((3-(2-hydroxyethoxy)-5-methoxyphenyl)amino)ethanone (Compound 8) and chiral separation into Enantiomers 8A and 8B

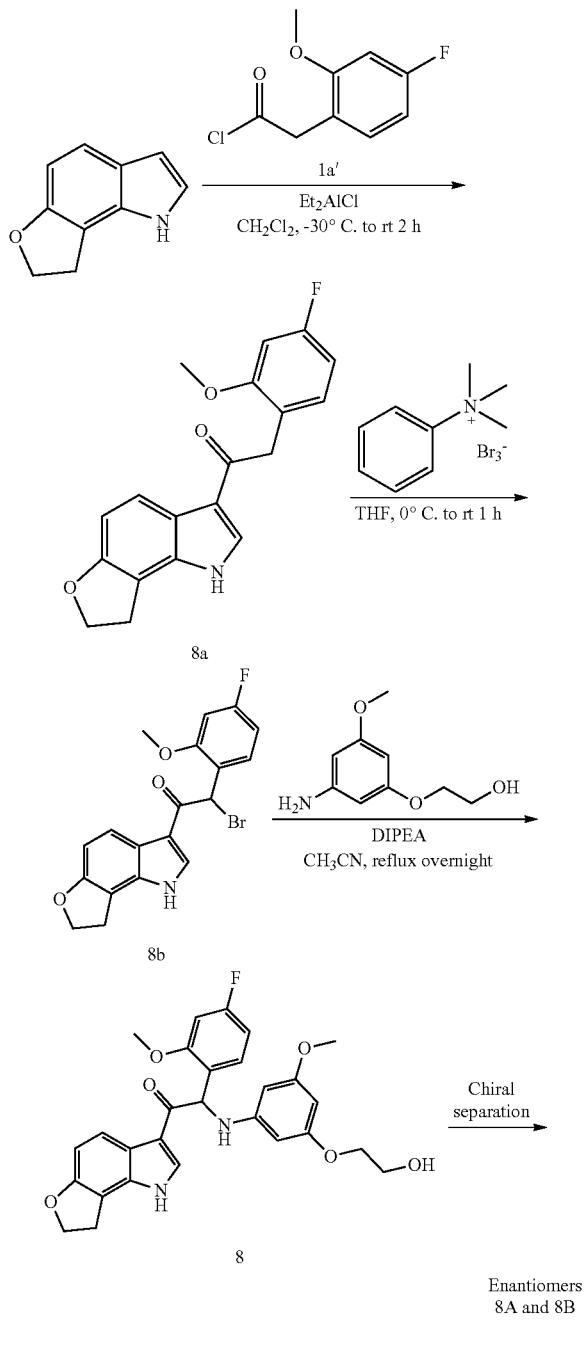

Synthesis of Intermediate 8a:

A solution 7,8-dihydro-1H-furo[2,3-g]indole [CAS 170728-95-7] (1.80 g, 11.3 mmol) in $CH_2Cl_2$ (150 mL) was cooled to −30° C. under $N_2$-atmosphere. A solution of diethylaluminum chloride 1M in hexane (17.0 mL, 17.0 mmol) was added dropwise and the resulting mixture was kept at −30° C. for 15 min. A solution of 2-(4-fluoro-2-methoxyphenyl)acetyl chloride 1a' (3.21 g, 15.8 mmol) in $CH_2Cl_2$ (100 mL) was added dropwise. The reaction mixture was stirred at −30° C. for 1 h, and subsequently at room temperature for 2 h. The reaction mixture was poured out into a stirring ice/Rochelle salt solution. After the ice had melted, the mixture was filtered over Dicalite® and the filter cake was washed several times with THF. The filtrates were combined. The layers were separated and the organic layer was washed with brine and water. The combined aqueous layers were extracted with THF and the combined organic layers were dried over $MgSO_4$, filtered and evaporated under reduced pressure. The solid residue was suspended in $CH_2Cl_2$ (20 mL). The precipitate was filtered off, washed with a small amount of $CH_2Cl_2$ and dried under vacuum at 50° C. to provide 1-(7,8-dihydro-1H-furo[2,3-g]indol-3-yl)-2-(4-fluoro-2-methoxyphenyl)ethanone 8a (2.49 g).

Synthesis of Intermediate 8b:

A stirred solution of 1-(7,8-dihydro-1H-furo[2,3-g]indol-3-yl)-2-(4-fluoro-2-methoxyphenyl)ethanone 8a (2.49 g, 7.65 mmol) in THF (50 mL) was cooled to 0° C. A solution of phenyltrimethylammonium tribromide [CAS 4207-56-1] (3.16 g, 8.42 mmol) in THF (100 mL) was added dropwise. The reaction mixture was stirred at room temperature for 1 h. The solids were removed by filtration and washed with THF. The combined filtrates were evaporated under reduced pressure. The residue was triturated with a small amount of $CH_2Cl_2$/heptane (1/1). The solids were isolated by filtration and washed with a small amount of $CH_2Cl_2$/heptane (1/1) to provide 2-bromo-1-(7,8-dihydro-1H-furo[2,3-g]indol-3-yl)-2-(4-fluoro-2-methoxyphenyl)ethanone 8b (1.2 g) as a yellow solid.

Synthesis of Compound 8 and Chiral Separation of Enantiomers 8A and 8B:

A mixture of 2-bromo-1-(7,8-dihydro-1H-furo[2,3-g]indol-3-yl)-2-(4-fluoro-2-methoxyphenyl)ethanone 8b (1.2 g, 2.97 mmol), 2-(3-amino-5-methoxyphenoxy)ethanol [CAS 725237-16-1] (1.09 g, 5.94 mmol) and diisopropylethylamine (7.67 µL, 4.45 mmol) in $CH_3CN$ (50 mL) was heated under reflux overnight. The reaction mixture was concentrated under reduced pressure. The residue was dissolved in $CH_2Cl_2$, washed with 1N HCl and water, dried over $MgSO_4$, filtered and evaporated under reduced pressure. The residue was purified by column chromatography (Stationary phase: Biotage® SNAP Ultra silica 100 g, Mobile phase: EtOAc:EtOH(3:1)/heptane gradient 0/100 to 70/30). The desired fractions were combined and evaporated under reduced pressure. The residue was dried under vacuum at 50° C. to provide 1-(7,8-dihydro-1H-furo[2,3-g]indol-3-yl)-2-(4-fluoro-2-methoxyphenyl)-2-((3-(2-hydroxyethoxy)-5-methoxyphenyl)amino)ethanone (Compound 8, 445 mg) as a racemic mixture. The chiral separation of the enantiomers of Compound 8 (445 mg) was performed via Preparative SFC (Stationary phase: Chiralpak® Diacel AS 20×250 mm, Mobile phase: $CO_2$, EtOH+0.4% $iPrNH_2$). The product fractions were combined and evaporated under reduced pressure to provide Enantiomer 8A as the first eluted product and Enantiomer 8B as the second eluted product. Enantiomer 8A was stirred up in $CH_2Cl_2$ (5 mL). The solid was isolated by filtration, washed with a small amount of $CH_2Cl_2$ and dried under vacuum at 50° C. to provide Enantiomer 8B (97 mg) as a white powder. Enantiomer 8B was purified by Preparative SFC (Stationary phase: Chiralpak® Diacel AD 20×250 mm, Mobile phase: $CO_2$, EtOH+0.4% $iPrNH_2$). The product fractions were combined and evaporated under reduced pressure. Enantiomer 8B was stirred up in $CH_2Cl_2$ (5 mL). The solid was isolated by filtration, washed with a small amount of $CH_2Cl_2$ and dried under vacuum at 50° C. to provide Enantiomer 8B (89 mg) as a white powder.

Enantiomer 8A:

$^1$H NMR (360 MHz, DMSO-$d_6$) δ ppm 3.25-3.32 (m, 2H) 3.60 (s, 3H) 3.64 (q, J=5.4 Hz, 2H) 3.75-3.89 (m, 2H) 3.96 (s, 3H) 4.57 (t, J=8.8 Hz, 2H) 4.80 (t, J=5.7 Hz, 1H) 5.70 (t, J=2.0 Hz, 1H) 5.93 (d, J=2.2 Hz, 2H) 6.12 (d, J=8.1 Hz, 1H) 6.35 (d, J=8.1 Hz, 1H) 6.69-6.74 (m, 2H) 6.92 (dd, J=11.3, 2.6 Hz, 1H) 7.36 (dd, J=8.6, 6.8 Hz, 1H) 7.90 (d, J=8.4 Hz, 1H) 8.33 (s, 1H) 11.97 (br s, 1H) LC/MS (method LC-A): $R_t$ 0.94 min, MH$^+$ 507

$[α]_D^{20}$: +74.9° (c 0.379, DMF)

Chiral SFC (method SFC-A): $R_t$ 3.91 min, MH$^+$ 507, chiral purity 100%.

Melting point: 256° C.

Enantiomer 8B:

$^1$H NMR (360 MHz, DMSO-$d_6$) δ ppm 3.25-3.31 (m, 2H) 3.57-3.69 (m, 5H) 3.74-3.90 (m, 2H) 3.96 (s, 3H) 4.58 (br t, J=8.8 Hz, 2H) 4.80 (t, J=5.5 Hz, 1H) 5.70 (t, J=2.0 Hz, 1H) 5.94 (d, J=1.5 Hz, 2H) 6.13 (br d, J=8.1 Hz, 1H) 6.36 (br d, J=7.7 Hz, 1H) 6.67-6.77 (m, 2H) 6.92 (dd, J=11.0, 1.8 Hz, 1H) 7.37 (t, J=7.7 Hz, 1H) 7.91 (d, J=8.4 Hz, 1H) 8.33 (s, 1H) 11.96 (br s, 1H)

LC/MS (method LC-B): $R_t$ 1.79 min, MH$^+$ 507

$[α]_D^{20}$: −73.3° (c 0.3645, DMF)

Chiral SFC (method SFC-A): $R_t$ 4.38 min, MH$^+$ 507, chiral purity 100%.

Melting point: 254° C.

Example 9: Synthesis 2-(4-chloro-2-methoxyphenyl)-1-(6-fluoro-5-methyl-1H-indol-3-yl)-2-((3-(2-hydroxyethoxy)-5-methoxyphenyl)amino)ethanone (Compound 9) and chiral separation into Enantiomers 9A and 9B

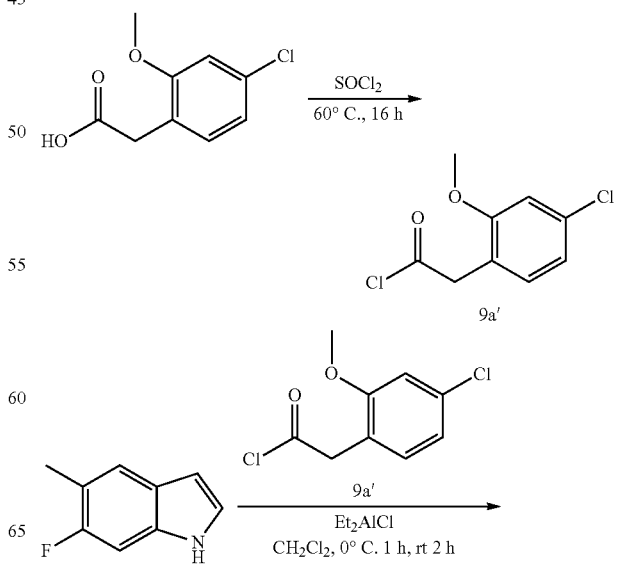

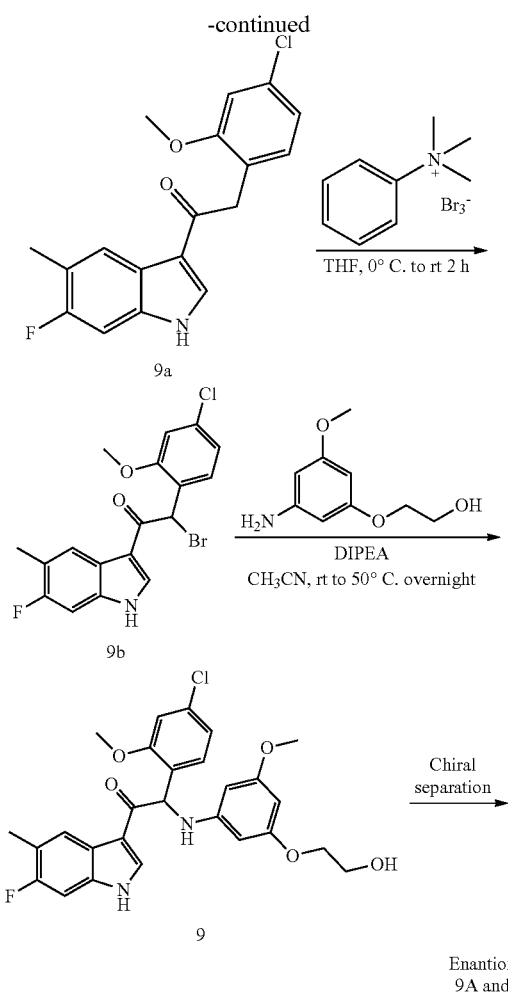

Synthesis of Intermediate 9a':

2-(4-Chloro-2-methoxyphenyl)acetic acid [CAS 170737-95-8] (5.8 g, 28.9 mmol) was added in small portions to thionyl chloride (50 mL) and the resulting solution was stirred overnight at 60° C. The solvent was concentrated under reduced pressure and co-evaporated with toluene to give 2-(4-chloro-2-methoxyphenyl)-acetyl chloride 9a' (6.5 g) as an oily residue that was used without further purification in the next step.

Synthesis of Intermediate 9a:

A solution of 6-fluoro-5-methyl-1H-indole [CAS 162100-95-0] (1.7 g, 11.4 mmol) in $CH_2Cl_2$ (100 mL) was cooled to 0° C. under $N_2$-atmosphere. A solution of diethylaluminum chloride 1M in hexane (17.1 mL, 17.1 mmol) was added dropwise and the resulting mixture was kept at 0° C. for 15 min. A solution of 2-(4-chloro-2-methoxyphenyl)acetyl chloride 9a' (3.50 g, 16 mmol) in $CH_2Cl_2$ (50 mL) was added dropwise. Stirring was continued at 0° C. for 1 h and the reaction mixture was subsequently stirred at room temperature for 2 h. The reaction mixture was poured out into a stirring ice/Rochelle salt solution. After the ice had melted, the mixture was filtered over Dicalite® and the filter cake was washed several times with THF. The filtrates were combined. The layers were separated and the organic layer was washed with brine, dried over $MgSO_4$, filtered and evaporated under reduced pressure. The solid residue was suspended in $CH_2Cl_2$ (30 mL) and the precipitate was filtered off and dried under vacuum at 50° C. to provide 2-(4-chloro-2-methoxyphenyl)-1-(6-fluoro-5-methyl-1H-indol-3-yl)ethanone 9a (2.76 g).

Synthesis of Intermediate 9b:

A stirred solution of 2-(4-chloro-2-methoxyphenyl)-1-(6-fluoro-5-methyl-1H-indol-3-yl)ethanone 9a (2.76 g, 8.32 mmol) in THF (350 mL) was cooled to 0° C. A solution of phenyltrimethylammonium tribromide [CAS 4207-56-1] (3.44 g, 9.15 mmol) in THF (50 mL) was added dropwise. The reaction mixture was stirred at 0° C. for 2 h and subsequently at room temperature for 2 h. The solids were removed by filtration and washed with THF. The combined filtrates were evaporated under reduced pressure. The residue was mixed with EtOAc (50 mL). The solids were isolated by filtration, washed with a small amount of EtOAc and dried under vacuum at 50° C. to provide 2-bromo-2-(4-chloro-2-methoxyphenyl)-1-(6-fluoro-5-methyl-1H-indol-3-yl)ethanone 9b (3.21 g) as a white solid, which was used without further purification in the next step.

Synthesis of Compound 9 and chiral separation of Enantiomers 9A and 9B:

A mixture 2-bromo-2-(4-chloro-2-methoxyphenyl)-1-(6-fluoro-5-methyl-1H-indol-3-yl)ethanone 9b (1.6 g, 3.90 mmol), 2-(3-amino-5-methoxyphenoxy)ethanol [CAS 725237-16-1] (1.07 g, 5.84 mmol) and diisopropylethylamine (671 µL, 3.90 mmol) in $CH_3CN$ (100 mL) was stirred at room temperature overnight and subsequently at 50° C. for 18 h. The reaction mixture was concentrated under reduced pressure. The residue was dissolved in $CH_2Cl_2$ (100 mL), washed with 1N HCl (100 mL) and water (100 mL), dried over $MgSO_4$, filtered and evaporated under reduced pressure. The residue was purified by flash chromatography (Stationary phase: Grace Reveleris® silica 120 g, Mobile phase: EtOAc:EtOH(3:1)/heptane gradient 0/100 to 50/50). The desired fractions were combined and evaporated under reduced pressure. The residual solid was precipitated from $CH_2Cl_2$/heptane. The precipitate was filtered off and washed with $CH_2Cl_2$/heptane (1/1). The solid (1.53 g) was further purified via preparative HPLC (Stationary phase: Uptisphere® C18 ODB—10 µm, 200 g, 5 cm, Mobile phase: 0.25% $NH_4HCO_3$ solution in water, $CH_3CN$). The desired fractions were combined, evaporated under reduced pressure, and co-evaporated with EtOAc (20 mL) to give 2-(4-chloro-2-methoxyphenyl)-1-(6-fluoro-5-methyl-1H-indol-3-yl)-2-((3-(2-hydroxyethoxy)-5-methoxyphenyl)amino) ethanone (Compound 9, 1.07 g) as a racemic mixture. The chiral separation of the enantiomers of Compound 9 (1.04 g) was performed via Normal Phase Chiral separation (Stationary phase: (S,S)-Whelk-O1, Mobile phase: 100% ethanol). The product fractions were combined and evaporated to provide Enantiomer 9A as the first eluted product and Enantiomer 9B as the second eluted product.

Enantiomer 9A (421 mg) was purified by flash chromatography (Stationary phase: Grace Reveleris® silica 12 g, Mobile phase: heptane/EtOAc/EtOH gradient 100/0/0 to 40/45/15). The desired fractions were combined and evaporated under reduced pressure. The residue was triturated with $H_2O$ (2.5 mL) and MeOH (0.75 mL). After stirring for 15 min, the solids were filtered off, washed (3×) with a mixture of $H_2O$/MeOH 3/1, and dried at under vacuum at 50° C. to provide Enantiomer 9A (303 mg).

Enantiomer 9B (336 mg) was purified by flash chromatography (Stationary phase: Grace Reveleris® silica 12 g, Mobile phase: heptane/EtOAc/EtOH gradient 100/0/0 to 40/45/15). The desired fractions were combined and evaporated under reduced pressure. The residue was triturated with $H_2O$ (2.5 mL) and MeOH (0.75 mL). After stirring for 15 min, the solids were filtered off, washed (3×) with a mixture of H₂O/MeOH 3/1, and dried at under vacuum at 50° C. to provide Enantiomer 9B (224 mg).

Compound 9:
¹H NMR (400 MHz, DMSO-d₆) δ ppm 2.30 (d, J=1.3 Hz, 3H) 3.61 (s, 3H) 3.64 (q, J=5.3 Hz, 2H) 3.77-3.89 (m, 2H) 3.96 (s, 3H) 4.77 (t, J=5.5 Hz, 1H) 5.72 (t, J=2.1 Hz, 1H) 5.93 (d, J=2.2 Hz, 2H) 6.13 (d, J=8.1 Hz, 1H) 6.34 (d, J=7.9 Hz, 1H) 6.96 (dd, J=8.4, 2.0 Hz, 1H) 7.09 (d, J=2.0 Hz, 1H) 7.22 (d, J=10.3 Hz, 1H) 7.35 (d, J=8.4 Hz, 1H) 8.01 (d, J=7.9 Hz, 1H) 8.36 (s, 1H) 11.94 (br s, 1H)
LC/MS (method LC-B): R$_t$ 2.08 min, MH⁺ 513

Enantiomer 9A:
¹H NMR (400 MHz, DMSO-d₆) δ ppm 2.30 (d, J=1.3 Hz, 3H) 3.61 (s, 3H) 3.65 (q, J=5.3 Hz, 2H) 3.74-3.90 (m, 2H) 3.96 (s, 3H) 4.77 (t, J=5.5 Hz, 1H) 5.72 (t, J=2.1 Hz, 1H) 5.93 (d, J=2.0 Hz, 2H) 6.13 (d, J=8.1 Hz, 1H) 6.34 (d, J=8.1 Hz, 1H) 6.96 (dd, J=8.3, 1.9 Hz, 1H) 7.09 (d, J=2.0 Hz, 1H) 7.22 (d, J=10.0 Hz, 1H) 7.36 (d, J=8.4 Hz, 1H) 8.02 (d, J=7.9 Hz, 1H) 8.36 (d, J=3.1 Hz, 1H) 11.94 (br d, J=2.6 Hz, 1H)
LC/MS (method LC-A): R$_t$ 1.1 min, MH⁺ 513
[α]$_D^{20}$: −141.9° (c 0.465, DMF)
Chiral SFC (method SFC-A): R$_t$ 4.33 min, MH⁺ 513, chiral purity 100%.

Enantiomer 9B:
¹H NMR (400 MHz, DMSO-d₆) δ ppm 2.30 (d, J=1.1 Hz, 3H) 3.61 (s, 3H) 3.64 (q, J=5.2 Hz, 2H) 3.76-3.90 (m, 2H) 3.96 (s, 3H) 4.76 (t, J=5.6 Hz, 1H) 5.72 (t, J=2.0 Hz, 1H) 5.93 (d, J=2.2 Hz, 2H) 6.13 (d, J=7.9 Hz, 1H) 6.34 (d, J=8.1 Hz, 1H) 6.96 (dd, J=8.3, 1.9 Hz, 1H) 7.09 (d, J=2.0 Hz, 1H) 7.22 (d, J=10.3 Hz, 1H) 7.35 (d, J=8.4 Hz, 1H) 8.01 (d, J=7.7 Hz, 1H) 8.36 (s, 1H) 11.94 (s, 1H)
LC/MS (method LC-B): R$_t$ 2.09 min, MH⁺ 513
[α]$_D^{20}$: +140.8° (c 0.485, DMF)
Chiral SFC (method SFC-A): R$_t$ 3.82 min, MH⁺ 513, chiral purity 100%.
Melting point: 177° C.

Example 10: Synthesis of 2-(4-chloro-2-methoxyphenyl)-1-(3,7-dihydro-2H-furo[3,2-f]indol-5-yl)-2-((3-(2-hydroxyethoxy)-5-methoxyphenyl)amino) ethanone (Compound 10) and chiral separation into Enantiomers 10A and 10B

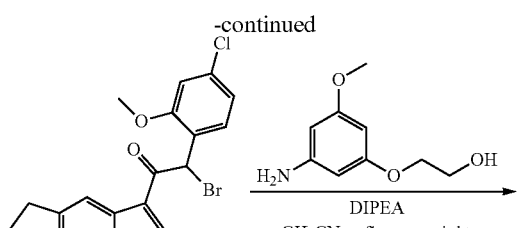

Synthesis of Intermediate 10a:

A solution 3,7-dihydro-2H-furo[3,2-f]indole 7d (1.7 g, 10.7 mmol) in CH₂Cl₂ (150 mL) was cooled on an ice-bath under N₂-atmosphere. A solution of diethylaluminum chloride 1M in hexane (16.1 mL, 16.1 mmol) was added dropwise and the resulting mixture was kept at 0° C. for 15 min. A solution of 2-(4-chloro-2-methoxyphenyl)acetyl chloride 9a' (3.29 g, 15.0 mmol) in CH₂Cl₂ (100 mL) was added dropwise. Stirring was continued at 0° C. for 1 h. The ice-bath was removed and the reaction mixture was stirred at room temperature for 2 h. The reaction mixture was poured out into a stirring ice/Rochelle salt solution. After the ice had melted, the mixture was filtered over Dicalite® and the filter cake was washed several times with THF. The filtrates were combined. The layers were separated and the organic layer was washed with brine and water. The combined aqueous layers were extracted with THF and the combined organic layers were dried over MgSO₄, filtered and evaporated under reduced pressure. The solid residue was suspended in CH₂Cl₂ (20 mL). The precipitate was filtered off, washed with a small amount of CH₂Cl₂ and dried under vacuum at 50° C. to provide 2-(4-chloro-2-methoxyphenyl)-1-(3,7-dihydro-2H-furo[3,2-f]indol-5-yl)ethanone 10a (2.00 g) as a white solid.

Synthesis of Intermediate 10b:

A stirred solution of 2-(4-chloro-2-methoxyphenyl)-1-(3,7-dihydro-2H-furo[3,2-f]indol-5-yl)ethanone 10a (2.00 g, 5.85 mmol) in THF (50 mL) was cooled to 0° C. A solution of phenyltrimethylammonium tribromide [CAS 4207-56-1] (2.42 g, 6.44 mmol) in THF (100 mL) was added dropwise. The reaction mixture was stirred at room temperature for 1 h. The solids were removed by filtration and washed with THF. The combined filtrates were evaporated under reduced pressure. The residue was triturated with a small amount of CH₂Cl₂/heptane (1/1). The solids were isolated by filtration, washed with a small amount of CH₂Cl₂/heptane (1/1) and dried under vacuum at 50° C. to provide 2-bromo-2-(4-chloro-2-methoxyphenyl)-1-(3,7-dihydro-2H-furo[3,2-f]indol-5-yl)ethanone 10b (1.38 g) as a yellow powder.

Synthesis of Compound 10 and Chiral Separation of Enantiomers 10A and 10B:

A mixture of 2-bromo-2-(4-chloro-2-methoxyphenyl)-1-(3,7-dihydro-2H-furo[3,2-f]indol-5-yl)ethanone 10b (1.38 g, 3.27 mmol), 2-(3-amino-5-methoxyphenoxy)-ethanol [CAS 725237-16-1] (1.20 g, 6.54 mmol) and diisopropylethylamine (844 µL, 4.90 mmol) in CH$_3$CN (100 mL) was heated under reflux overnight. The reaction mixture was concentrated under reduced pressure. The residue was dissolved in CH$_2$Cl$_2$, washed with 1N HCl and water, dried over MgSO$_4$, filtered and evaporated under reduced pressure. The residue was purified by column chromatography (Stationary phase: Biotage® SNAP Ultra silica 100 g, Mobile phase: EtOAc:EtOH(3:1)/heptane gradient 0/100 to 70/30). The desired fractions were combined and evaporated under reduced pressure. The residue was dried under vacuum at 50° C. to provide 2-(4-chloro-2-methoxyphenyl)-1-(3,7-dihydro-2H-furo[3,2-f]indol-5-yl)-2-((3-(2-hydroxyethoxy)-5-methoxyphenyl)amino)ethanone (Compound 10, 1.07 g) as a racemic mixture.

The chiral separation of the enantiomers of Compound 10 (1.07 g) was performed via Preparative SFC (Stationary phase: Chiralcel® Diacel OD 20×250 mm, Mobile phase: CO$_2$, EtOH+0.4% iPrNH$_2$). The product fractions were combined and evaporated under reduced pressure to provide Enantiomer 10A as the first eluted product and Enantiomer 10B as the second eluted product. Both enantiomers were further purified via Preparative SFC (Stationary phase: Chiralcel® Diacel AD 20×250 mm, Mobile phase: CO$_2$, EtOH+ 0.4% iPrNH$_2$). The product fractions were combined and evaporated under reduced pressure. Both enantiomers were crystallized from a mixture of MeOH (5 mL) and water (2 mL). The solids were isolated by filtration, washed with a small amount of MeOH/water (1/1) and dried under vacuum at 50° C. to provide Enantiomer 10A (240 mg) and Enantiomer 10B (200 mg) as white powders.

Enantiomer 10A:

$^1$H NMR (360 MHz, DMSO-d$_6$) δ ppm 3.21 (br t, J=8.4 Hz, 2H) 3.60 (s, 3H) 3.64 (q, J=5.4 Hz, 2H) 3.76-3.88 (m, 2H) 3.97 (s, 3H) 4.52 (t, J=8.8 Hz, 2H) 4.80 (t, J=5.5 Hz, 1H) 5.70 (t, J=2.0 Hz, 1H) 5.92 (d, J=1.8 Hz, 2H) 6.10 (d, J=8.1 Hz, 1H) 6.36 (d, J=8.1 Hz, 1H) 6.76 (s, 1H) 6.95 (dd, J=8.2, 2.0 Hz, 1H) 7.09 (d, J=1.8 Hz, 1H) 7.34 (d, J=8.1 Hz, 1H) 7.94 (s, 1H) 8.22 (s, 1H) 11.74 (br s, 1H)

LC/MS (method LC-A): R$_t$ 1.00 min, MH$^+$ 523

[α]$_D^{20}$: −166.0° (c 0.365, DMF)

Chiral SFC (method SFC-A): R$_t$ 4.90 min, MH$^+$ 523, chiral purity 100%.

Melting point: 215° C.

Enantiomer 10B:

$^1$H NMR (360 MHz, DMSO-d$_6$) δ ppm 3.22 (br t, J=8.4 Hz, 2H) 3.60 (s, 3H) 3.64 (q, J=5.1 Hz, 2H) 3.76-3.88 (m, 2H) 3.97 (s, 3H) 4.52 (t, J=9.0 Hz, 2H) 4.80 (t, J=5.5 Hz, 1H) 5.70 (t, J=2.0 Hz, 1H) 5.92 (d, J=2.2 Hz, 2H) 6.10 (d, J=8.1 Hz, 1H) 6.36 (d, J=8.4 Hz, 1H) 6.76 (s, 1H) 6.95 (dd, J=8.2, 2.0 Hz, 1H) 7.09 (d, J=1.8 Hz, 1H) 7.34 (d, J=8.1 Hz, 1H) 7.94 (s, 1H) 8.22 (s, 1H) 11.74 (br s, 1H)

LC/MS (method LC-A): R$_t$ 1.01 min, MH$^+$ 523

[α]$_D^{20}$: +166.7° (c 0.45, DMF)

Chiral SFC (method SFC-A): R$_t$ 4.66 min, MH$^+$ 523, chiral purity 100%.

Melting point: 216° C.

Example 11: Synthesis of 2-(4-chloro-2-methoxyphenyl)-1-(7,8-dihydro-1H-furo[2,3-g]indol-3-yl)-2-((3-(2-hydroxyethoxy)-5-methoxyphenyl)amino) ethanone (Compound 11) and chiral separation into Enantiomers 11A and 11B

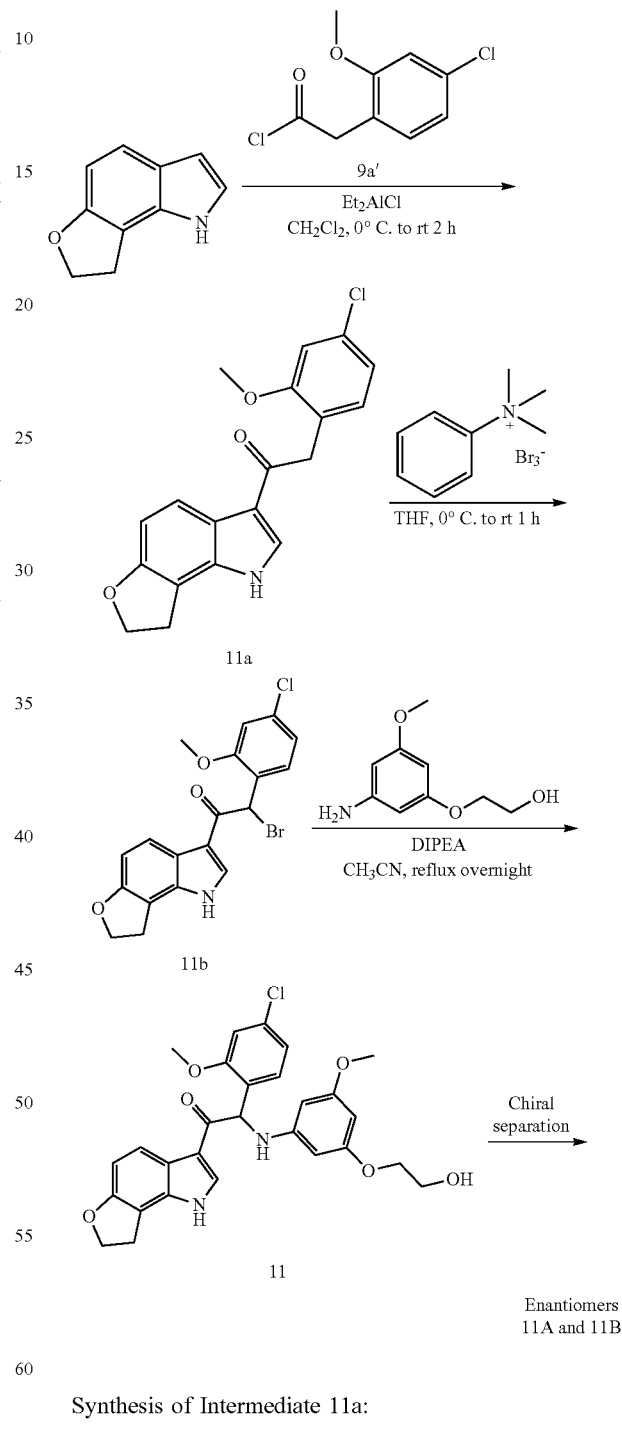

Synthesis of Intermediate 11a:

A solution 7,8-dihydro-1H-furo[2,3-g]indole [CAS 170728-95-7] (1.71 g, 10.7 mmol) in CH$_2$Cl$_2$ (150 mL) was cooled to 0° C. under N$_2$-atmosphere. A solution of diethylaluminum chloride 1M in hexane (16.1 mL, 16.1 mmol) was added dropwise and the resulting mixture was kept at 0°

C. for 15 min. A solution of 2-(4-chloro-2-methoxyphenyl)acetyl chloride 9a' (3.29 g, 15.0 mmol) in $CH_2Cl_2$ (100 mL) was added dropwise. The reaction mixture was stirred at 0° C. for 1 h, and subsequently at room temperature for 2 h. The reaction mixture was poured out into a stirring ice/Rochelle salt solution. After the ice had melted, the mixture was filtered over Dicalite® and the filter cake was washed several times with THF. The filtrates were combined. The layers were separated and the organic layer was washed with brine and water. The combined aqueous layers were extracted with THF and the combined organic layers were dried over $MgSO_4$, filtered and evaporated under reduced pressure. The solid residue was suspended in $CH_2Cl_2$ (20 mL). The precipitate was filtered off, washed with a small amount of $CH_2Cl_2$ and dried under vacuum at 50° C. to provide 2-(4-chloro-2-methoxyphenyl)-1-(7,8-dihydro-1H-furo[2,3-g]indol-3-yl)ethanone 11a (2.00 g).

Synthesis of Intermediate 11b:

A stirred solution of 2-(4-chloro-2-methoxyphenyl)-1-(7,8-dihydro-1H-furo[2,3-g]indol-3-yl)ethanone 11a (2.00 g, 5.85 mmol) in THF (50 mL) was cooled to 0° C. A solution of phenyltrimethylammonium tribromide [CAS 4207-56-1] (2.42 g, 6.44 mmol) in THF (100 mL) was added dropwise. The reaction mixture was stirred at room temperature for 1 h. The solids were removed by filtration and washed with THF. The combined filtrates were evaporated under reduced pressure. The residue was triturated with a small amount of $CH_2Cl_2$/heptane (1/1). The solids were isolated by filtration, washed with a small amount of $CH_2Cl_2$/heptane (1/1) and dried under vacuum at 50° C. to provide 2-bromo-2-(4-chloro-2-methoxyphenyl)-1-(7,8-dihydro-1H-furo[2,3-g]indol-3-yl)ethanone 11 b (1.63 g) as a solid.

Synthesis of Compound 11 and Chiral Separation of Enantiomers 11A and 11B:

A mixture of 2-bromo-2-(4-chloro-2-methoxyphenyl)-1-(7,8-dihydro-1H-furo[2,3-g]indol-3-yl)ethanone 11b (1.63 g, 3.88 mmol), 2-(3-amino-5-methoxyphenoxy)ethanol [CAS 725237-16-1] (1.42 g, 7.75 mmol) and diisopropylethylamine (1.00 mL, 5.81 mmol) in $CH_3CN$ (100 mL) was heated under reflux overnight. The reaction mixture was concentrated under reduced pressure. The residue was dissolved in $CH_2Cl_2$, washed with 1N HCl and water, dried over $MgSO_4$, filtered and evaporated under reduced pressure. The residue was purified by column chromatography (Stationary phase: Biotage® SNAP Ultra silica 100 g, Mobile phase: EtOAc:EtOH(3:1)/heptane gradient 0/100 to 70/30). The desired fractions were combined and evaporated under reduced pressure. The residue was dried under vacuum at 50° C. to provide 2-(4-chloro-2-methoxyphenyl)-1-(7,8-dihydro-1H-furo[2,3-g]indol-3-yl)-2-((3-(2-hydroxyethoxy)-5-methoxyphenyl)amino)ethanone (Compound 11, 886 mg) as a racemic mixture.

The chiral separation of the enantiomers of Compound 11 (886 mg) was performed via Preparative SFC (Stationary phase: Chiralpak® Diacel AS 20×250 mm, Mobile phase: $CO_2$, EtOH+0.4% $iPrNH_2$). The product fractions were combined and evaporated under reduced pressure to provide Enantiomer 11A as the first eluted product and Enantiomer 11B as the second eluted product. Enantiomer 11A was further purified by column chromatography (Stationary phase: Biotage® SNAP Ultra silica 25 g, Mobile phase: EtOAc:EtOH (3:1)/heptane gradient 0/100 to 70/30). The product fractions were combined and evaporated under reduced pressure. The solid residue was dried under vacuum at 50° C. to provide Enantiomer 11A (279 mg). Enantiomer 11B was purified by Preparative SFC (Stationary phase: Chiralpak® Diacel AD 20×250 mm, Mobile phase: $CO_2$, EtOH+0.4% $iPrNH_2$). The product fractions were combined and evaporated under reduced pressure. The residue was further purified by column chromatography (Stationary phase: Biotage® SNAP Ultra silica 25 g, Mobile phase: EtOAc:EtOH(3:1)/heptane gradient 0/100 to 70/30). The product fractions were combined and evaporated under reduced pressure. The solid residue was washed with MeOH and dried under vacuum at 50° C. to provide Enantiomer 11B (260 mg) as a white powder.

Enantiomer 11A:

$^1$H NMR (360 MHz, DMSO-$d_6$) δ ppm 3.24-3.31 (m, 2H) 3.60 (s, 3H) 3.62-3.68 (m, 2H) 3.75-3.89 (m, 2H) 3.97 (s, 3H) 4.57 (t, J=9.0 Hz, 2H) 4.80 (br s, 1H) 5.70 (t, J=2.0 Hz, 1H) 5.93 (d, J=2.2 Hz, 2H) 6.13 (d, J=7.7 Hz, 1H) 6.38 (d, J=8.1 Hz, 1H) 6.70 (d, J=8.4 Hz, 1H) 6.95 (dd, J=8.2, 2.0 Hz, 1H) 7.08 (d, J=1.8 Hz, 1H) 7.35 (d, J=8.1 Hz, 1H) 7.89 (d, J=8.4 Hz, 1H) 8.33 (s, 1H) 12.23 (br s, 1H)

LC/MS (method LC-A): $R_t$ 1.00 min, MH$^+$ 523

$[α]_D^{20}$: +67.5° (c 0.385, DMF)

Chiral SFC (method SFC-A): $R_t$ 4.23 min, MH$^+$ 523, chiral purity 100%.

Enantiomer 11B:

$^1$H NMR (360 MHz, DMSO-$d_6$) δ ppm 3.26-3.31 (m, 2H) 3.61 (s, 3H) 3.62-3.67 (m, 2H) 3.72-3.91 (m, 2H) 3.97 (s, 3H) 4.58 (t, J=8.8 Hz, 2H) 4.81 (br t, J=4.9 Hz, 1H) 5.71 (t, J=1.8 Hz, 1H) 5.94 (d, J=1.8 Hz, 2H) 6.14 (d, J=8.1 Hz, 1H) 6.39 (d, J=8.1 Hz, 1H) 6.71 (d, J=8.4 Hz, 1H) 6.96 (dd, J=8.4, 1.8 Hz, 1H) 7.09 (d, J=1.8 Hz, 1H) 7.35 (d, J=8.1 Hz, 1H) 7.90 (d, J=8.8 Hz, 1H) 8.33 (s, 1H) 11.98 (br s, 1H)

LC/MS (method LC-A): $R_t$ 1.00 min, MH$^+$ 523

$[α]_D^{20}$: −71.2° (c 0.400, DMF)

Chiral SFC (method SFC-A): $R_t$ 4.75 min, MH$^+$ 523, chiral purity 100%.

Example 12: Synthesis 2-(4-chloro-2-methoxyphenyl)-1-(4-fluoro-6-methoxy-5-methyl-1H-indol-3-yl)-2-((3-(2-hydroxyethoxy)-5-methoxyphenyl)amino)ethanone (Compound 12) and chiral separation into Enantiomers 12A and 12B

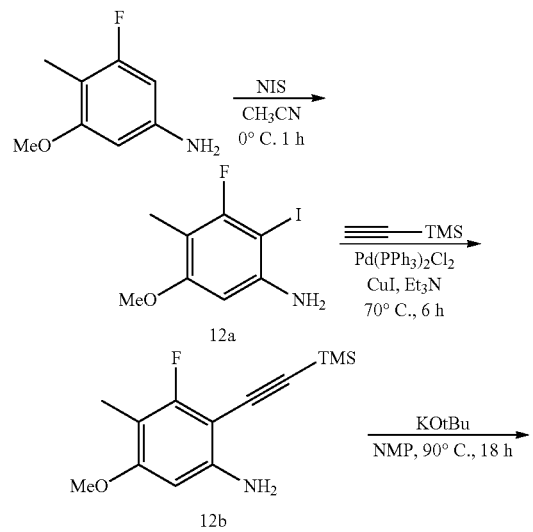

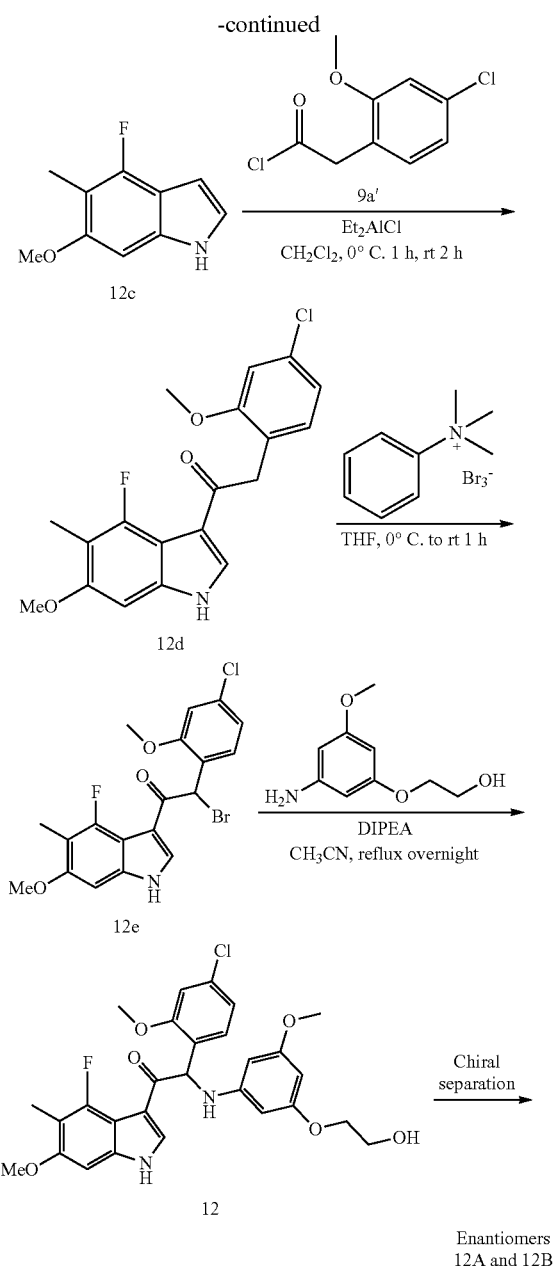

Synthesis of Intermediate 12a:

N-iodosuccinimide (62.2 g, 276 mmol) was added to a cooled (0° C.) solution of 3-fluoro-5-methoxy-4-methylaniline [CAS 1357103-764] (39 g, 251 mmol) in CH$_3$CN (300 mL), and the reaction mixture was stirred at 0° C. for 1 h. The reaction mixture was diluted with EtOAc (500 mL), washed with water (500 mL) and brine (500 mL), dried over MgSO$_4$, filtered and concentrated under reduced pressure. The residue was purified by column chromatography on silica gel (gradient 0 to 10% EtOAc in petroleum ether) to provide 3-fluoro-2-iodo-5-methoxy-4-methylaniline 12a (37 g) as a gray solid.

Synthesis of Intermediate 12b:

A mixture of 3-fluoro-2-iodo-5-methoxy-4-methylaniline 12a (37 g, 132 mmol), Copper(I) iodide (1.46 g, 7.68 mmol), bis(triphenylphosphine)palladium(II) chloride (3.70 g, 5.27 mmol) and trimethylsilylacetylene (54.6 mL, 395 mmol) in triethylamine (500 mL) was heated at 70° C. for 6 h under N$_2$-atmosphere. The reaction mixture was concentrated under reduced pressure. The residue was suspended in water (500 mL) and extracted with EtOAc (2×500 mL). The combined organic layers were washed with brine (2×500 mL), dried over MgSO$_4$, filtered and concentrated under reduced pressure. The residue was purified by column chromatography on silica gel (gradient: 0 to 8% EtOAc in petroleum ether) to provide 3-fluoro-5-methoxy-4-methyl-2-((trimethylsilyl)ethynyl)aniline 12b (20 g) as gray solid.

Synthesis of Intermediate 12c:

Potassium tert-butoxide (23.8 g, 212 mmol) was added to a solution of 3-fluoro-5-methoxy-4-methyl-2-((trimethylsilyl)ethynyl)aniline 12b (20 g, 60.5 mmol) in NMP (500 mL) at room temperature. The reaction mixture was stirred at 90° C. for 18 h. The reaction was diluted with H$_2$O (800 mL) and extracted with EtOAc (2×700 mL). The combined organic layers were washed with brine (3×1 L), dried over MgSO$_4$, filtered and concentrated under reduced pressure. The residue was purified by column chromatography on silica gel (gradient: 0 to 15% EtOAc in petroleum ether) to give 4-fluoro-6-methoxy-5-methyl-1H-indole 12c (9.00 g) as a yellow solid.

Synthesis of Intermediate 12d:

Diethylaluminum chloride 1M in hexane (16.1 mL, 16.1 mmol) was added dropwise, to a cooled (0° C.) solution of 4-fluoro-6-methoxy-5-methyl-1H-indole 12c (1.92 g, 10.7 mmol) in CH$_2$Cl$_2$ (150 mL) under a N$_2$-atmosphere. After stirring for 15 min at 0° C., a solution of 2-(4-chloro-2-methoxyphenyl)acetyl chloride 9a' (3.29 g, 15.0 mmol) in CH$_2$Cl$_2$ (100 mL) was added dropwise to the reaction mixture. Stirring was continued at 0° C. for 1 h and the mixture was allowed to warm to room temperature while stirring for 2 h. The reaction mixture was poured out into ice-water containing excess Rochelle salt. After warming to room temperature, the mixture was filtered on a short pad of Dicalite® and the filter cake was rinsed several times with THF. The layers were separated. The organic layer was washed with brine and water, dried over MgSO$_4$, filtered, and evaporated under reduced pressure. The solid residue was suspended in CH$_2$Cl$_2$ (20 mL) and the solids were filtered off, washed with a small amount of CH$_2$Cl$_2$ and dried under vacuum at 50° C. to give 2-(4-chloro-2-methoxyphenyl)-1-(4-fluoro-6-methoxy-5-methyl-1H-indol-3-yl)ethanone 12d (582 mg).

Synthesis of Intermediate 12e:

A solution of phenyltrimethylammonium tribromide [CAS 4207-56-1] (665 mg, 1.77 mmol) in THF (50 mL) was added dropwise to a cooled (0° C.) solution of 2-(4-chloro-2-methoxyphenyl)-1-(4-fluoro-6-methoxy-5-methyl-1H-indol-3-yl)ethanone 12d (582 mg, 1.62 mmol) in THF (50 mL), and the reaction mixture was allowed to warm to room temperature while stirring for 1 h. The reaction mixture was filtered and the solids were washed with THF. The filtrate was evaporated under reduced pressure. The residual brown solid was triturated with a small amount of CH$_2$Cl$_2$/heptane (1/1). The solids were filtered off and washed with CH$_2$Cl$_2$/heptane (1/1) to give 2-bromo-2-(4-chloro-2-methoxyphenyl)-1-(4-fluoro-6-methoxy-5-methyl-1H-indol-3-yl)ethanone 12e (725 mg) as a white solid. The product was used without further purification in the next step.

Synthesis of Compound 12 and Chiral Separation into Enantiomers 12A and 12B:

A mixture of 2-bromo-2-(4-chloro-2-methoxyphenyl)-1-(4-fluoro-6-methoxy-5-methyl-1H-indol-3-yl)ethanone 12e (725 mg, 0.82 mmol), 2-(3-amino-5-methoxyphenoxy)ethanol [CAS 725237-16-1] (452 mg, 2.47 mmol) and diisopropylethylamine (425 μL, 2.47 mmol) in CH₃CN (50 mL) was heated under reflux overnight. After cooling to room temperature, the solvent was evaporated under reduced pressure. The residue was dissolved in CH₂Cl₂. The organic solution was washed with 1N HCl, water, dried over MgSO₄, filtered, and evaporated under reduced pressure. The residue was purified by column chromatography (Stationary phase: Biotage® SNAP Ultra 50 g, Mobile phase: EtOAc:EtOH(3:1)/heptane gradient 0/100 to 70/30). The product fractions were combined and evaporated under reduced pressure. The residue (243 mg) was further purified via Preparative HPLC (Stationary phase: Uptisphere® C18 ODB—10 μm, 200 g, 5 cm, Mobile phase: 0.25% NH₄HCO₃ solution in water, CH₃CN). The product fractions were combined and evaporated under reduced pressure to provide racemic 2-(4-chloro-2-methoxyphenyl)-1-(4-fluoro-6-methoxy-5-methyl-1H-indol-3-yl)-2-((3-(2-hydroxyethoxy)-5-methoxyphenyl)amino)ethanone (Compound 12, 110 mg).

The enantiomers of Compound 12 (110 mg) were separated via Preparative SFC (Stationary phase: Chiralcel® Diacel OD 20×250 mm, Mobile phase: CO₂, EtOH+0.4% iPrNH₂). The product fractions were combined and evaporated under reduced pressure to provide Enantiomer 12A as the first eluted product and Enantiomer 12B as the second eluted product. Both enantiomers were further purified by column chromatography (Biotage® SNAP Ultra silica 10 g, eluent: EtOAc:EtOH(3:1)/heptane gradient 0/100 to 50/50). The product fractions were combined and evaporated under reduced pressure. The solid residues were dried under vacuum at 50° C. to provide Enantiomer 12A (35 mg) and Enantiomer 12B (44 mg) as a white powders.

Enantiomer 12A:
¹H NMR (360 MHz, DMSO-d₆) δ ppm 2.09 (d, J=2.2 Hz, 3H) 3.61 (s, 3H) 3.64 (q, J=5.2 Hz, 2H) 3.75-3.89 (m, 5H) 3.93 (s, 3H) 4.80 (t, J=5.5 Hz, 1H) 5.70 (t, J=2.0 Hz, 1H) 5.94 (d, J=1.8 Hz, 2H) 6.16 (d, J=8.1 Hz, 1H) 6.37 (d, J=8.1 Hz, 1H) 6.77 (s, 1H) 6.96 (dd, J=8.4, 1.8 Hz, 1H) 7.06 (d, J=2.2 Hz, 1H) 7.32 (d, J=8.4 Hz, 1H) 8.31 (s, 1H) 11.98 (br s, 1H)
LC/MS (method LC-A): $R_t$ 1.06 min, MH⁺ 543
$[\alpha]_D^{20}$: −110.4° (c 0.365, DMF)
Chiral SFC (method SFC-A): $R_t$ 4.20 min, MH⁺ 543, chiral purity 100%. Enantiomer 12B:
¹H NMR (360 MHz, DMSO-d₆) δ ppm 2.09 (d, J=2.6 Hz, 3H) 3.61 (s, 3H) 3.64 (q, J=5.1 Hz, 2H) 3.75-3.89 (m, 5H) 3.93 (s, 3H) 4.80 (t, J=5.5 Hz, 1H) 5.70 (t, J=2.0 Hz, 1H) 5.94 (d, J=2.2 Hz, 2H) 6.16 (d, J=7.7 Hz, 1H) 6.37 (d, J=8.1 Hz, 1H) 6.77 (s, 1H) 6.96 (dd, J=8.2, 2.0 Hz, 1H) 7.06 (d, J=1.8 Hz, 1H) 7.32 (d, J=8.1 Hz, 1H) 8.31 (s, 1H) 11.98 (br s, 1H)
LC/MS (method LC-A): $R_t$ 1.07 min, MH⁺ 543
$[\alpha]_D^{20}$: +123.7° (c 0.41, DMF)
Chiral SFC (method SFC-A): $R_t$ 3.97 min, MH⁺ 543, chiral purity 100%.

Example 13.1: Synthesis of 2-(3-((1-(4-chloro-2-methoxyphenyl)-2-(6-fluoro-1H-indol-3-yl)-2-oxoethyl)amino)-5-methoxyphenoxy)ethyl dihydrogen phosphate (Compound 13-P) and chiral separation into Enantiomers 13A-P and 13B-P

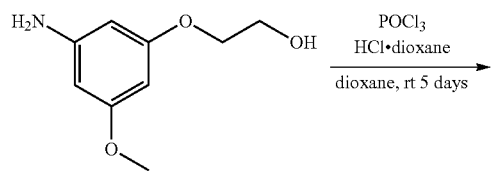

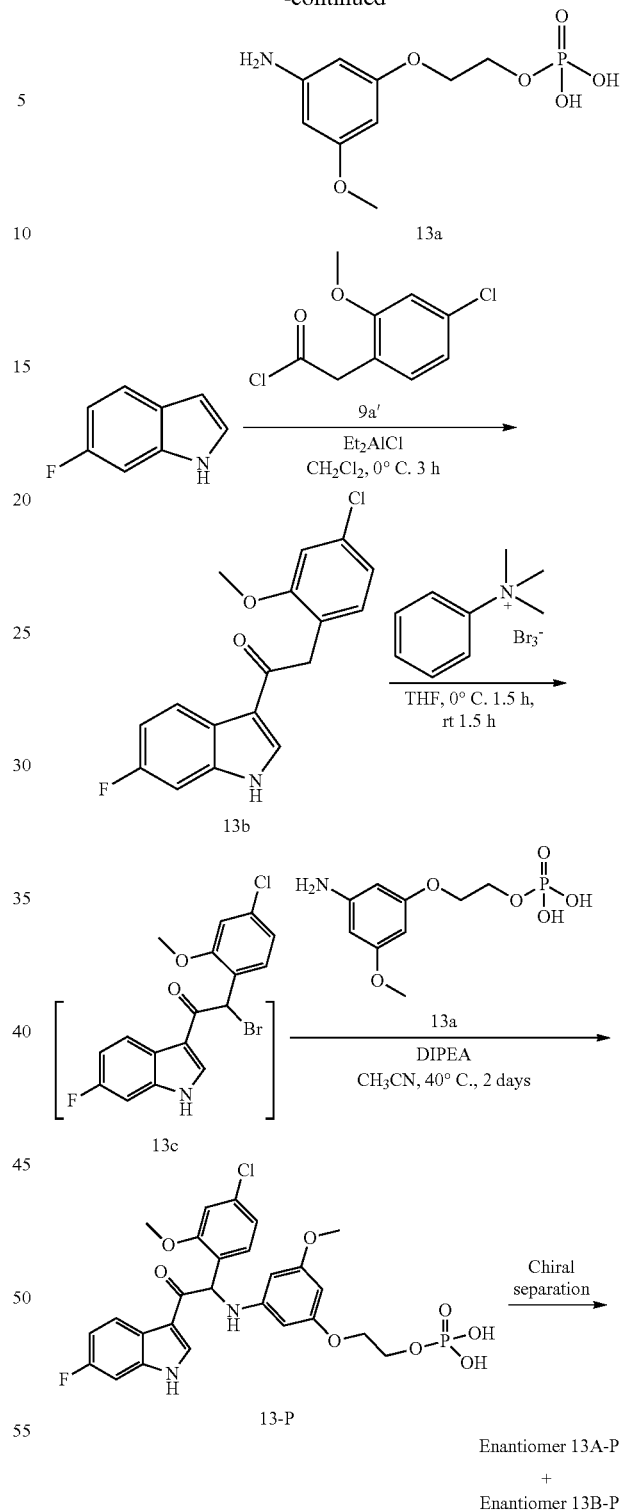

Synthesis of Intermediate 13a:
4M HCl in dioxane (7.5 mL, 30 mmol) was added dropwise to a stirred solution of 2-(3-amino-5-methoxyphenoxy)ethanol [CAS 725237-16-1] (5.0 g, 27.3 mmol) in dioxane (175 mL) under N₂-atmosphere. The resulting white mixture was vigorously stirred for 15 minutes. Phosphorous oxychloride (7.6 mL, 82 mmol) was added slowly, and the reaction mixture was stirred at room temperature for 5 days.

The reaction mixture was poured out into ice-water (200 mL). After stirring for 1 h, the solvent was concentrated under reduced pressure to a residual volume of ~100 mL. Et$_2$O (75 mL) was added, causing precipitation. The solids were removed by filtration, washed with water and discarded. The filtrate was purified via preparative HPLC (Stationary phase: RP XBridge® Prep C18 OBD—10 μm, 50×150 mm, Mobile phase: water, CH$_3$CN). The fractions containing product 13a were combined. Evaporation of the organic volatiles under reduced pressure caused precipitation of the product in multiple consecutive crops. The solids were isolated by filtration and dried at 50° C. under vacuum to provide 2-(3-amino-5-methoxyphenoxy)ethyl dihydrogen phosphate 13a (total amount (4 crops): 1.83 g).

Synthesis of Intermediate 13b:

Diethylaluminum chloride 1M in hexane (37.1 mL, 37.1 mmol) was added dropwise at 0° C. to a solution of 6-fluoro-1H-indole [CAS 399-51-9] (3.34 g, 24.8 mmol) in CH$_2$Cl$_2$ (100 mL). After stirring for 30 min at 0° C., a solution of 2-(4-chloro-2-methoxyphenyl)acetyl chloride 9a' (6.3 g, 28.8 mmol) in CH$_2$Cl$_2$ (100 mL) was added slowly at 0° C. The reaction was stirred at 0° C. for 3 h. Ice-water was added and the precipitate was filtered off, washed with water and a small amount of CH$_2$Cl$_2$. The solids were dried under vacuum at 70° C. overnight to give 2-(4-chloro-2-methoxyphenyl)-1-(6-fluoro-1H-indol-3-yl)ethanone 13b (4.9 g).

Synthesis of Compound 13-P and Chiral Separation into Enantiomers 13A-P and 13B-P:

At 0° C., phenyltrimethylammonium tribromide [CAS 4207-56-1] (1.63 g, 4.33 mmol) was added in portions to a stirred solution of 2-(4-chloro-2-methoxyphenyl)-1-(6-fluoro-1H-indol-3-yl)ethanone 13b (1.31 g, 4.12 mmol) in THF (40 mL). The reaction mixture was stirred at 0° C. for 90 min and at room temperature for 90 min. The precipitate was filtered off and washed with THF (2×). The combined filtrated were added to a solution of diisopropylethylamine (4.26 mL, 24.7 mmol) in CH$_3$CN (40 mL) and DMF (20 mL). 13a (1.62 g, 5.42 mmol) was added and the reaction mixture was stirred at room temperature for 90 min and at 40° C. for 2 days. The volatiles were evaporated under reduced pressure. The residue was purified via preparative HPLC (Stationary phase: RP XBridge® Prep C18 OBD—10 μm, 50×150 mm, Mobile phase: 0.25% NH$_4$HCO$_3$ solution in water, CH$_3$CN). The product fractions were combined and co-evaporated with xylene under reduced pressure. The residue was dried under vacuum at 45° C. for 65 hours, stirred up in CH$_3$CN, filtered off, washed with CH$_3$CN (3×), and dried under vacuum at 45° C. to provide 2-(3-((1-(4-chloro-2-methoxyphenyl)-2-(6-fluoro-1H-indol-3-yl)-2-oxoethyl)amino)-5-methoxyphenoxy)ethyl dihydrogen phosphate (Compound 13-P, 800 mg) as a racemic mixture.

The enantiomers of Compound 13-P were separated via Chiral SFC (Stationary phase: Chiralpak® Daicel ID 20×250 mm, Mobile phase: CO$_2$, EtOH+0.4% iPrNH$_2$). The fractions containing product were combined and evaporated under reduced pressure to provide 13A-P as the first eluted enantiomer and 13B-P as the second eluted enantiomer. The first eluted enantiomer was further purified via preparative SFC (Stationary phase: Chiralpak® Daicel ID 20×250 mm, Mobile phase: CO$_2$, EtOH+0.4% iPrNH$_2$). The desired fractions were combined, evaporated under reduced pressure and co-evaporated with EtOAc. The residual solid was dried under vacuum at 45° C. to provide Enantiomer 13A-P (148 mg, iPrNH$_2$-salt). The second eluted enantiomer was taken up with DIPE/EtOAc (5/1). The solids were filtered off, washed with DIPE (5×) and dried under vacuum at 45° C. to give Enantiomer 13B-P (266 mg, iPrNH$_2$-salt).

Compound 13-P:

$^1$H NMR (400 MHz, DMSO-d$_6$) δ ppm 3.60 (s, 3H) 3.84-4.04 (m, 7H) 5.72 (t, J=2.0 Hz, 1H) 5.92-6.00 (m, 2H) 6.16 (d, J=8.1 Hz, 1H) 6.38 (d, J=8.4 Hz, 1H) 6.96 (dd, J=8.3, 1.9 Hz, 1H) 6.99-7.08 (m, 2H) 7.26 (dd, J=9.7, 2.4 Hz, 1H) 7.40 (d, J=8.4 Hz, 1H) 8.12 (dd, J=8.8, 5.7 Hz, 1H) 8.47 (s, 1H)

LC/MS (method LC-A): R$_t$ 0.81 min, MH$^-$ 577

Enantiomer 13A-P:

$^1$H NMR (400 MHz, DMSO-d$_6$) δ ppm 1.14 (d, J=6.6 Hz, 6H) 3.20 (dt, J=12.8, 6.2 Hz, 1H) 3.60 (s, 3H) 3.87-3.99 (m, 7H) 5.72 (t, J=2.0 Hz, 1H) 5.93-5.98 (m, 2H) 6.16 (d, J=8.4 Hz, 1H) 6.38 (d, J=8.4 Hz, 1H) 6.96 (dd, J=8.1, 2.0 Hz, 1H) 6.99-7.07 (m, 2H) 7.26 (dd, J=9.7, 2.4 Hz, 1H) 7.40 (d, J=8.4 Hz, 1H) 8.12 (dd, J=8.8, 5.5 Hz, 1H) 8.46 (s, 1H)

LC/MS (method LC-B): R$_t$ 1.51 min, MH$^-$ 577

[α]$_D^{20}$: +68.3° (c 0.445, DMF)

Chiral SFC (method SFC-F): R$_t$ 1.48 min, MH$^+$ 579, chiral purity 100%.

Enantiomer 13B-P:

$^1$H NMR (400 MHz, DMSO-d$_6$) δ ppm 1.15 (d, J=6.4 Hz, 6H) 3.17-3.25 (m, 1H) 3.60 (s, 3H) 3.86-4.00 (m, 7H) 5.72 (t, J=2.0 Hz, 1H) 5.96 (br d, J=7.9 Hz, 2H) 6.16 (d, J=8.4 Hz, 1H) 6.38 (d, J=8.4 Hz, 1H) 6.96 (dd, J=8.3, 1.9 Hz, 1H) 6.99-7.08 (m, 2H) 7.26 (dd, J=9.6, 2.3 Hz, 1H) 7.40 (d, J=8.1 Hz, 1H) 8.12 (dd, J=8.7, 5.6 Hz, 1H) 8.47 (s, 1H)

LC/MS (method LC-B): R$_t$ 1.51 min, MH$^-$ 577

[α]$_D^{20}$: −69.5° (c 0.525, DMF)

Chiral SFC (method SFC-F): R$_t$ 2.49 min, MH$^+$ 579, chiral purity 100%.

Example 13.2: Alternative Procedure for the Synthesis of Enantiomer 13A-P

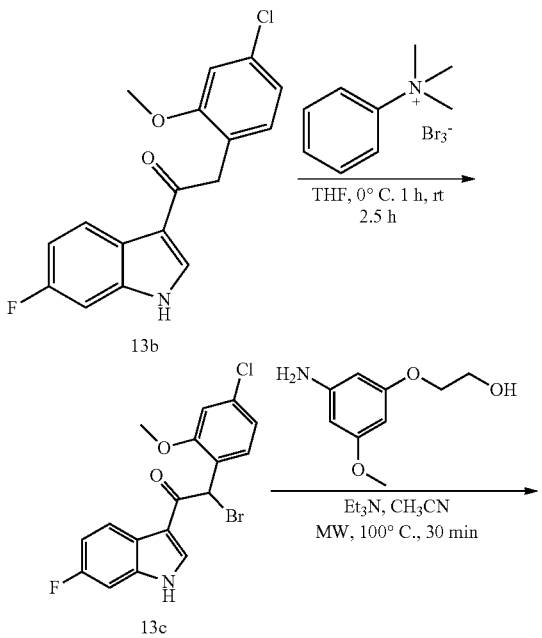

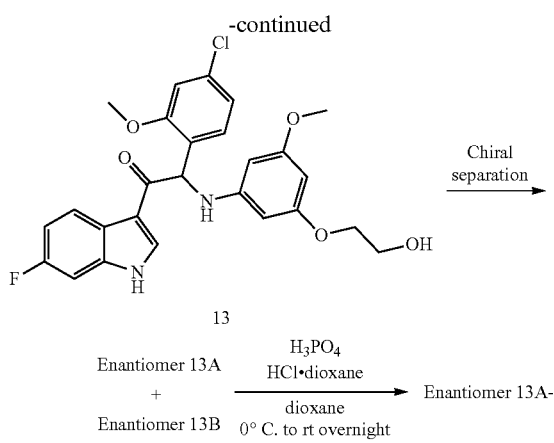

Synthesis of Intermediate 13c:

At 0° C., a solution of phenyltrimethylammonium tribromide [CAS 4207-56-1] (5.8 g, 15.4 mmol) in THF (65 mL) was added dropwise to a mixture of 2-(4-chloro-2-methoxyphenyl)-1-(6-fluoro-1H-indol-3-yl)ethanone 13b (4.9 g, 15.4 mmol) in THF (60 mL). The mixture was stirred at 0° C. for 1 h and at room temperature for 2.5 h. The precipitate was filtered off and washed with EtOAc. The combined filtrates were concentrated under reduced pressure. The residue was taken up with EtOAc and washed with water. A precipitate appeared in the organic layer and was filtered off and dried to provide a first batch of 2-bromo-2-(4-chloro-2-methoxyphenyl)-1-(6-fluoro-1H-indol-3-yl)ethanone 13c (4.6 g). The organic layer was separated, dried over MgSO$_4$, filtered and the solvent was evaporated under reduced pressure. The residue was crystallized from EtOAc. The precipitate was filtered off, washed with Et$_2$O and dried under vacuum to provide a second fraction of 2-bromo-2-(4-chloro-2-methoxyphenyl)-1-(6-fluoro-1H-indol-3-yl)ethanone 13c (1.6 g).

Synthesis of Compound 13 and Chiral Separation into Enantiomers 13A and 13B:

A mixture of 2-bromo-2-(4-chloro-2-methoxyphenyl)-1-(6-fluoro-1H-indol-3-yl)ethanone 13c (2.1 g, 5.3 mmol), 2-(3-amino-5-methoxyphenoxy)ethanol [CAS 725237-16-1] (924 mg, 5.05 mmol) and triethylamine (1.47 mL, 10.6 mmol) in CH$_3$CN (16 mL) was heated in a sealed tube at 100° C. for 30 min using a microwave Biotage® Initiator EXP 60 with a power output ranging from 0 to 400 W (fixed hold time). The reaction was diluted with CH$_2$Cl$_2$ and the organic layer was washed with water, dried over MgSO$_4$, filtered and the solvent was concentrated under reduced pressure. The residue was purified by flash chromatography on silica gel (15-40 µm, 80 g) using a heptane/EtOAc gradient of 50/50 to 0/100. The pure fractions were combined and concentrated to give 1.1 g of Compound 13. This fraction was combined with another batch of 0.93 g of Compound 13 and subsequently purified via achiral SFC (Stationary phase: CYANO 6 µm 150×21.2 mm, Mobile phase: 75% CO$_2$, 25% MeOH) to provide 2-(4-chloro-2-methoxyphenyl)-1-(6-fluoro-1H-indol-3-yl)-2-((3-(2-hydroxyethoxy)-5-methoxyphenyl)amino)ethanone (Compound 13, 1.36 g) as a racemic mixture.

The enantiomers of Compound 13 (1.36 g) were separated via Chiral SFC (Stationary phase: Chiralcel® OJ 20×250 mm, Mobile phase: 60% CO$_2$, 40% MeOH) yielding 611 mg of the first eluted enantiomer and 586 mg of the second eluted enantiomer. The first eluted enantiomer was taken up with CH$_3$CN/diisopropyl ether/heptane. The precipitate was filtered off and dried to give Enantiomer 13A (496 mg) as an amorphous powder. The second eluted enantiomer was taken up with CH$_3$CN/diisopropyl ether/heptane. The precipitate was filtered off and dried to give Enantiomer 13B (458 mg) as an amorphous powder.

Compound 13:

$^1$H NMR (500 MHz, DMSO-d$_6$) δ ppm 3.61 (s, 3H) 3.64 (q, J=5.3 Hz, 2H) 3.77-3.88 (m, 2H) 3.96 (s, 3H) 4.78 (t, J=5.5 Hz, 1H) 5.71 (t, J=1.9 Hz, 1H) 5.93 (d, J=1.9 Hz, 2H) 6.15 (d, J=8.2 Hz, 1H) 6.40 (d, J=8.2 Hz, 1H) 6.96 (dd, J=8.2, 1.9 Hz, 1H) 7.02-7.08 (m, 1H) 7.09 (d, J=1.9 Hz, 1H) 7.27 (dd, J=9.6, 2.4 Hz, 1H) 7.35 (d, J=8.5 Hz, 1H) 8.13 (dd, J=8.8, 5.7 Hz, 1H) 8.43 (s, 1H) 11.96-12.17 (m, 1H)

LC/MS (method LC-C): R$_t$ 2.95 min, MH$^+$ 499

Enantiomer 13A:

$^1$H NMR (500 MHz, DMSO-d$_6$) δ ppm 3.57-3.68 (m, 5H) 3.77-3.89 (m, 2H) 3.96 (s, 3H) 4.73-4.87 (m, 1H) 5.71 (t, J=1.9 Hz, 1H) 5.91-5.96 (m, 2H) 6.15 (d, J=8.2 Hz, 1H) 6.39 (d, J=8.2 Hz, 1H) 6.96 (dd, J=8.2, 1.9 Hz, 1H) 7.01-7.11 (m, 2H) 7.27 (dd, J=9.6, 2.4 Hz, 1H) 7.36 (d, J=8.2 Hz, 1H) 8.13 (dd, J=9.6, 5.7 Hz, 1H) 8.43 (s, 1H) 11.45-12.31 (m, 1H)

LC/MS (method LC-C): R$_t$ 2.95 min, MH$^+$ 499

$[\alpha]_D^{20}$: +112.1° (c 0.281, DMF)

Chiral SFC (method SFC-D): R$_t$ 3.17 min, MH$^+$ 499, chiral purity 100%.

Enantiomer 13B:

$^1$H NMR (500 MHz, DMSO-d$_6$) δ ppm 3.57-3.67 (m, 5H) 3.74-3.90 (m, 2H) 3.96 (s, 3H) 4.78 (br. s., 1H) 5.70-5.74 (m, 1H) 5.93 (s, 2H) 6.15 (d, J=8.2 Hz, 1H) 6.40 (d, J=8.2 Hz, 1H) 6.96 (dd, J=8.2, 1.9 Hz, 1H) 7.02-7.08 (m, 1H) 7.09 (d, J=1.9 Hz, 1H) 7.27 (dd, J=9.6, 2.4 Hz, 1H) 7.36 (d, J=8.2 Hz, 1H) 8.13 (dd, J=9.6, 5.5 Hz, 1H) 8.43 (s, 1H) 11.63-12.47 (m, 1H)

LC/MS (method LC-C): R$_t$ 2.95 min, MH$^+$ 499

$[\alpha]_D^{20}$: −113.9° (c 0.28, DMF)

Chiral SFC (method SFC-D): R$_t$ 4.12 min, MH$^+$ 499, chiral purity 100%.

Synthesis of Enantiomer 13A-P

A stirring solution of Enantiomer 13A (250 mg, 0.5 mmol) in dioxane (15 mL), under N$_2$-atmosphere, was cooled on an ice-bath. 4M HCl in dioxane (125 µL, 0.5 mmol) was added, followed by phosphorous oxychloride (140 µL, 1.5 mmol). The ice-bath was removed, and the reaction mixture was stirred for 90 minutes. Extra phosphorous oxychloride (140 µL) was added and the reaction mixture was stirred at room temperature for 20 h. The reaction mixture was quenched by the addition of crushed ice (12 g). After stirring for 45 min, the organic volatiles were evaporated under reduced pressure until a residual volume of ~12 mL. The aqueous solution was purified via preparative HPLC (Stationary phase: RP XBridge® Prep C18 OBD-10 µm, 50×150 mm, Mobile phase: 0.25% NH$_4$HCO$_3$ solution in water, CH$_3$CN). The fractions containing product were combined and the organic volatiles were evaporated under reduced pressure. The remaining aqueous solution was co-evaporated with xylene to dryness. The residue was dissolved in CH$_3$CN and evaporated under reduced pressure to dryness. The residue was triturated with Et$_2$O. The solids were filtered off, washed with Et$_2$O (2×), and dried under vacuum at 45° C. to provide Enantiomer 13A-P (48 mg).

Enantiomer 13A-P:

$^1$H NMR (400 MHz, DMSO-d$_6$) δ ppm 3.60 (s, 3H) 3.88-4.01 (m, 7H) 5.72 (t, J=2.0 Hz, 1H) 5.93-5.99 (m, 2H) 6.17 (d, J=8.4 Hz, 1H) 6.38 (d, J=8.1 Hz, 1H) 6.96 (dd, J=8.1, 2.0 Hz, 1H) 6.99-7.09 (m, 2H) 7.27 (dd, J=9.6, 2.3 Hz, 1H) 7.40 (d, J=8.3 Hz, 1H) 8.12 (dd, J=8.8, 5.5 Hz, 1H) 8.47 (s, 1H)

LC/MS (method LC-A): $R_t$ 0.82 min, MH$^-$ 577

$[\alpha]_D^{20}$: +71.3° (c 0.46, DMF)

Chiral SFC (method SFC-G): $R_t$ 2.80 min, MH$^+$ 579, chiral purity 96.7%.

Example 13.3: Synthesis of 2-(4-chloro-2-methoxyphenyl)-2-deuterio-1-(6-fluoro-1H-indol-3-yl)-2-((3-(2-hydroxyethoxy)-5-methoxyphenyl)amino)ethanone (Compound 13-D) and chiral separation into Enantiomers 13A-D and 13B-D Synthesis of Deuterated Enantiomers 13A-D and 13B-D

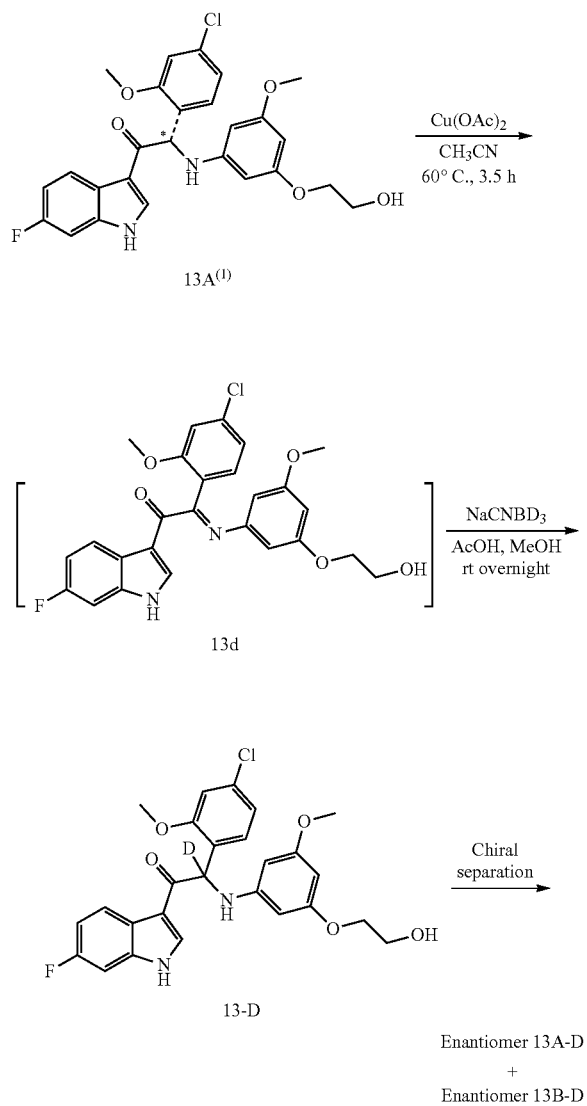

[1] The absolute stereochemistry of the chiral center (*) of enantiomer 13A has not been determined, and can therefore not be represented Synthesis of Compound 13-D and Chiral Separation into Enantiomers 13A-D and 13B-D:

Copper(II) acetate (634 mg, 3.49 mmol) was added to a stirring solution of Enantiomer 13A (871 mg, 1.75 mmol) in CH$_3$CN (100 mL) at room temperature. The reaction mixture was heated at 60° C. for 3.5 h. The reaction mixture was evaporated to dryness under reduced pressure and the black residue was taken up with CH$_2$Cl$_2$ and water. The layers were separated. The aqueous layer was extracted again with CH$_2$Cl$_2$. The combined organic layers were dried over MgSO$_4$, filtered, and evaporated under reduced pressure. The residue, containing crude intermediate 13d was dissolved in MeOH (100 mL). Sodium cyanoborodeuteride (172 mg, 2.62 mmol) and acetic acid (300 µL, 5.24 mmol) were added, and the reaction mixture was stirred at room temperature overnight under N$_2$-atmosphere. The solvent was evaporated under reduced pressure. Water, aqueous NaHCO$_3$ and CH$_2$Cl$_2$ were added and the layers were separated. The aqueous layer was extracted again with CH$_2$Cl$_2$. The combined organic layers were dried over MgSO$_4$ and the solvent was evaporated under reduced pressure. The residue was purified by column chromatography (Biotage® SNAP Ultra 50 g, eluent: EtOAc:EtOH(3:1)/heptane gradient 0/100 to 50/50). The product fractions were combined, concentrated under reduced pressure and dried under vacuum at 50° C. to give racemic 2-(4-chloro-2-methoxyphenyl)-2-deuterio-1-(6-fluoro-1H-indol-3-yl)-2-((3-(2-hydroxyethoxy)-5-methoxyphenyl)amino)ethanone (Compound 13-D, 356 mg) as a white solid.

The enantiomers of Compound 13-D (356 mg) were separated via preparative SFC (Stationary phase: Chiralpak® Diacel AD 20×250 mm, Mobile phase: CO$_2$, EtOH+ 0.4% iPrNH$_2$). The product fractions were combined and evaporated under reduced pressure to provide Enantiomer 13A-D as the first eluted product and Enantiomer 13B-D as the second eluted product. Both enantiomers were further purified by column chromatography (Biotage® SNAP Ultra silica 10 g, eluent: EtOAc:EtOH(3:1)/heptane gradient 0/100 to 50/50). The product fractions were combined, evaporated under reduced pressure and dried under vacuum at 50° C. to give Enantiomer 13A-D (115 mg, 94% deuterated according to $^1$H HMR) and Enantiomer 13B-D (125 mg, 94% deuterated according to $^1$H HMR) as white solids.

Enantiomer 13A-D:

$^1$H NMR (360 MHz, DMSO-d$_6$) δ ppm 3.61 (s, 3H) 3.64 (q, J=5.4 Hz, 2H) 3.76-3.89 (m, 2H) 3.96 (s, 3H) 4.80 (t, J=5.5 Hz, 1H) 5.71 (t, J=2.2 Hz, 1H) 5.93 (d, J=2.2 Hz, 2H) 6.41 (s, 1H) 6.97 (dd, J=8.2, 2.0 Hz, 1H) 7.06 (ddd, J=9.8, 8.9, 2.6 Hz, 1H) 7.09 (d, J=1.8 Hz, 1H) 7.27 (dd, J=9.5, 2.2 Hz, 1H) 7.36 (d, J=8.2 Hz, 1H) 8.13 (dd, J=8.8, 5.5 Hz, 1H) 8.44 (s, 1H) 12.09 (br s, 1H)

LC/MS (method LC-A): $R_t$ 1.06 min, MH$^+$ 500

$[\alpha]_D^{20}$: +102.8° (c 0.435, DMF)

Chiral SFC (method SFC-A): $R_t$ 3.57 min, MH$^+$ 500, chiral purity 100%.

Enantiomer 13B-D:

$^1$H NMR (360 MHz, DMSO-d$_6$) δ ppm 3.61 (s, 3H) 3.64 (q, J=5.1 Hz, 2H) 3.75-3.89 (m, 2H) 3.96 (s, 3H) 4.80 (t, J=5.7 Hz, 1H) 5.71 (t, J=2.0 Hz, 1H) 5.93 (d, J=2.2 Hz, 2H) 6.41 (s, 1H) 6.97 (dd, J=8.4, 2.2 Hz, 1H) 7.02-7.09 (m, 1H) 7.09 (d, J=1.8 Hz, 1H) 7.27 (dd, J=9.7, 2.4 Hz, 1H) 7.36 (d, J=8.4 Hz, 1H) 8.13 (dd, J=8.8, 5.5 Hz, 1H) 8.44 (s, 1H) 12.09 (br s, 1H)

LC/MS (method LC-A): $R_t$ 1.06 min, MH$^+$ 500

$[\alpha]_D^{20}$: -94.9° (c 0.435, DMF)

Chiral SFC (method SFC-A): $R_t$ 4.09 min, MH$^+$ 500, chiral purity 100%.

Example 14: Synthesis of 2-(4-chloro-2-methoxyphenyl)-2-deuterio-2-((3-(2-hydroxyethoxy)-5-methoxyphenyl)amino)-1-(6-methoxy-5-methyl-1H-indol-3-yl)ethanone (Compound 14-D) and chiral separation into Enantiomers 14A-D and 14B-D

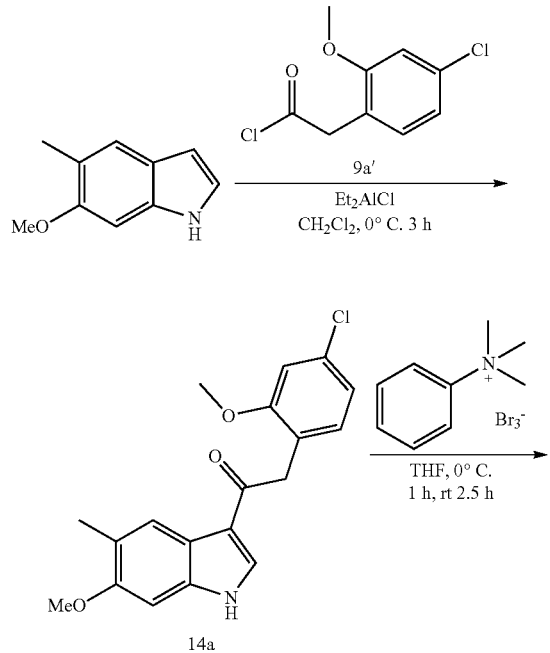

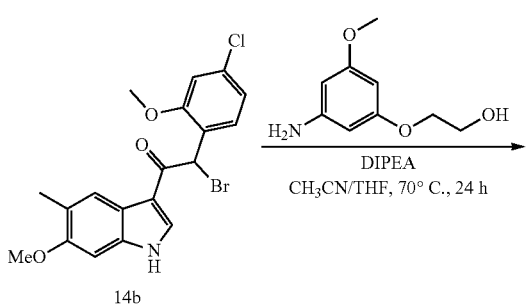

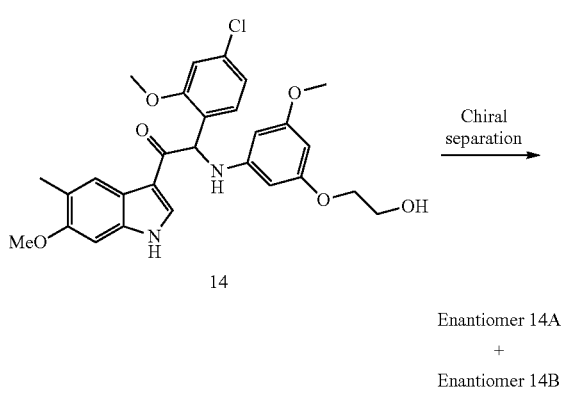

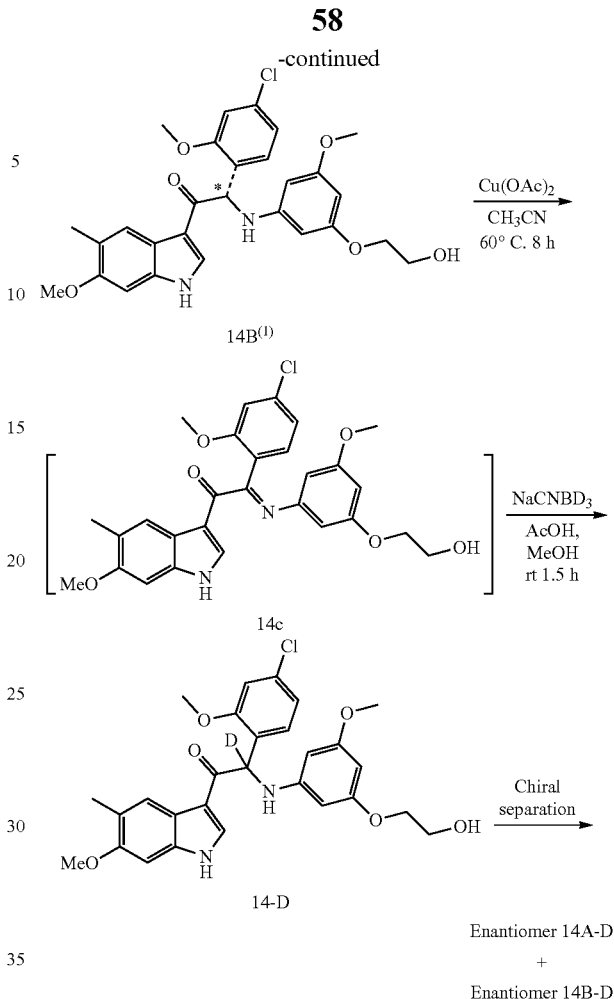

(1) The absolute stereochemistry of the chiral center (*) of enantiomer 14B has not been determined, and can therefore not be represented Synthesis of Intermediate 14a:

Diethylaluminum chloride 1M in hexane (13.5 mL, 13.5 mmol) was added dropwise at 0° C. to a solution of 6-methoxy-5-methyl-1H-indole [CAS 1071973-95-9] (1.45 g, 9 mmol) in $CH_2Cl_2$ (45 mL). After 30 min at 0° C., a solution of 2-(4-chloro-2-methoxyphenyl)acetyl chloride 9a' (2.4 g, 10.9 mmol) in $CH_2Cl_2$ (45 mL) was added slowly at 0° C. The reaction was stirred at 0° C. for 3 h. Ice-water was added and the precipitate was filtered off and washed with water. The solid was dried under vacuum to give 2-(4-chloro-2-methoxyphenyl)-1-(6-methoxy-5-methyl-1H-indol-3-yl)ethanone 14a (2.1 g).

Synthesis of Intermediate 14b:

At 0° C., a solution of phenyltrimethylammonium tribromide [CAS 4207-56-1] (2.4 g, 6.4 mmol) in THF (65 mL) was added dropwise to a mixture of 2-(4-chloro-2-methoxyphenyl)-1-(6-methoxy-5-methyl-1H-indol-3-yl)ethanone 14a (2.1 g, 6.1 mmol) in THF (60 mL). The mixture was stirred at 0° C. for 1 h and at room temperature for 2.5 h. The precipitate was filtered off and washed with EtOAc. The filtrate was concentrated under reduced pressure. The residue was taken up with the minimum of diisopropyl ether. The precipitate was filtered off and dried under vacuum to give 2-bromo-2-(4-chloro-2-methoxyphenyl)-1-(6-methoxy-5-methyl-1H-indol-3-yl)ethanone 14b (2.36 g).

Synthesis of Compound 14 and chiral Separation into Enantiomers 14A and 14B:

A mixture of 2-bromo-2-(4-chloro-2-methoxyphenyl)-1-(6-methoxy-5-methyl-1H-indol-3-yl)ethanone 14b (1.35 g, 3.2 mmol), 2-(3-amino-5-methoxyphenoxy)ethanol [CAS 725237-16-1] (0.585 g, 3.2 mmol) and diisopropylethylamine (0.83 mL, 4.8 mmol) in $CH_3CN$/THF (1/1) (80 mL) was stirred at 70° C. for 24 h. The mixture was concentrated under reduced pressure. The residue was diluted with $CH_2Cl_2$, washed with 1N HCl and water. The organic layer was separated, dried over $MgSO_4$, filtered and the solvent was evaporated under reduced pressure. The crude compound was purified by column chromatography on silica gel (15-40 μm, 80 g in $CH_2Cl_2$/MeOH 99.5/0.5). A small amount was crystallized from $Et_2O$/$CH_3CN$ to give an analytical sample of 2-(4-chloro-2-methoxyphenyl)-2-((3-(2-hydroxyethoxy)-5-methoxyphenyl)amino)-1-(6-methoxy-5-methyl-1H-indol-3-yl)ethanone (Compound 14) as a racemic mixture. The remaining amount of crude Compound 14 (775 mg) was mixed with another batch (total amount 1.19 g) and was further purified twice via preparative LC (Stationary phase: irregular bare silica 150 g, Mobile phase: $CH_2Cl_2$/MeOH (98/2), and then toluene/iPrOH (95/5), prior to chiral separation.

The Enantiomers of Compound 14 (950 mg) were separated via Preparative Chiral SFC (Stationary phase: Chiralpak® IC 5 μm 250×30 mm, Mobile phase: 50% $CO_2$, 50% MeOH) to give 485 mg of the first eluted enantiomer and 480 mg of the second eluted enantiomer. The first eluted enantiomer was solidified from $CH_3CN$/$Et_2O$ to afford Enantiomer 14A (406 mg) as an amorphous white powder. The second eluted enantiomer was solidified from $CH_3CN$/$Et_2O$ to afford Enantiomer 14B (436 mg,) as an amorphous white powder.

Compound 14:

$^1$H NMR (400 MHz, DMSO-$d_6$) δ ppm 2.21 (s, 3H) 3.61 (s, 3H) 3.62-3.68 (m, 2H) 3.74-3.90 (m, 5H) 3.97 (s, 3H) 4.76 (t, J=4.8 Hz, 1H) 5.68-5.74 (m, 1H) 5.93 (d, J=1.5 Hz, 2H) 6.11 (d, J=7.6 Hz, 1H) 6.31 (d, J=7.6 Hz, 1H) 6.92 (s, 1H) 6.95 (dd, J=8.3, 1.8 Hz, 1H) 7.09 (d, J=1.8 Hz, 1H) 7.35 (d, J=8.3 Hz, 1H) 7.89 (s, 1H) 8.22 (s, 1H) 11.73 (br. s., 1H)

LC/MS (method LC-C): $R_t$ 3.02 min, MH$^+$ 525

Enantiomer 14A:

$^1$H NMR (500 MHz, DMSO-$d_6$) δ ppm 2.20 (s, 3H) 3.60 (s, 3H) 3.64 (q, J=5.3 Hz, 2H) 3.75-3.88 (m, 5H) 3.97 (s, 3H) 4.78 (t, J=5.3 Hz, 1H) 5.70 (t, J=2.0 Hz, 1H) 5.92 (d, J=2.0 Hz, 2H) 6.11 (d, J=7.9 Hz, 1H) 6.33 (d, J=7.9 Hz, 1H) 6.92 (s, 1H) 6.95 (dd, J=8.2, 1.9 Hz, 1H) 7.09 (d, J=1.9 Hz, 1H) 7.35 (d, J=8.2 Hz, 1H) 7.88 (s, 1H) 8.23 (s, 1H) 11.75 (br. s., 1H)

LC/MS (method LC-C): $R_t$ 3.04 min, MH$^+$ 525

$[α]_D^{20}$: +116.8° (c 0.4536, DMF)

Chiral SFC (method SFC-E): $R_t$ 2.40 min, MH$^+$ 525, chiral purity 100%.

Enantiomer 14B:

$^1$H NMR (500 MHz, DMSO-$d_6$) δ ppm 2.20 (s, 3H) 3.60 (s, 3H) 3.64 (q, J=5.4 Hz, 2H) 3.77-3.88 (m, 5H) 3.97 (s, 3H) 4.78 (t, J=5.4 Hz, 1H) 5.70 (t, J=2.0 Hz, 1H) 5.92 (d, J=2.0 Hz, 2H) 6.11 (d, J=7.9 Hz, 1H) 6.33 (d, J=7.9 Hz, 1H) 6.92 (s, 1H) 6.95 (dd, J=8.2, 1.9 Hz, 1H) 7.09 (d, J=1.9 Hz, 1H) 7.35 (d, J=8.2 Hz, 1H) 7.88 (s, 1H) 8.23 (s, 1H) 11.75 (br. s., 1H)

LC/MS (method LC-C): $R_t$ 3.04 min, MH$^+$ 525

$[α]_D^{20}$: −121.9° (c 0.3855, DMF)

Chiral SFC (method SFC-E): $R_t$ 3.75 min, MH$^+$ 525, chiral purity 99.86%.

Synthesis of Compound 14-D and Chiral Separation into Enantiomers 14A-D and 14B-D:

Copper(II) acetate (698 mg, 3.84 mmol) was added to a stirring solution of Enantiomer 14B (1.01 g, 1.92 mmol) in $CH_3CN$ (100 mL) at room temperature. The reaction mixture was heated at 60° C. for 8 h, and was subsequently kept at room temperature overnight. The reaction mixture was evaporated to dryness and the black residue was taken up with $CH_2Cl_2$ and water. The layers were separated. The aqueous layer was extracted again with $CH_2Cl_2$. The combined organic layers were washed with water, dried over $MgSO_4$, filtered, and evaporated under reduced pressure. The residue, containing crude intermediate 14c was dissolved in MeOH (100 mL) and the solution was degassed with $N_2$ for 1 h. Sodium cyanoborodeuteride (190 mg, 2.88 mmol) and acetic acid (330 μL, 5.77 mmol) were added and the reaction mixture was stirred at room temperature under $N_2$-atmosphere for 1.5 h. Aqueous $NaHCO_3$ and EtOAc were added and the layers were separated. The aqueous layer was extracted again with EtOAc. The combined organic layers were dried over $MgSO_4$ and the solvent was evaporated under reduced pressure. The residue was purified by column chromatography (Biotage® SNAP Ultra silica 50 g, eluent: EtOAc:EtOH(3:1)/heptane gradient 0/100 to 50/50). The product fractions were combined, evaporated under reduced pressure and dried under vacuum at 50° C. to give racemic 2-(4-chloro-2-methoxyphenyl)-2-deuterio-2-((3-(2-hydroxyethoxy)-5-methoxyphenyl)amino)-1-(6-methoxy-5-methyl-1H-indol-3-yl)ethanone (Compound 14-D, 504 mg) as a yellow solid.

The enantiomers of Compound 14-D (504 mg) were separated via preparative SFC (Stationary phase: Chiralpak® Diacel AD 20×250 mm, Mobile phase: $CO_2$, EtOH+ 0.4% $iPrNH_2$). The product fractions were combined and evaporated under reduced pressure to provide Enantiomer 14A-D as the first eluted product and Enantiomer 14B-D as the second eluted product. Both enantiomers were dissolved in MeOH (5 mL) and water was added dropwise until the solution became cloudy. The mixtures were then stirred until a white solid appeared. The white solids were filtered off, washed with a small amount of MeOH/water (1/1) and dried under vacuum at 50° C. to provide Enantiomer 14A-D (113 mg, 94% deuterated according to $^1$H NMR) and Enantiomer 14B-D (40 mg, 93% deuterated according to $^1$H NMR) as white solids.

Enantiomer 14A-D:

$^1$H NMR (360 MHz, DMSO-$d_6$) δ ppm 2.21 (s, 3H) 3.61 (s, 3H) 3.64 (q, J=5.4 Hz, 2H) 3.76-3.89 (m, 5H) 3.98 (s, 3H) 4.81 (t, J=5.7 Hz, 1H) 5.71 (t, J=2.0 Hz, 1H) 5.93 (d, J=2.2 Hz, 2H) 6.35 (s, 1H) 6.92 (s, 1H) 6.96 (dd, J=8.2, 2.0 Hz, 1H) 7.09 (d, J=2.2 Hz, 1H) 7.36 (d, J=8.4 Hz, 1H) 7.89 (d, J=0.7 Hz, 1H) 8.25 (s, 1H) 11.77 (br s, 1H)

LC/MS (method LC-A): $R_t$ 1.08 min, MH$^-$ 524

$[α]_D^{20}$: +121.9° (c 0.375, DMF)

Chiral SFC (method SFC-A): $R_t$ 4.03 min, MH$^+$ 526, chiral purity 100%.

Enantiomer 14B-D:

$^1$H NMR (360 MHz, DMSO-$d_6$) δ ppm 2.20 (s, 3H) 3.60 (s, 3H) 3.64 (q, J=5.1 Hz, 2H) 3.74-3.88 (m, 5H) 3.97 (s, 3H) 4.80 (t, J=5.5 Hz, 1H) 5.70 (t, J=2.2 Hz, 1H) 5.92 (d, J=2.2 Hz, 2H) 6.34 (s, 1H) 6.91 (s, 1H) 6.96 (dd, J=8.2, 2.0 Hz, 1H) 7.09 (d, J=2.2 Hz, 1H) 7.35 (d, J=8.1 Hz, 1H) 7.88 (d, J=0.7 Hz, 1H) 8.24 (s, 1H) 11.77 (s, 1H)

LC/MS (method LC-A): $R_t$ 1.08 min, MH$^-$ 524

$[α]_D^{20}$: −119.7° (c 0.36, DMF)

Chiral SFC (method SFC-A): $R_t$ 4.31 min, MH$^+$ 526, chiral purity 100%.

Example 15: Synthesis of 2-(4-chloro-2-methoxyphenyl)-2-((3-(2-hydroxyethoxy)-5-methoxyphenyl)amino)-1-(5-(pentafluoro-λ⁶-sulfanyl)-1H-indol-3-yl)ethanone (Compound 15) and chiral separation into Enantiomers 15A and 15B

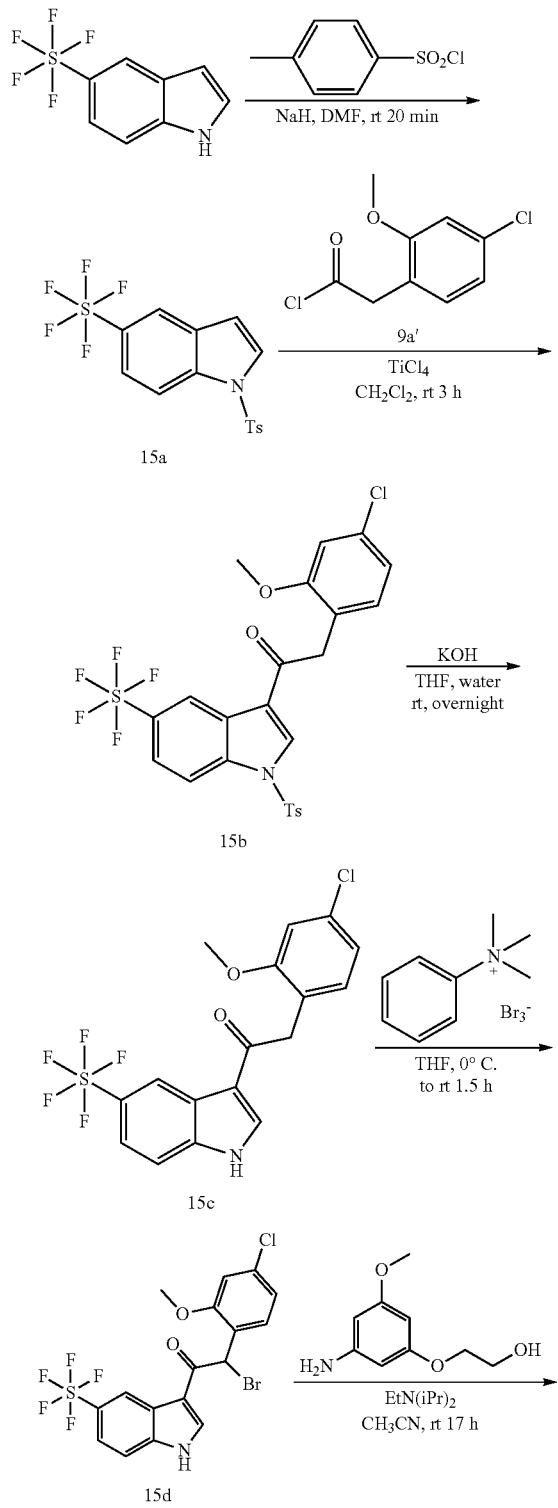

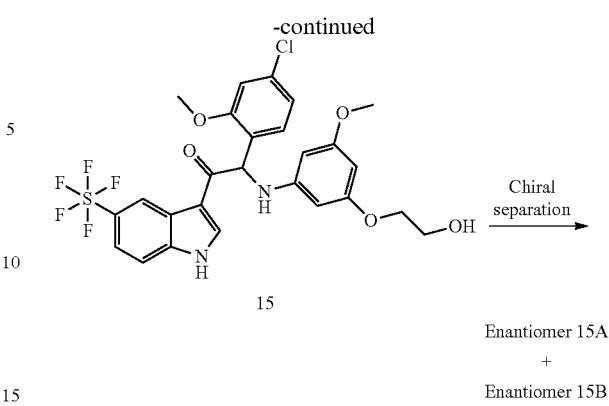

Enantiomer 15A
+
Enantiomer 15B

Synthesis of Intermediate 15a:

At 0° C., under a $N_2$ flow, sodium hydride (60% in oil, 189 mg, 4.93 mmol) was added portionwise to a mixture 5-(pentafluoro-X⁶-sulfanyl)-1H-indole [CAS 666841-01-6] (1 g, 4.11 mmol) in DMF (20 mL). The mixture was stirred at 0° C. for 20 min. A solution of tosyl chloride (862 mg, 4.52 mmol) in DMF (20 mL) was added dropwise. The ice-bath was removed and the mixture was stirred at room temperature for 20 min. The mixture was poured out in ice-water (100 mL) and vigorously stirred for 1 h. The precipitate was filtered off, washed with water (4×) and dried at 50° C. under vacuum to give 5-(pentafluoro-X⁶-sulfanyl)-1-tosyl-1H-indole 15a (1.63 g).

Synthesis of Intermediate 15b:

Titanium(IV) chloride (902 µL, 8.22 mmol) was added dropwise at room temperature to a stirred solution of 5-(pentafluoro-X⁶-sulfanyl)-1-tosyl-1H-indole 15a (1.63 g, 4.11 mmol) and 2-(4-chloro-2-methoxyphenyl)acetyl chloride 9a' (1.80 g, 8.23 mmol) in $CH_2CH_2$ (50 mL). The reaction was stirred at room temperature for 3 h. Crushed ice (40 g) was added, and after stirring for 45 min, the layers were separated. The organic layer was dried over $MgSO_4$, filtered, and the solvent was concentrated under reduced pressure. The residue was purified by column chromatography on silica gel (Stationary phase: Grace Reveleris® silica 80 g, Mobile phase: heptane/$CH_2Cl_2$ gradient 100/0 to 0/100). The product fractions were combined. The solvent was evaporated under reduced pressure and co-evaporated with dioxane. The residue was dried under vacuum at 50° C. to give 2-(4-chloro-2-methoxyphenyl)-1-(5-(pentafluoro-X⁶-sulfanyl)-1-tosyl-1H-indol-3-yl)ethanone 15b (1.01 g).

Synthesis of Intermediate 15c:

Potassium hydroxide (246 mg, 4.38 mmol) was added to a solution of 2-(4-chloro-2-methoxyphenyl)-1-(5-(pentafluoro-X⁶-sulfanyl)-1-tosyl-1H-indol-3-yl)ethanone 15b (1.01 g, 1.25 mmol) in dioxane (5 mL) and water (1.6 mL). The mixture was stirred at room temperature for 20 h. Ice-water (50 mL) and 1N HCl (11 mL) were added and the product was extracted with 2-Me-THF (2×). The combined organic layers were washed with brine, dried over $MgSO_4$, filtered and the solvent was evaporated under reduced pressure. The solid residue was stirred up with in $CH_2Cl_2$. The precipitate was filtered off, washed with $CH_2Cl_2$ (4×1 mL) and dried to give 2-(4-chloro-2-methoxyphenyl)-1-(5-(pentafluoro-X⁶-sulfanyl)-1H-indol-3-yl)ethanone 15c (391 mg).

Synthesis of Intermediate 15d:

At 0° C., phenyltrimethylammonium tribromide [CAS 4207-56-1] (362 mg, 0.964 mmol) was added to a solution of 2-(4-chloro-2-methoxyphenyl)-1-(5-(pentafluoro-X⁶-sulfanyl)-1H-indol-3-yl)ethanone 15c (391 mg, 0.918 mmol) in THF (15 mL). The mixture was stirred at 0° C. for 45 min and at room temperature for 1.5 h. The precipitate was filtered off and washed with THF (2×). The combined filtrates were concentrated under reduced pressure to provide 2-bromo-2-(4-chloro-2-methoxyphenyl)-1-(5-(pentafluoro-$X^6$-sulfanyl)-1H-indol-3-yl)ethanone 15d (510 mg) which was without further purification in the next step.

Synthesis of Compound 15 and Chiral Separation into Enantiomers 15A and 15B:

A mixture of 2-bromo-2-(4-chloro-2-methoxyphenyl)-1-(5-(pentafluoro-$X^6$-sulfanyl)-1H-indol-3-yl)ethanone 15d (510 mg, 0.92 mmol), 2-(3-amino-5-methoxyphenoxy)ethanol [CAS 725237-16-1] (337 mg, 1.84 mmol) and diisopropylethylamine (0.317 mL, 1.84 mmol) in $CH_3CN$ (30 mL) was stirred at room temperature for 17 h. Water (125 mL) was added and the product was extracted with $Et_2O$ (2×). The combined organic layers were washed with brine, dried over $MgSO_4$, filtered and evaporated under reduced pressure. The residue was purified by flash chromatography (Stationary phase: Biotage® SNAP Ultra silica 25 g, Mobile phase: heptane/EtOAc/EtOH gradient 100/0/0 to 40/45/15). The desired fractions were combined and evaporated under reduced pressure. The residue was further purified by preparative HPLC (Stationary phase: RP XBridge® Prep C18 ODB—5 µm, 30×250 mm, Mobile phase: 0.25% $NH_4HCO_3$ solution in water, MeOH). The product fractions were combined and concentrated under reduced pressure to give racemic Compound 15 (137 mg). The enantiomers were separated via Preparative Chiral SFC (Stationary phase: Chiralpak® Diacel AS 20×250 mm, Mobile phase: $CO_2$, EtOH+0.4% $iPrNH_2$). The product fractions were combined and evaporated under reduced pressure to provide Enantiomer 15A as the first eluted product and Enantiomer 15B as the second eluted product. Both enantiomers were solidified by precipitation from a solvent mixture of MeOH and water. The solids were filtered off and dried at 50° C. under vacuum to provide Enantiomer 15A (12 mg) and Enantiomer 15B (23 mg).

Enantiomer 15A:
$^1$H NMR (360 MHz, DMSO-$d_6$) δ ppm 3.61 (s, 3H) 3.62-3.67 (m, 2H) 3.76-3.88 (m, 2H) 3.94 (s, 3H) 4.80 (t, J=5.7 Hz, 1H) 5.73 (t, J=1.8 Hz, 1H) 5.93 (d, J=1.5 Hz, 2H) 6.19 (br d, J=8.1 Hz, 1H) 6.45 (br d, J=8.1 Hz, 1H) 6.98 (dd, J=7.7, 1.8 Hz, 1H) 7.11 (d, J=0.4 Hz, 1H) 7.37 (d, J=8.4 Hz, 1H) 7.63-7.69 (m, 1H) 7.70-7.76 (m, 1H) 8.65 (s, 2H) 12.48 (br s, 1H)
LC/MS (method LC-A): $R_t$ 1.19 min, MH$^+$ 607
$[α]_D^{20}$: +89.2° (c 0.269, DMF)
Chiral SFC (method SFC-A): $R_t$ 3.30 min, MH$^+$ 607, chiral purity 100%.

Enantiomer 15B:
$^1$H NMR (360 MHz, DMSO-$d_6$) δ ppm 3.61 (s, 3H) 3.62-3.67 (m, 2H) 3.76-3.89 (m, 2H) 3.94 (s, 3H) 4.80 (t, J=5.7 Hz, 1H) 5.73 (t, J=2.2 Hz, 1H) 5.93 (d, J=2.2 Hz, 2H) 6.19 (d, J=8.4 Hz, 1H) 6.45 (d, J=8.1 Hz, 1H) 6.98 (dd, J=8.2, 2.0 Hz, 1H) 7.10 (d, J=1.8 Hz, 1H) 7.37 (d, J=8.4 Hz, 1H) 7.64-7.69 (m, 1H) 7.71-7.75 (m, 1H) 8.65 (s, 2H) 12.49 (br s, 1H)
LC/MS (method LC-A): $R_t$ 1.20 min, MH$^+$ 607
$[α]_D^{20}$: −86.9° (c 0.2555, DMF)
Chiral SFC (method SFC-A): $R_t$ 3.61 min, MH$^+$ 607, chiral purity 99.4%.

TABLE

| compounds prepared as described above | | |
|---|---|---|
| Compound | Structure | Optical rotation |
| 1 | 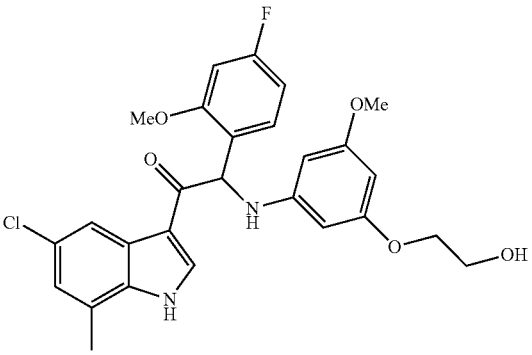 [SMILES: COc1cc(NC(C(=O)c2c[nH]c3c(C)cc(Cl)cc23)c2ccc(F)cc2OC)cc(OCCO)c1] | racemic |
| 1A | 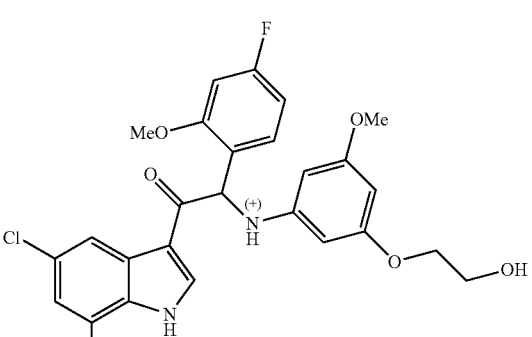 | $[α]_D^{20}$ = +107.2° |

TABLE-continued compounds prepared as described above

| Compound | Structure | Optical rotation |
| --- | --- | --- |
| 1B | 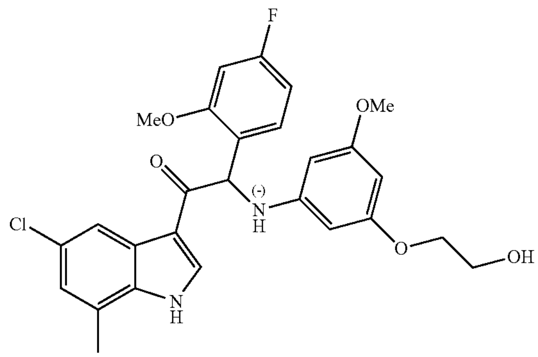 [SMILES: COc1cc(NC(C(=O)c2c[nH]c3c(C)cc(Cl)cc23)c2ccc(F)cc2OC)cc(OCCO)c1] | $[\alpha]_D^{20} = -107.5°$ |
| 2 | 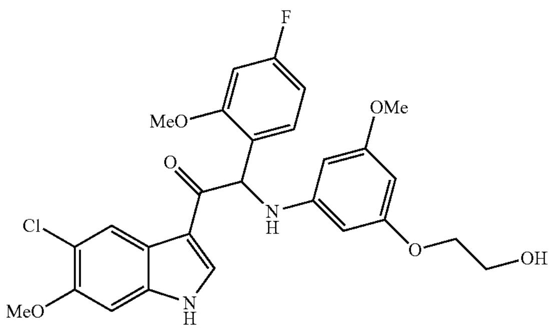 [SMILES: COc1cc(NC(C(=O)c2c[nH]c3cc(OC)c(Cl)cc23)c2ccc(F)cc2OC)cc(OCCO)c1] | racemic |
| 2A | 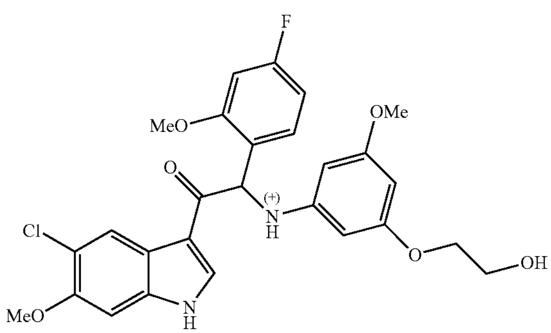 [SMILES: COc1cc(NC(C(=O)c2c[nH]c3cc(OC)c(Cl)cc23)c2ccc(F)cc2OC)cc(OCCO)c1] | $[\alpha]_D^{20} = +114.4°$ |
| 2B | 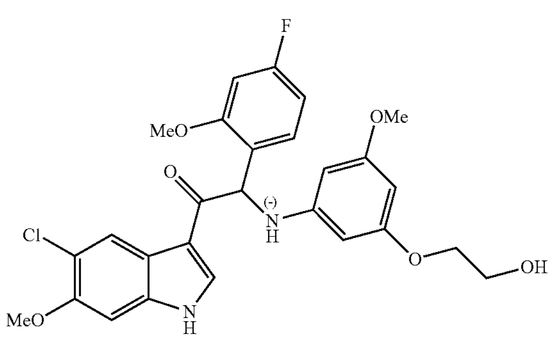 [SMILES: COc1cc(NC(C(=O)c2c[nH]c3cc(OC)c(Cl)cc23)c2ccc(F)cc2OC)cc(OCCO)c1] | $[\alpha]_D^{20} = -114.1°$ |

TABLE-continued compounds prepared as described above

| Compound | Structure | Optical rotation |
| --- | --- | --- |
| 3 | 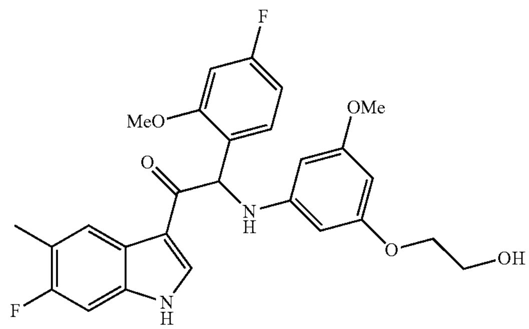 [SMILES: COc1cc(NC(C(=O)c2c[nH]c3cc(F)c(C)cc23)c2ccc(F)cc2OC)cc(OCCO)c1] | racemic |
| 3A | 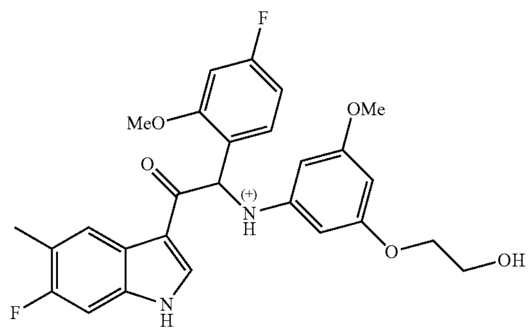 [SMILES: COc1cc(NC(C(=O)c2c[nH]c3cc(F)c(C)cc23)c2ccc(F)cc2OC)cc(OCCO)c1] | $[\alpha]_D^{20} = +122.8°$ |
| 3B | 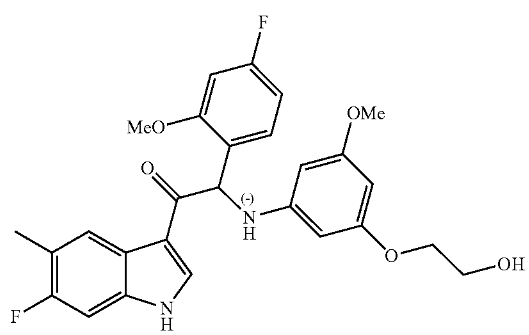 [SMILES: COc1cc(NC(C(=O)c2c[nH]c3cc(F)c(C)cc23)c2ccc(F)cc2OC)cc(OCCO)c1] | $[\alpha]_D^{20} = -121.5°$ |
| 4 | 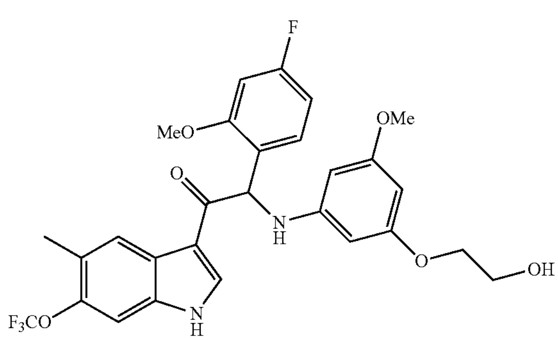 [SMILES: COc1cc(NC(C(=O)c2c[nH]c3cc(OC(F)(F)F)c(C)cc23)c2ccc(F)cc2OC)cc(OCCO)c1] | racemic |

TABLE-continued compounds prepared as described above

| Compound | Structure | Optical rotation |
| --- | --- | --- |
| 4A | 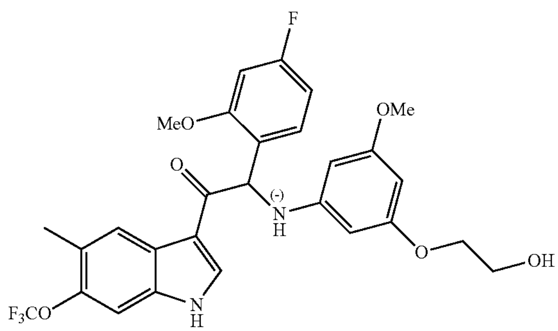 [SMILES: COc1cc(NC(C(=O)c2c[nH]c3cc(OC(F)(F)F)c(C)cc23)c2ccc(F)cc2OC)cc(OCCO)c1] | $[\alpha]_D^{20} = -96.76°$ |
| 4B | 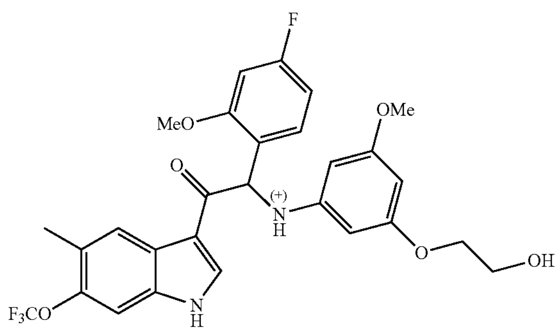 [SMILES: COc1cc(NC(C(=O)c2c[nH]c3cc(OC(F)(F)F)c(C)cc23)c2ccc(F)cc2OC)cc(OCCO)c1] | $[\alpha]_D^{20} = +98.79°$ |
| 5 | 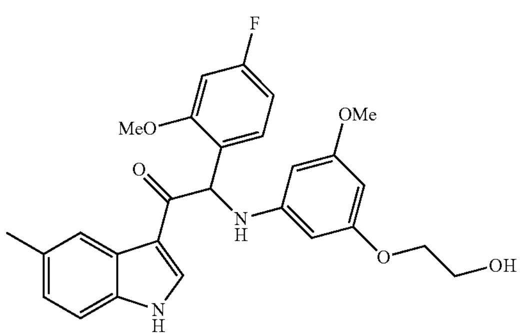 [SMILES: COc1cc(NC(C(=O)c2c[nH]c3ccc(C)cc23)c2ccc(F)cc2OC)cc(OCCO)c1] | racemic |
| 5A | 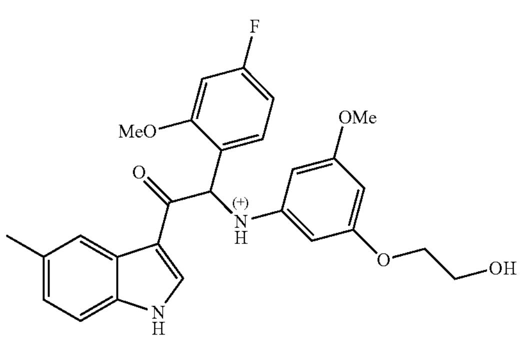 [SMILES: COc1cc(NC(C(=O)c2c[nH]c3ccc(C)cc23)c2ccc(F)cc2OC)cc(OCCO)c1] | $[\alpha]_D^{20} = +139.8°$ |

TABLE-continued compounds prepared as described above

| Compound | Structure | Optical rotation |
|---|---|---|
| 5B | 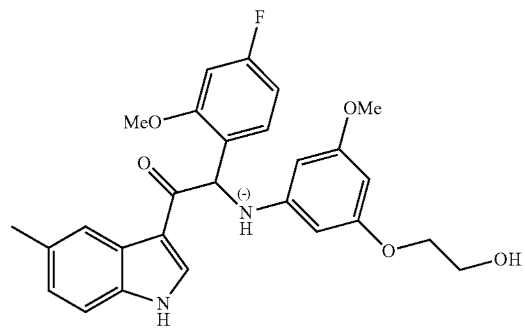 [SMILES: COc1cc(NC(C(=O)c2c[nH]c3ccc(C)cc23)c2ccc(F)cc2OC)cc(OCCO)c1] | $[\alpha]_D^{20} = -135.9°$ |
| 6 | 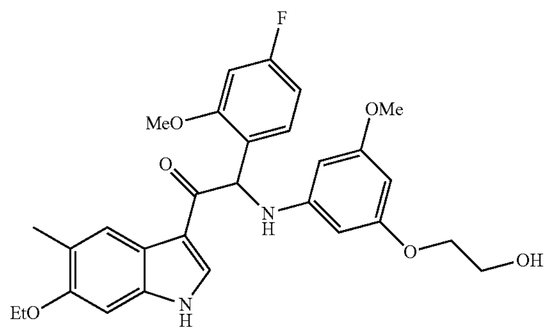 [SMILES: CCOc1cc2[nH]cc(C(=O)C(Nc3cc(OC)cc(OCCO)c3)c3ccc(F)cc3OC)c2cc1C] | racemic |
| 7 | 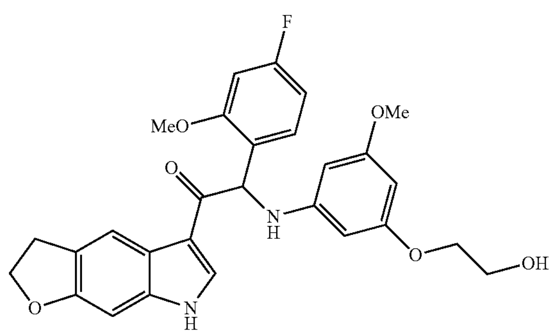 [SMILES: COc1cc(NC(C(=O)c2c[nH]c3cc4c(cc23)CCO4)c2ccc(F)cc2OC)cc(OCCO)c1] | racemic |
| 7A | 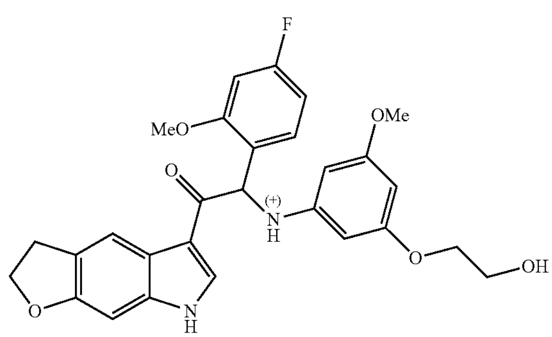 [SMILES: COc1cc(NC(C(=O)c2c[nH]c3cc4c(cc23)CCO4)c2ccc(F)cc2OC)cc(OCCO)c1] | $[\alpha]_D^{20} = +128.6°$ |

TABLE-continued compounds prepared as described above

| Compound | Structure | Optical rotation |
|---|---|---|
| 7B | 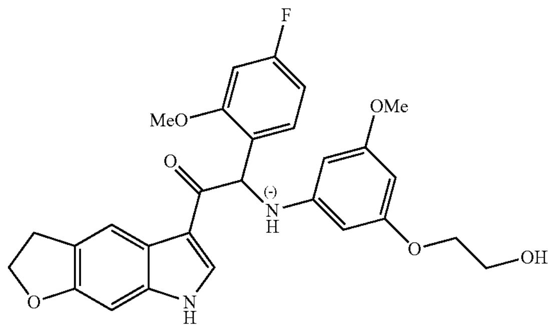 | $[\alpha]_D^{20} = -134.2°$ |
| 8 | 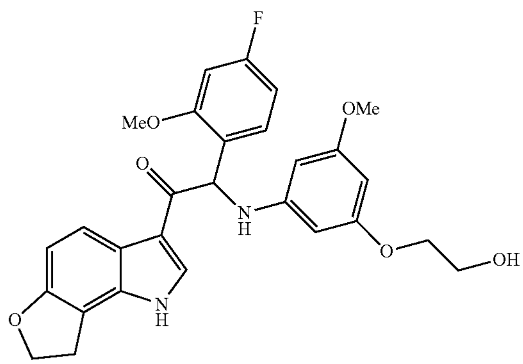 [SMILES: COc1cc(NC(C(=O)c2c[nH]c3c4c(ccc23)OCC4)c2ccc(F)cc2OC)cc(OCCO)c1] | racemic |
| 8A | 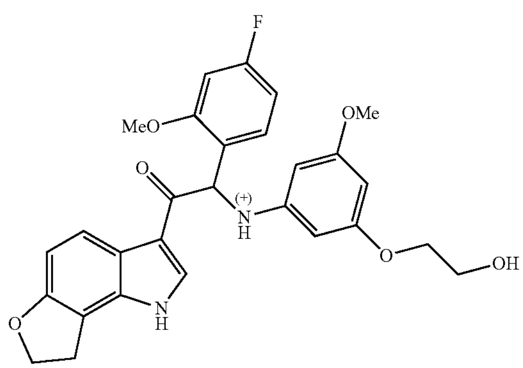 | $[\alpha]_D^{20} = +74.9°$ |
| 8B | 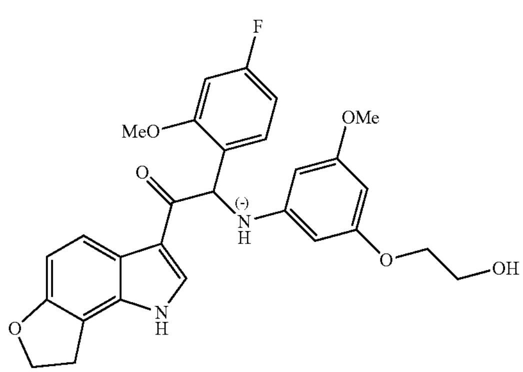 [SMILES: COc1cc(NC(C(=O)c2c[nH]c3c4c(ccc23)OCC4)c2ccc(F)cc2OC)cc(OCCO)c1] | $[\alpha]_D^{20} = -73.3°$ |

TABLE-continued compounds prepared as described above

| Compound | Structure | Optical rotation |
|---|---|---|
| 9 | 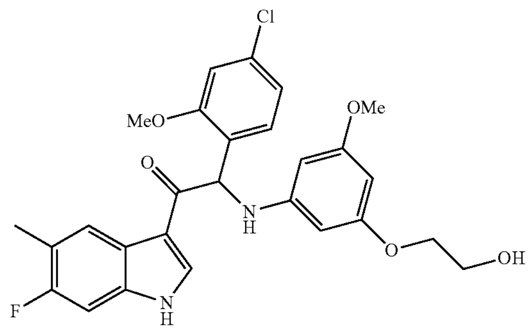 | racemic |
| 9A | 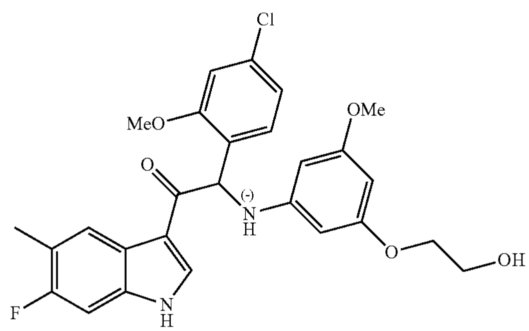 | $[\alpha]_D^{20} = -141.9°$ |
| 9B | 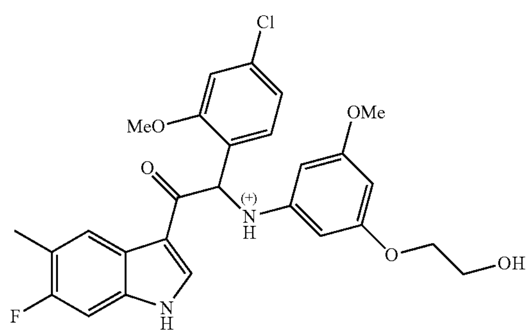 | $[\alpha]_D^{20} = +140.8°$ |
| 10 | 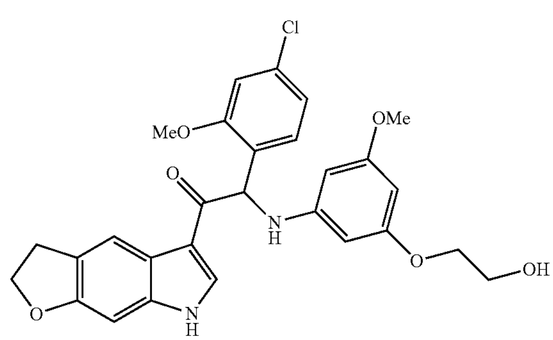 | racemic |

TABLE-continued compounds prepared as described above

| Compound | Structure | Optical rotation |
|---|---|---|
| 10A | 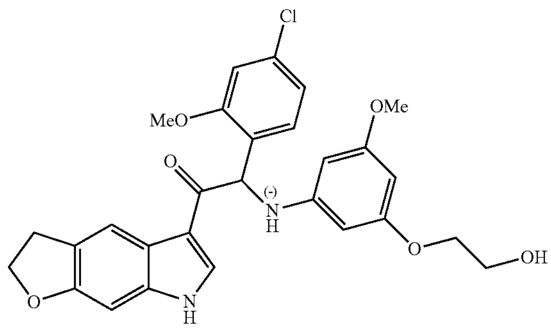 | $[\alpha]_D^{20} = -166.0°$ |
| 10B | 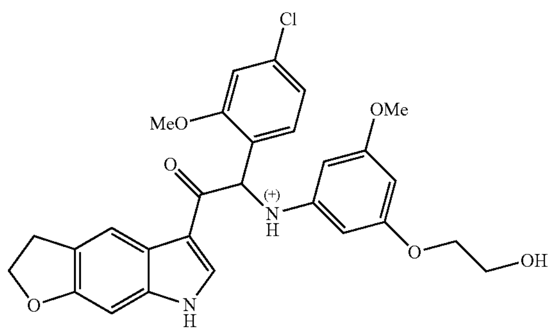 | $[\alpha]_D^{20} = +166.7°$ |
| 11 | 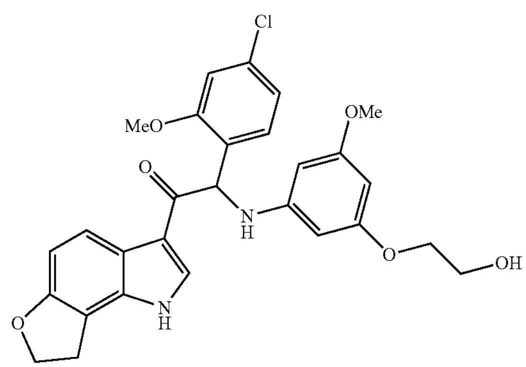 [SMILES: COc1cc(NC(C(=O)c2c[nH]c3c4c(ccc23)OCC4)c2ccc(Cl)cc2OC)cc(OCCO)c1] | racemic |
| 11A | 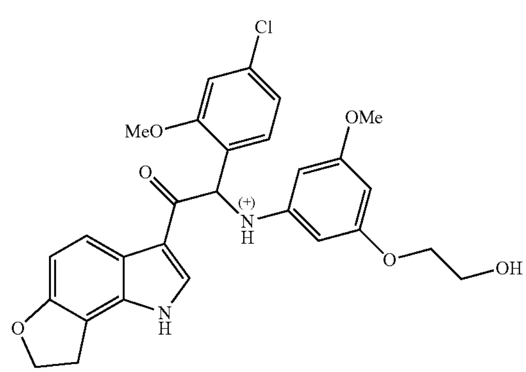 [SMILES: COc1cc(NC(C(=O)c2c[nH]c3c4c(ccc23)OCC4)c2ccc(Cl)cc2OC)cc(OCCO)c1] | $[\alpha]_D^{20} = +67.5°$ |

TABLE-continued
compounds prepared as described above
| Compound | Structure | Optical rotation |
|---|---|---|
| 11B | 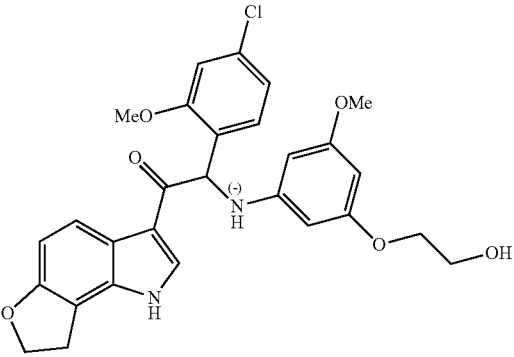 | $[\alpha]_D^{20} = -71.2°$ |
| 12 | 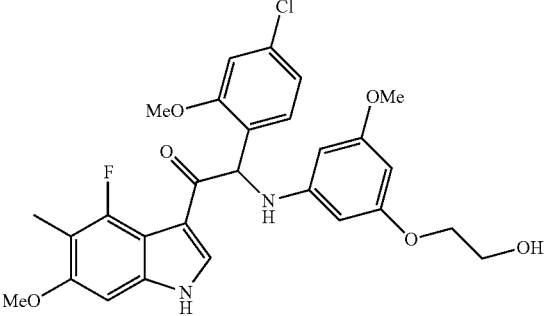 [SMILES: COc1cc(NC(C(=O)c2c[nH]c3cc(OC)c(C)c(F)c23)c2ccc(Cl)cc2OC)cc(OCCO)c1] | racemic |
| 12A | 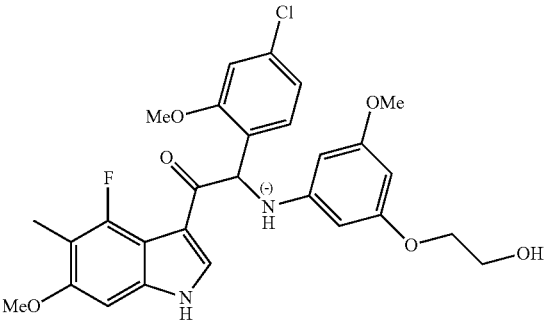 [SMILES: COc1cc(NC(C(=O)c2c[nH]c3cc(OC)c(C)c(F)c23)c2ccc(Cl)cc2OC)cc(OCCO)c1] | $[\alpha]_D^{20} = -110.4°$ |
| 12B | 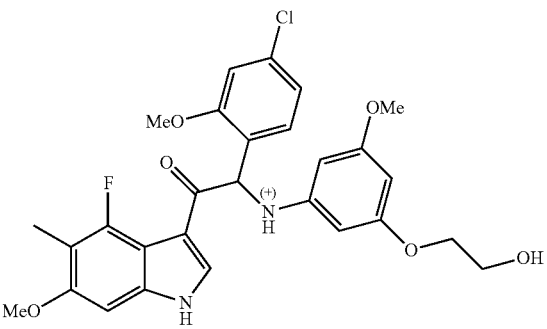 [SMILES: COc1cc(NC(C(=O)c2c[nH]c3cc(OC)c(C)c(F)c23)c2ccc(Cl)cc2OC)cc(OCCO)c1] | $[\alpha]_D^{20} = +123.7°$ |

TABLE-continued
compounds prepared as described above
| Compound | Structure | Optical rotation |
| --- | --- | --- |
| 13-P | 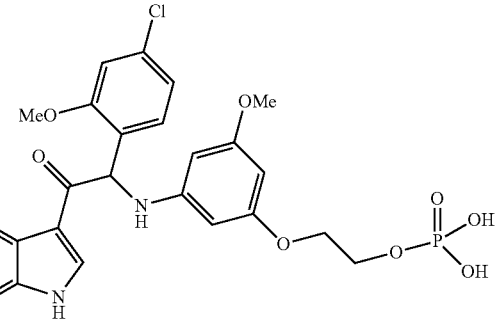 | racemic |
| 13A-P | 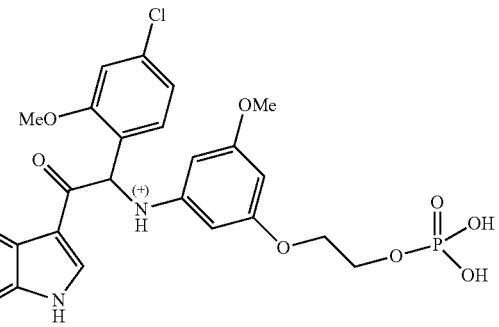 | $[\alpha]_D^{20} = +68.3°$ |
| 13B-P | 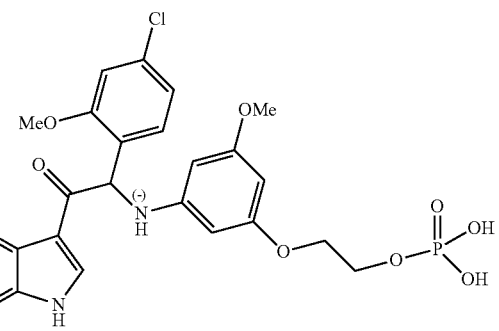 | $[\alpha]_D^{20} = -69.5°$ |
| 13-D | 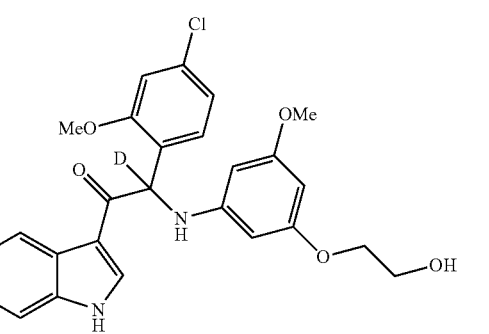 | racemic |

TABLE-continued compounds prepared as described above

| Compound | Structure | Optical rotation |
|---|---|---|
| 13A-D | 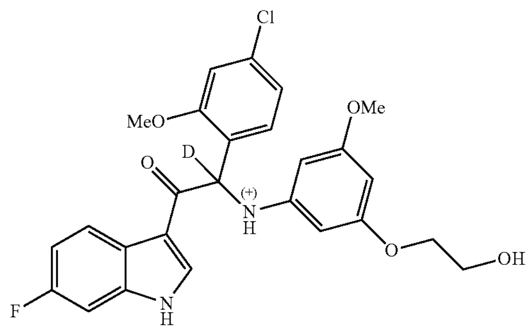 [SMILES: [2H]C(Nc1cc(OC)cc(OCCO)c1)(C(=O)c1c[nH]c2cc(F)ccc12)c1ccc(Cl)cc1OC] | $[\alpha]_D^{20} = +102.8°$ |
| 13B-D | 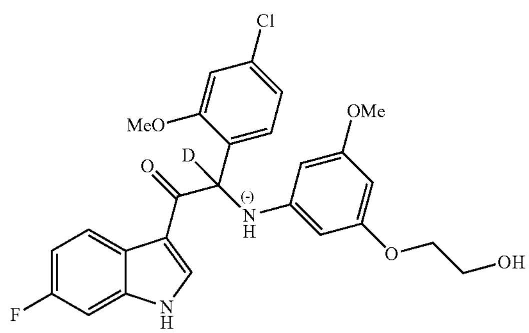 [SMILES: [2H]C(Nc1cc(OC)cc(OCCO)c1)(C(=O)c1c[nH]c2cc(F)ccc12)c1ccc(Cl)cc1OC] | $[\alpha]_D^{20} = -94.9°$ |
| 14-D | 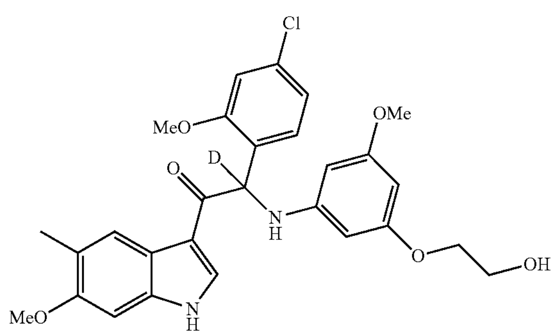 [SMILES: [2H]C(Nc1cc(OC)cc(OCCO)c1)(C(=O)c1c[nH]c2cc(OC)c(C)cc12)c1ccc(Cl)cc1OC] | racemic |
| 14A-D | 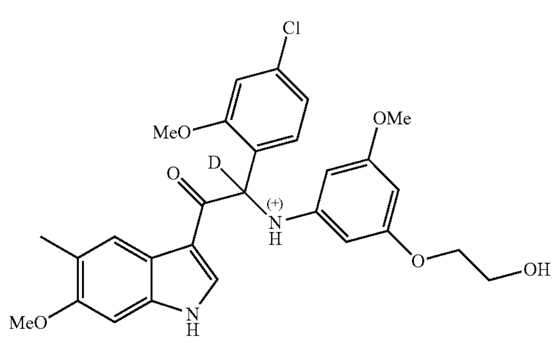 [SMILES: [2H]C(Nc1cc(OC)cc(OCCO)c1)(C(=O)c1c[nH]c2cc(OC)c(C)cc12)c1ccc(Cl)cc1OC] | $[\alpha]_D^{20} = +121.9°$ |

TABLE-continued compounds prepared as described above

| Compound | Structure | Optical rotation |
|---|---|---|
| 14B-D | (structure) | $[\alpha]_D^{20} = -119.7°$ |
| 15 | (structure) | racemic |
| 15A | (structure) | $[\alpha]_D^{20} = +89.2°$ |
| 15B | (structure) | $[\alpha]_D^{20} = -86.9°$ |

Antiviral Activity of the Compounds of the Invention
DENV-2 Antiviral Assay

The antiviral activity of all the compounds of the invention was tested against the DENV-2 16681 strain which was labeled with enhanced green fluorescent protein (eGPF). The culture medium consists of minimal essential medium supplemented with 2% of heat-inactivated fetal calf serum, 0.04% gentamycin (50 mg/mL) and 2 mM of L-glutamine. Vero cells, obtained from ECACC, were suspended in culture medium and 25 μL was added to 384-well plates (2500 cells/well), which already contain the antiviral compounds. Typically, these plates contain a 5-fold serial dilution of 9 dilution steps of the test compound at 200 times the final concentration in 100% DMSO (200 nL). In addition, each compound concentration is tested in quadruplicate (final concentration range: 25 μM-0.000064 μM or 2.5 μM-0.0000064 μM for the most active compounds). Finally, each plate contains wells which are assigned as virus controls (containing cells and virus in the absence of compound), cell controls (containing cells in the absence of virus and compound) and medium controls (containing medium in the absence of cells, virus and compounds). To the wells assigned as medium control, 25 µL of culture medium was added instead of Vero cells. Once the cells were added to the plates, the plates were incubated for 30 minutes at room temperature to allow the cells to distribute evenly within the wells. Next, the plates were incubated in a fully humidified incubator (37° C., 5% $CO_2$) until the next day. Then, DENV-2 strain 16681, labeled with eGFP, was added at a multiplicity of infection (MOI) of 0.5. Therefore, 15 µL of virus suspension was added to all the wells containing test compound and to the wells assigned as virus control. In parallel, 15 µL of culture medium was added to the medium and cell controls. Next, the plates were incubated for 3 days in a fully humidified incubator (37° C., 5% $CO_2$). At the day of the read out, the eGFP fluorescence was measured using an automated fluorescence microscope at 488 nm (blue laser). Using an in-house LIMS system, inhibition dose response curves for each compound were calculated and the half maximal effective concentration ($EC_{50}$) was determined. Therefore, the percent inhibition (I) for every test concentration is calculated using the following formula: $I=100*(S_T-S_{CC})/(S_{VC}-S_{CC})$; $S_T$, $S_{CC}$ and $S_{VC}$ are the amount of eGFP signal in the test compound, cell control and virus control wells, respectively. The $EC_{50}$ represents the concentration of a compound at which the virus replication is inhibited with 50%, as measured by a 50% reduction of the eGFP fluorescent intensity compared to the virus control. The $EC_{50}$ is calculated using linear interpolation (Table 1).

In parallel, the toxicity of the compounds was assessed on the same plates. Once the read-out for the eGFP signal was done, 40 µL of ATPlite, a cell viability stain, was added to all wells of the 384-well plates. ATP is present in all metabolically active cells and the concentration declines very rapidly when the cells undergo necrosis or apoptosis. The ATPLite assay system is based on the production of light caused by the reaction of ATP with added luciferase and D-luciferin. The plates were incubated for 10 minutes at room temperature. Next, the plates were measured on a ViewLux. The half maximal cytotoxic concentration ($CC_{50}$) was also determined, defined as the concentration required to reduce the luminescent signal by 50% compared to that of the cell control wells. Finally, the selectivity index (SI) was determined for the compounds, which was calculated as followed: $SI=CC_{50}/EC_{50}$.

TABLE 1

$EC_{50}$, $CC_{50}$ and SI for the compounds of the invention in the DENV-2 antiviral assay

| compound# | $EC_{50}$ (µM) | $N^a$ | $CC_{50}$ (µM) | N | SI | N |
|---|---|---|---|---|---|---|
| 1 | 0.0027 | 3 | 4.9 | 3 | 1800 | 3 |
| 1A | 0.0017 | 3 | 3.6 | 3 | 2070 | 3 |
| 1B | 0.072 | 3 | 11 | 3 | 148 | 3 |
| 2 | 0.0015 | 3 | 6.7 | 3 | 4410 | 3 |
| 2A | 0.00071 | 3 | 4.5 | 3 | 6340 | 3 |
| 2B | 0.13 | 4 | 11 | 4 | 85 | 4 |
| 3 | 0.0035 | 3 | 4.0 | 3 | 1140 | 3 |
| 3A | 0.0011 | 4 | 3.8 | 3 | 3230 | 3 |
| 3B | 0.25 | 3 | 8.0 | 3 | 31 | 3 |
| 4 | 0.011 | 3 | 3.9 | 3 | 359 | 3 |
| 4A | 0.63 | 3 | 3.4 | 3 | 5.4 | 3 |
| 4B | 0.0081 | 4 | 3.3 | 3 | 409 | 3 |
| 5 | 0.0048 | 3 | 14 | 3 | 3190 | 3 |
| 5A | 0.0025 | 3 | 5.8 | 3 | 2910 | 3 |

TABLE 1-continued $EC_{50}$, $CC_{50}$ and SI for the compounds of the invention in the DENV-2 antiviral assay

| compound# | $EC_{50}$ (µM) | $N^a$ | $CC_{50}$ (µM) | N | SI | N |
|---|---|---|---|---|---|---|
| 5B | 0.82 | 3 | 11 | 3 | 14 | 3 |
| 6 | 0.0018 | 3 | 5.7 | 3 | 3160 | 3 |
| 7A | 0.0010 | 3 | 10 | 3 | 13700 | 3 |
| 7B | 0.63 | 3 | 12 | 3 | 19 | 3 |
| 8A | 0.0043 | 3 | 12 | 3 | 4240 | 3 |
| 8B | 0.82 | 3 | 12 | 3 | 14 | 3 |
| 9 | 0.0012 | 3 | 3.1 | 4 | 2480 | 3 |
| 9A | 0.052 | 3 | 3.7 | 3 | 70 | 3 |
| 9B | 0.00044 | 4 | 3.0 | 3 | 7480 | 3 |
| 10A | 0.11 | 3 | 4.9 | 3 | 44 | 3 |
| 10B | 0.00032 | 3 | 9.5 | 3 | 19700 | 3 |
| 11A | 0.00088 | 4 | 6.0 | 4 | 7460 | 4 |
| 11B | 0.17 | 3 | 8.2 | 3 | 49 | 3 |
| 12A | 0.0060 | 3 | 5.6 | 3 | 1200 | 3 |
| 12B | 0.00026 | 5 | 4.6 | 6 | >48400 | 5 |
| 13-P | 0.0021 | 3 | 11 | 3 | 5210 | 3 |
| 13A-D | 0.00046 | 8 | 11 | 9 | 24300 | 7 |
| 13B-D | 0.17 | 5 | 9.6 | 6 | 54 | 5 |
| 13A-P[b] | 0.00048 | 4 | 11 | 5 | 23000 | 4 |
| 13A-P[c] | 0.00094 | 3 | 11 | 3 | 18700 | 3 |
| 13B-P | 0.013 | 3 | 11 | 3 | 822 | 3 |
| 14A-D | 0.00026 | 3 | 3.6 | 3 | 17600 | 3 |
| 14B-D | 0.11 | 3 | 6.0 | 3 | 52 | 3 |
| 15A | 0.00017 | 5 | 2.7 | 5 | 16000 | 5 |
| 15B | 0.013 | 5 | 5.8 | 5 | 460 | 5 |

[a]N = the number of independent experiments in which the compounds were tested.
[b]Isopropylamine salt of 13A-P
[c]Free form of 13A-P Tetravalent Reverse Transcriptase Quantitative-PCR (RT-qPCR) Assay The antiviral activity of the compounds of the invention was tested against DENV-1 strain TC974#666 (NCPV), DENV-2 strain 16681, DENV-3 strain H87 (NCPV) and DENV-4 strain H241 (NCPV) in a RT-qPCR assay. Therefore, Vero cells were infected with either DENV-1, or -2, or -3, or -4 in the presence or absence of test compounds. At day 3 post-infection, the cells were lysed and cell lysates were used to prepare cDNA of both a viral target (the 3'UTR of DENV; Table 2) and a cellular reference gene (β-actin, Table 2). Subsequently, a duplex real time PCR was performed on a Lightcycler480 instrument. The generated Cp value is inversely proportional to the amount of RNA expression of these targets. Inhibition of DENV replication by a test compound result in a shift of Cp's for the 3'UTR gene. On the other hand, if a test compound is toxic to the cells, a similar effect on β-actin expression will be observed. The comparative ΔΔCp method is used to calculate $EC_{50}$, which is based on the relative gene expression of the target gene (3'UTR) normalized with the cellular housekeeping gene (β-actin). In addition, $CC_{50}$ values are determined based on the Cp values acquired for the housekeeping gene β-actin.

TABLE 2

Primers and probes used for the real-time, quantitative RT-PCR.

| Primer/probe | Target | Sequence[a,b] |
|---|---|---|
| F3utr258 | DENV 3'-UTR | 5'-CGGTTAGAGGAGACCCCTC-3' |
| R3utr425 | DENV 3'-UTR | 5'-GAGACAGCAGGATCTCTGGTC-3' |

TABLE 2 -continued

Primers and probes used for the real-time, quantitative RT-PCR.

| Primer/probe | Target | Sequence[a,b] |
|---|---|---|
| P3utr343 | DENV 3'-UTR | FAM-5'-AAGGACTAG-ZEN-AGGTTAGAGGAGACCCCCC-3'-*IABkFQ* |
| Factin743 | β-actin | 5'-GGCCAGGTCATCACCATT-3' |
| Ractin876 | β-actin | 5'-ATGTCCACGTCACACTTCATG-3' |
| Pactin773 | β-actin | HEX-5'-TTCCGCTGC-ZEN-CCTGAGGCTCTC-3'-*IABkFQ* |

[a]Reporter dyes (FAM, HEX) and quenchers (ZEN and IABkFQ) elements are indicated in bold and italics.
[b]The nucleotide sequence of the primers and probes were selected from the conserved region in the 3'UTR region of the dengue virus genome, based on the alignment of 300 nucleotide sequences of the four dengue serotypes deposited in Genbank (Gong et al., 2013, Methods Mol Biol, Chapter 16).

The culture medium consisted of minimal essential medium supplemented with 2% of heat-inactivated fetal calf serum, 0.04% gentamycin (50 mg/mL) and 2 mM of L-glutamine. Vero cells, obtained from ECACC, were suspended in culture medium and 75 µL/well was added in 96-well plates (10000 cells/well), which already contain the antiviral compounds. Typically, these plates contain a 5-fold serial dilution of 9 dilution steps of the test compound at 200 times the final concentration in 100% DMSO (500 nL; final concentration range: 25 µM-0.000064 µM or 2.5 µM-0.0000064 µM for the most active compounds). In addition, each plate contains wells which are assigned as virus controls (containing cells and virus in the absence of compound) and cell controls (containing cells in the absence of virus and compound). Once the cells were added in the plates, the plates were incubated in a fully humidified incubator (37° C., 5% $CO_2$) until the next day. Dengue viruses serotype-1, 2, 3 and 4 were diluted in order to obtain a Cp of ~22-24 in the assay. Therefore, 25 µL of virus suspension was added to all the wells containing test compound and to the wells assigned as virus control. In parallel, 25 µL of culture medium was added to the cell controls. Next, the plates were incubated for 3 days in a fully humidified incubator (37° C., 5% $CO_2$). After 3 days, the supernatant was removed from the wells and the cells were washed twice with ice-cold PBS (~100 µL). The cell pellets within the 96-well plates were stored at −80° C. for at least 1 day. Next, RNA was extracted using the Cells-to-CT™ lysis kit, according to the manufacturer's guideline (Life Technologies). The cell lysates can be stored at −80° C. or immediately used in the reverse transcription step.

In preparation of the reverse transcription step, mix A (table 3A) was prepared and 7.57 µL/well was dispensed in a 96-well plate. After addition of 5 µL of the cell lysates, a five minute denaturation step at 75° C. was performed (table 3B). Afterwards, 7.43 µL of mix B was added (table 3C) and the reverse transcription step was initiated (table 3D) to generate cDNA.

Finally, a RT-qPCR mix was prepared, mix C (table 4A), and 22.02 µL/well was dispensed in 96-well LightCycler qPCR plates to which 3 µL of cDNA was added and the qPCR was performed according to the conditions in table 4B on a LightCycler 480.

Using the LightCycler software and an in-house LIMS system, dose response curves for each compound were calculated and the half maximal effective concentration ($EC_{50}$) and the half maximal cytotoxic concentration ($CC_{50}$) were determined (Tables 5-8).

TABLE 3 cDNA synthesis using Mix A, denaturation, Mix B and reverse transcription

A
Mix A

Plates 8
Samples 828

| | | Concentration | | Reaction Vol. (µl) 20 Volume for (µl) | |
|---|---|---|---|---|---|
| Mix Item | Unit | Stock | Final | 1 sample | x samples |
| Milli-Q $H_2O$ | | | | 7.27 | 6019.56 |
| R3utr425 | µM | 20 | 0.27 | 0.15 | 124.20 |
| Ractin876 | µM | 20 | 0.27 | 0.15 | 124.20 |
| | | Volume mix/well (µl) | | 7.57 | |
| | | Cell lysates | | 5.00 | |

B
Denaturation step:

| Step | Temp | Time |
|---|---|---|
| Denaturation | 75° C. | 5' |
| Hold | 4° C. | hold |

C
Mix B

Samples 864

| | | Concentration | | Volume for (µl) | |
|---|---|---|---|---|---|
| Mix Item | Unit | Stock | Final | 1 sample | x samples |
| Expand HIFI buffer 2 | X | 10.00 | 1.00 | 2.00 | 1728.0 |
| $MgCl_2$ | mM | 25.00 | 3.50 | 2.80 | 2419.2 |
| dNTPs | mM | 10.00 | 1.00 | 2.00 | 1728.0 |
| Rnase inhibitor | U/µl | 40.00 | 1.00 | 0.50 | 432.0 |
| Expand RT | U/µl | 50.00 | 0.33 | 0.13 | 112.3 |
| | | Total Volume Mix (µl) | | 7.43 | |

D
Protocol cDNA synthesis

| Step | Temp | Time |
|---|---|---|
| Rev transc | 42° C. | 30' |
| Denaturation | 99° C. | 5' |
| Hold | 4° C. | hold |

TABLE 4 qPCR mix and protocol.

A
Mix C

Samples 833

| | | Concentration | | Reaction Vol. (µl) 25 Volume for (µl) | |
|---|---|---|---|---|---|
| Mix Item | Unit | Stock | Final | 1 sample | x samples |
| $H_2O$ PCR grade Roche | | | | 7.74 | 6447.42 |
| Roche 2xMM mix | X | 2 | 1 | 12.50 | 10412.50 |
| F3utr258 | µM | 20 | 0.3 | 0.38 | 316.54 |
| R3utr425 | µM | 20 | 0.3 | 0.38 | 316.54 |
| P3utr343 | µM | 20 | 0.1 | 0.13 | 108.29 |
| Factin743 | µM | 20 | 0.3 | 0.38 | 316.54 |

TABLE 4-continued qPCR mix and protocol.

| | | | | | |
|---|---|---|---|---|---|
| Ractin876 | µM | 20 | 0.3 | 0.38 | 316.54 |
| Pactin773 | µM | 20 | 0.1 | 0.13 | 108.29 |
| | | Volume Mix/Tube (µl) | 22.02 | | |
| | | cDNA | 3.00 | | |

B
Protocol qPCR3

| Step | Temp | Time | Ramp rate | |
|---|---|---|---|---|
| preincub/denat | 95° C. | 10 min | 4.4 | |
| Denaturation | 95° C. | 10 sec | 4.4 | 40 cycles |
| annealing | 58° C. | 1 min | 2.2 | |
| Elongation | 72° C. | 1 sec | 4.4 | |
| Cooling | 40° C. | 10 sec | 1.5 | |

TABLE 5

$EC_{50}$, $CC_{50}$ and SI for the compounds against serotype 1 in the RT-qPCR assays

| | Protocol A RT-qPCR serotype 1 T

Prior Art Examples

Compound (350) disclosed in WO-2013/045516 has been tested in an analogous DENV-2 antiviral assay as the compounds of the present invention and their reported activity is listed below.

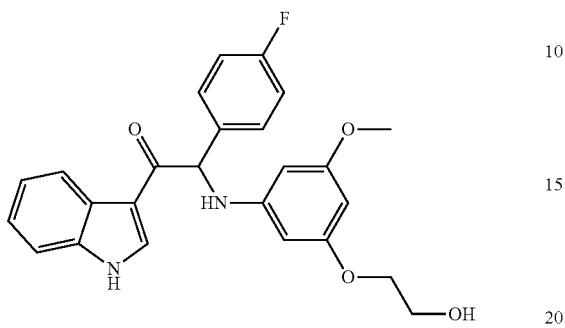

compound (350) of WO-2013/045516

TABLE 9

$EC_{50}$, $CC_{50}$, and SI for compounds (56) and (170) disclosed in the DENV-2 antiviral assay

| compound# | $EC_{50}$ (μM) | $CC_{50}$ (μM) | SI |
|---|---|---|---|
| (350) of WO-2013/045516 | 0.01 | 46 | 3462 |

The invention claimed is:

1. A compound of formula (Ia, Ib, II or IV) wherein formula (Ia) is represented by:

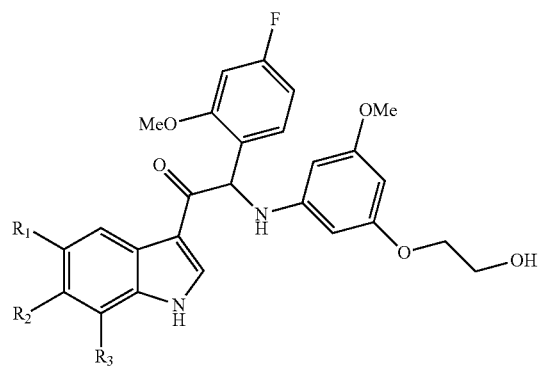

or wherein formula (Ib) is represented by:

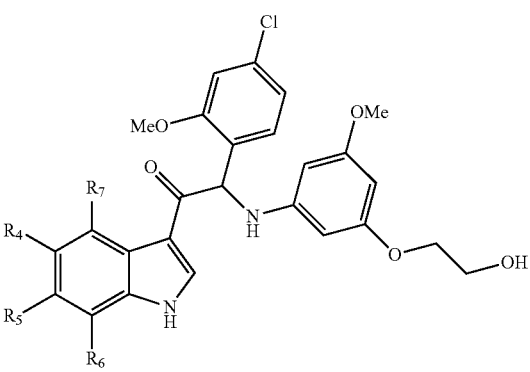

a stereoisomeric form, a pharmaceutically acceptable salt, solvate or polymorph thereof comprising a mono- or di-substituted indole group; said compound is selected from the group wherein:

$R_1$ is Cl, $R_2$ is H, $R_3$ is $CH_3$;

$R_1$ is Cl, $R_2$ is $OCH_3$, $R_3$ is H;

$R_1$ is $CH_3$, $R_2$ is F or $OCF_3$ or H or $OCH_2CH_3$ and $R_3$ is H;

$R_1$ and $R_2$ are connected forming a heterocycle of 5 members having one oxygen atom, $R_3$ is H;

$R_2$ and $R_3$ are connected forming a heterocycle of 5 members having one oxygen atom, $R_1$ is H;

a stereoisomeric form, a pharmaceutically acceptable salt, solvate or polymorph thereof comprising a mono- or di-substituted indole group; said compound is selected from the group wherein:

$R_4$ is $CH_3$, $R_5$ is F, $R_6$ and $R_7$ are both H;

$R_4$ is $CH_3$, $R_5$ is $OCH_3$, $R_6$ is H, $R_7$ is F;

$R_4$ is $SF_5$, $R_5=R_6=R_7$ are all H;

$R_4$ and $R_5$ are connected forming a heterocycle of 5 members having one oxygen atom, $R_6$ and $R_7$ are both H;

$R_5$ and $R_6$ are connected forming a heterocycle of 5 members having one oxygen atom, $R_4$ and $R_7$ are both H and wherein compounds (II and IV) respectively are represented by:
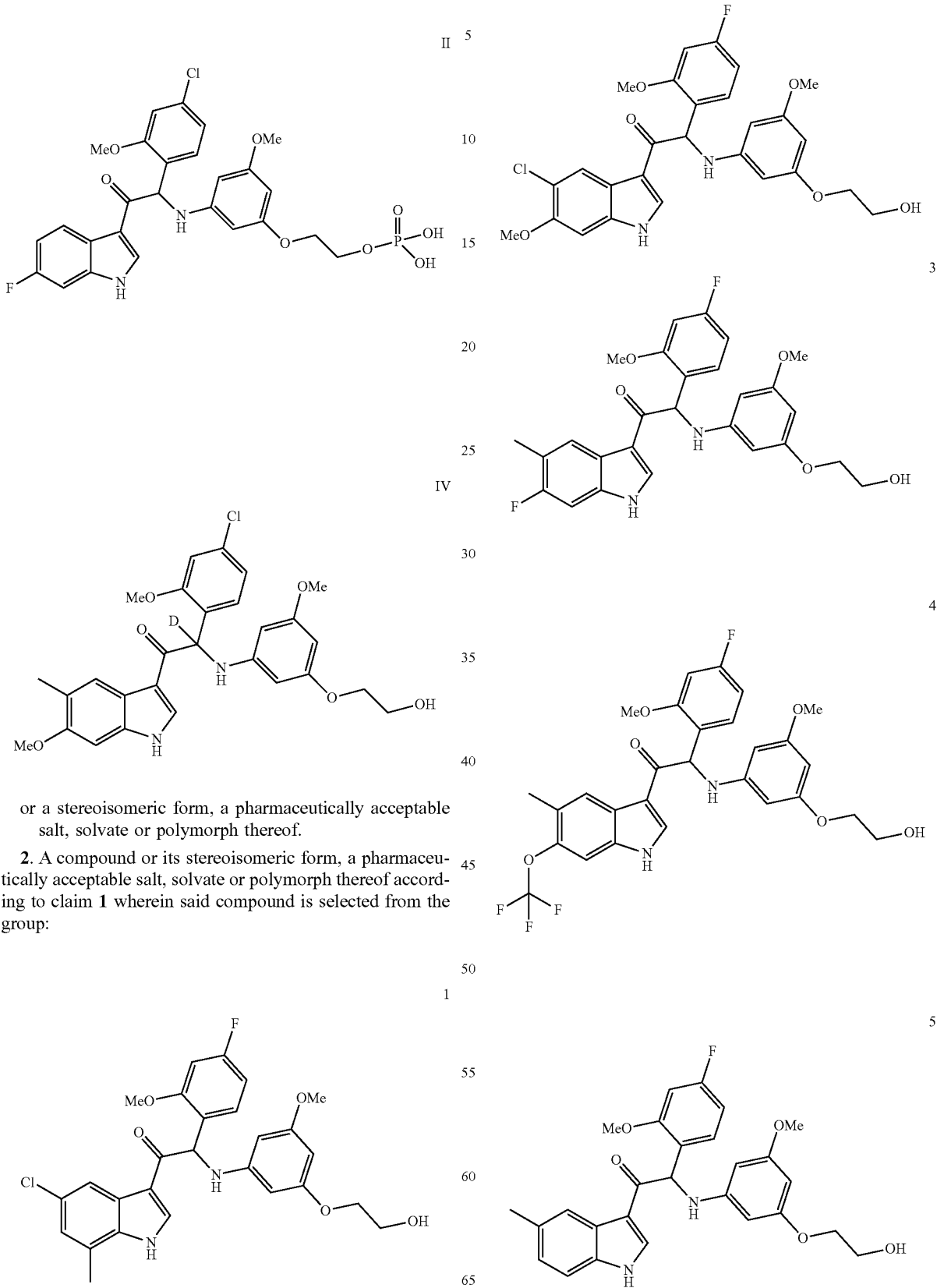
or a stereoisomeric form, a pharmaceutically acceptable salt, solvate or polymorph thereof.
2. A compound or its stereoisomeric form, a pharmaceutically acceptable salt, solvate or polymorph thereof according to claim 1 wherein said compound is selected from the group:

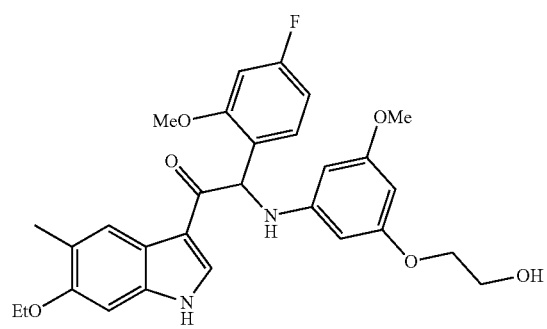
6
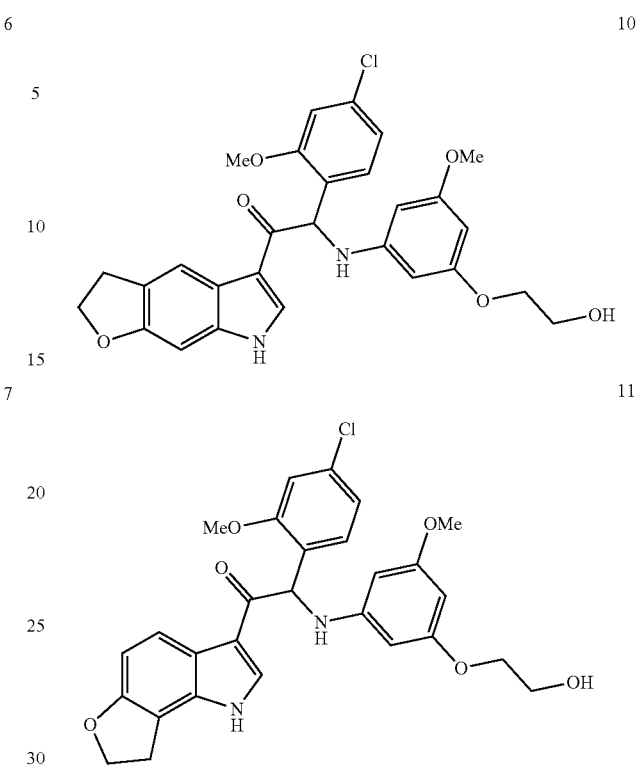
10
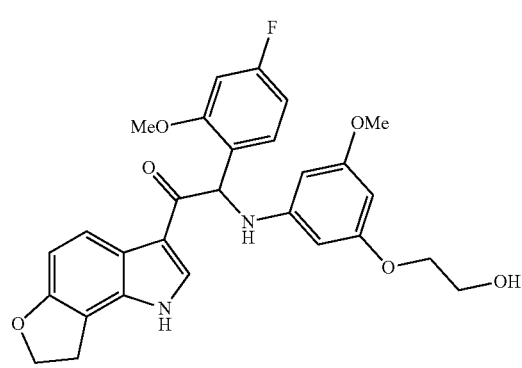
7
11
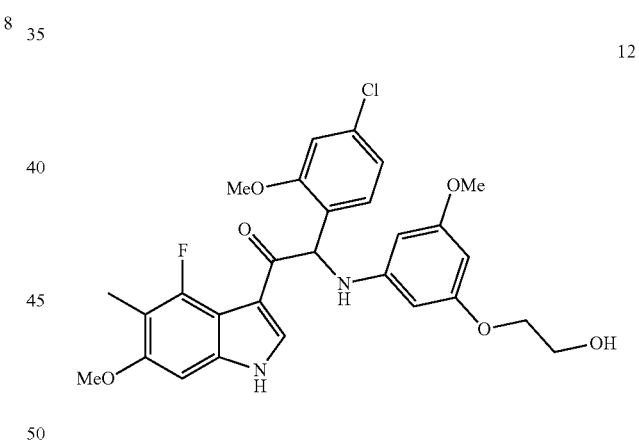
8
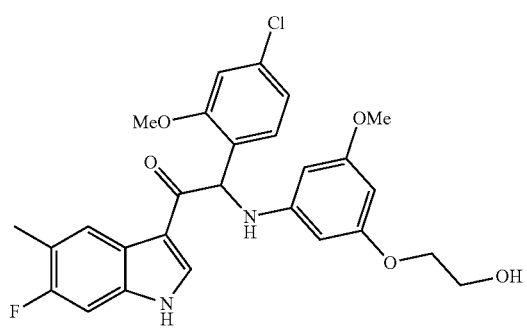
9
12
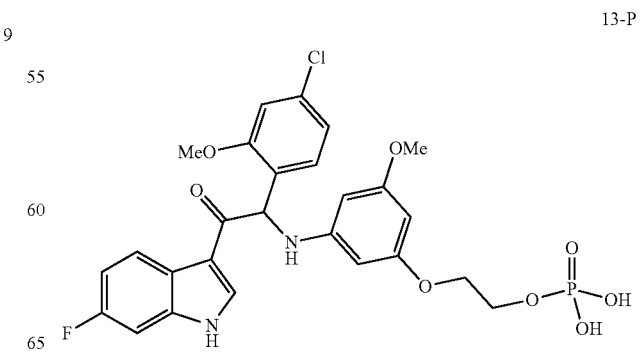
13-P

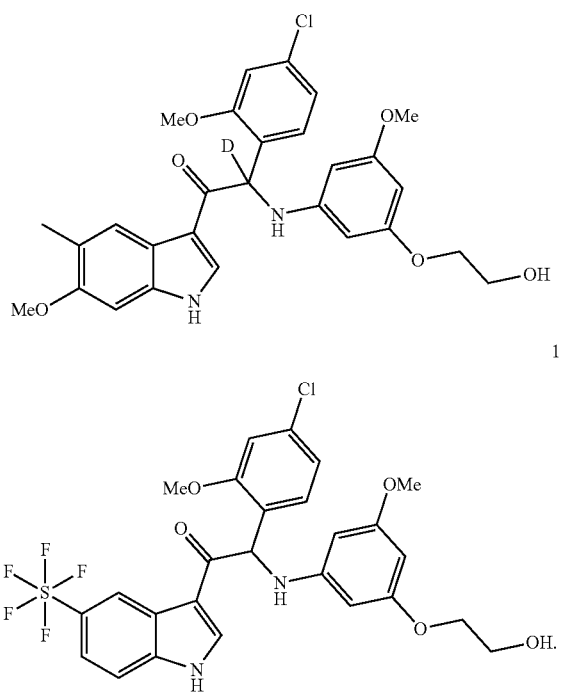
3. A pharmaceutical composition comprising a compound of formula (Ia, Ib, II or IV) or a stereoisomeric form, a pharmaceutically acceptable salt, solvate or polymorph thereof according to claim 1 together with one or more pharmaceutically acceptable excipients, diluents or carriers.
4. The compound as claimed in claim 1 wherein the compound is selected from
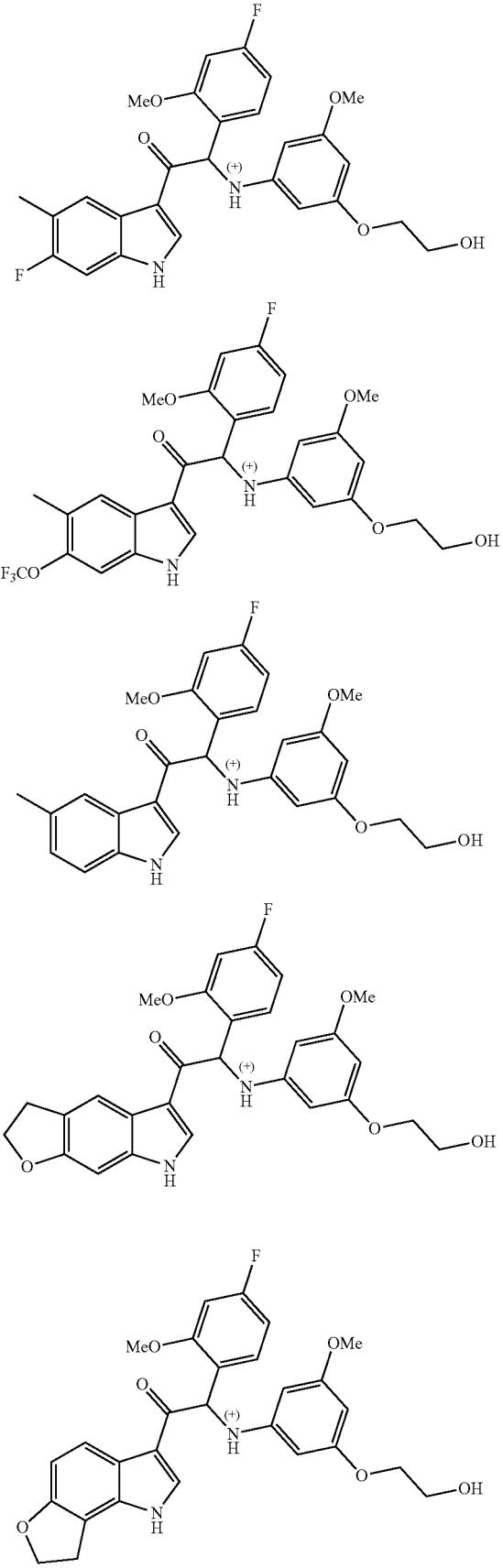

-continued

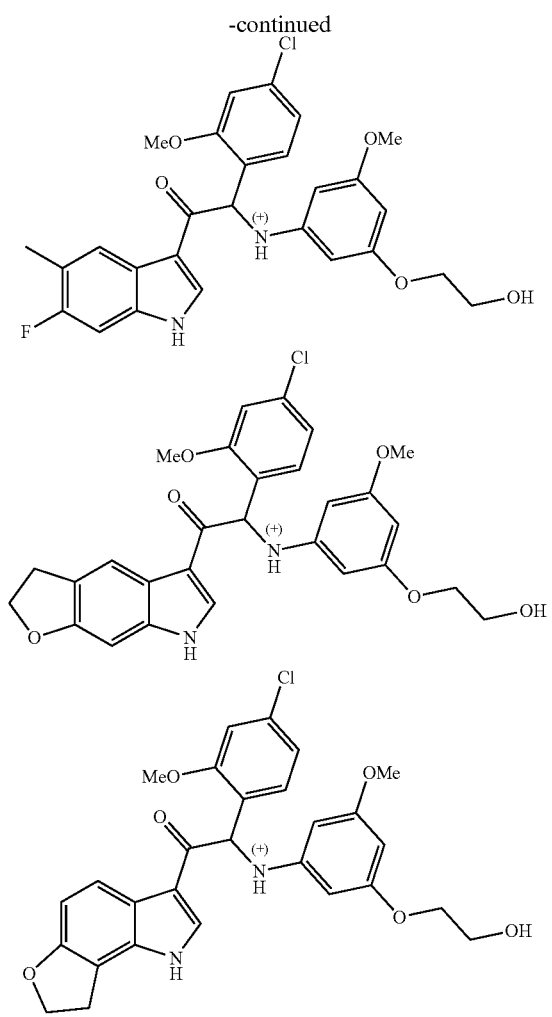

-continued

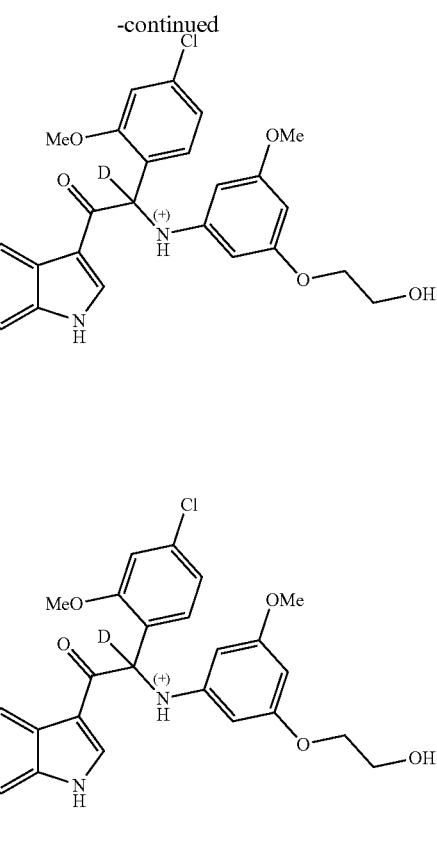

or a pharmaceutically acceptable salt, solvate or polymorph thereof.

5. A pharmaceutical composition comprising a compound according to claim 4, a pharmaceutically acceptable salt, solvate or polymorph thereof together with one or more pharmaceutically acceptable excipients, diluents or carriers.

6. A method of inhibiting replication of dengue virus, comprising contacting said dengue virus with a compound of claim 1.

* * * * *

SEQUENCE LISTING

```
<160> NUMBER OF SEQ ID NOS: 6

<210> SEQ ID NO 1
<211> LENGTH: 19
<212> TYPE: DNA
<213> ORGANISM: Dengue virus

<400> SEQUENCE: 1
cggttagagg agacccctc                                                  19

<210> SEQ ID NO 2
<211> LENGTH: 21
<212> TYPE: DNA
<213> ORGANISM: Dengue virus

<400> SEQUENCE: 2
gagacagcag gatctctggt c                                               21

<210> SEQ ID NO 3
<211> LENGTH: 28
<212> TYPE: DNA
<213> ORGANISM: Dengue virus

<400> SEQUENCE: 3
aaggactaga ggttagagga gaccccccc                                       28

<210> SEQ ID NO 4
<211> LENGTH: 18
<212> TYPE: DNA
<213> ORGANISM: Dengue virus
```

```
<400> SEQUENCE: 4
ggccaggtca tcaccatt                                              18

<210> SEQ ID NO 5
<211> LENGTH: 21
<212> TYPE: DNA
<213> ORGANISM: Dengue virus

<400> SEQUENCE: 5
atgtccacgt cacacttcat g                                          21

<210> SEQ ID NO 6
<211> LENGTH: 21
<212> TYPE: DNA
<213> ORGANISM: Dengue virus

<400> SEQUENCE: 6
ttccgctgcc ctgaggctct c                                          21
```